United States Patent
Showe et al.

(10) Patent No.: US 7,640,114 B2
(45) Date of Patent: Dec. 29, 2009

(54) METHOD OF DIAGNOSIS OF CANCER BASED ON GENE EXPRESSION PROFILES IN CELLS

(75) Inventors: Louise C. Showe, Media, PA (US); Michael K. Showe, Media, PA (US); Laszlo Kari, Hamilton, MT (US); Michael Nebozhyn, Yeadon, PA (US); Andrey Loboda, Philadelphia, PA (US)

(73) Assignee: The Wistar Institute of Anatomy & Biology, Philadelphia, PA (US)

( * ) Notice: Subject to any disclaimer, the term of this patent is extended or adjusted under 35 U.S.C. 154(b) by 409 days.

(21) Appl. No.: 10/558,252

(22) PCT Filed: May 21, 2004

(86) PCT No.: PCT/US2004/014521

§ 371 (c)(1), (2), (4) Date: Nov. 21, 2005

(87) PCT Pub. No.: WO2004/105573

PCT Pub. Date: Dec. 9, 2004

(65) Prior Publication Data

US 2006/0271309 A1 Nov. 30, 2006

Related U.S. Application Data

(60) Provisional application No. 60/506,042, filed on Sep. 25, 2003, provisional application No. 60/472,173, filed on May 21, 2003.

(51) Int. Cl.
*G06F 19/00* (2006.01)
*C12N 15/11* (2006.01)
*C12Q 1/68* (2006.01)

(52) U.S. Cl. .............................. 702/19; 536/24.3; 435/6

(58) Field of Classification Search .................. None
See application file for complete search history.

(56) References Cited

U.S. PATENT DOCUMENTS 5,360,715 A 11/1994 Leavitt et al.

OTHER PUBLICATIONS

Raychaudhuri et al. Basic microarray analysis: grouping and feature reduction. Trends in Biotechnology. vol. 19, pp. 189-193 (2001).*
Shoemaker et al. Experimental annotation of the human genome using microarray technology Nature vol. 409, pp. 922-927 (2001).*
Alizadeh et al. Distinct types of diffuse large B-cell lymphoma identified by gene expression profiling Nature vol. 403 pp. 503-511 (2000).*
Golub et al., "Molecular Classification of Cancer: Class Discovery and Class Prediction by Gene Expression Monitoring", Science. Oct. 1999, vol. 286, pp. 531-537, especially p. 531.
Tibshirani, et al. "Diagnosis of Multiple Cancer Types by Shrunken Centroids of Gene Expression", Proc. Natl. Acad. Sci. USA, May 2002, vol. 99, No. 10, pp. 6567-6572, especially p. 6567.
Showe, "Depressed IL-12-mediated signal transduction in T cells from patients with Sézary syndrome is associated with the absence of IL-12 receptor β2 mRNA and highly reduced levels of STAT4", J Immunol, 163(7):4073-4079 (Oct. 1, 1999).
Kari, "Classification and prediction of survival in patients with the leukemic phase of cutaneous T cell lymphoma", J Exp Med, 197(11):1477-1488 (Jun. 2, 2003).
Nebozhyn, "Quantitative PCR on 5 genes reliably identifies CTCL patients with 5% to 99% circulating tumor cells with 90% accuracy", Blood, 107(8):3189-3196 (Apr. 15, 2006 Epub: Jan. 10, 2006).

* cited by examiner

*Primary Examiner*—John S Brusca
(74) *Attorney, Agent, or Firm*—Howson & Howson LLP

(57) ABSTRACT

A method of developing a gene expression profile indicative of the presence or stage of a selected a disease, disorder or genetic pathology in a mammalian subject employs penalized discriminant analysis with recursive feature elimination. A method of diagnosing a cancer in a mammalian subject includes the steps of examining a sample containing the subject's immune cells and detecting a variance in the expression of a statistically significant number of genes, e.g., at least 10 non-tumor genes from those same genes in a characteristic disease or healthy gene expression profile. A significant variance in expression of these genes when compared to a gene expression profile, preferably an average gene expression profile of a normal control, or significant similarities to an average gene profile of subjects with cancer, correlates with a specific type of cancer and/or location of tumor.

20 Claims, 18 Drawing Sheets

METHOD OF DIAGNOSIS OF CANCER BASED ON GENE EXPRESSION PROFILES IN CELLS

CROSS-REFERENCE TO RELATED APPLICATIONS

This application is a national phase of International Patent Application No. PCT/US2004/014521, filed May 21, 2004, which claims the benefit of the priority of U.S. Provisional Patent Application No. 60/506,042, filed Sep. 25, 2003, and U.S. Provisional Patent Application No. 60/472,173, filed May 21, 2003.

STATEMENT REGARDING FEDERALLY SPONSORED RESEARCH OR DEVELOPMENT

This invention was made with government support under Grant Nos. UO1-CA85060 and P30 CA10815-34S3 awarded by the National Institutes of Health. The government has certain rights in the invention.

BACKGROUND OF THE INVENTION

The present invention relates to the diagnosis of cancer, and more specifically to the use of characteristic patterns of gene expression by circulating cells of the immune system and/or circulating cancer cells and/or tumor cells as a method of diagnosis.

Microarrays of several different types have been used to characterize cancer types in patients, most often to distinguish the tissue of origin or a tumor (Ramaswami et al, 2001, *Proc. Natl. Acad. Sci. USA*, 98:15149-54) or original cell type of a leukemia (Golub et al, 1999 *Science*, 218:531-7). In contrast, current practice of cancer diagnosis usually depends on imaging methods, e.g., chest X-rays, histological studies, mammograms, and the like. More recently efforts have been made to detect proteins characteristic of certain cancers in serum, e.g., PSA for prostate cancer.

cDNA arrays have been used to characterize the components of the immune system, as purified cells (Hamalainen, H., et al. 2001 *Genome Biol* 2: RES.0022), as cell lines, as mixtures of peripheral blood mononuclear cells (PBMC) (Alizadeh, A. A., and L. M. Staudt, 2000 *Curr Opin Immunol* 12:219-2255), and in whole blood (Whitney, A. R, et al., 2003 *Proc Natl Acad Sci USA* 100:1896-19016). However most attempts to describe the immune response to cancer, especially tumors, has made use of monoclonal antibodies to characterize the type and differentiation state of B-cells, T-cells, natural killer (NK) cells and dendritic cells, which infiltrate tumors. The reflection of this infiltration is observed by activated cells in the peripheral blood. See, e.g., Fracchia, A., et al, 1987 *Respiration* 51:161-169; Domagala-Kulawik, J., et al., 2001 *Diagn. Cytopathol.*, 25:208-213; Mazzoccoli, G., et al. 1999. *In Vivo* 13:205-209; and Lee, P. P. et al., 1999 *Nat Med* 5:677-6850.

A number of microarray studies have identified genes that appear to be useful for diagnosis of a variety of different cancers. Changes in individual gene products have been reported on tumor infiltrating lymphocytes (TILs) and peripheral blood mononuclear cells (PBMCs) from cancer patients. For example, the loss in colorectal adenocarcinoma patients of the Zeta (signal transducing) chain of the TCR/CD3 complex of T-cells in a tumor-stage specific manner from both TILs and PBLs was reported (Choi, S. H., et al., 1998 *Cancer Immunol Immunother* 45:299-305). The Zeta-associated kinase, p59 fyn, was also reduced in PBMC from patients relative to controls. Numerous receptors have been shown to function in targeting lymphocytes either to skin, on the one hand, or various mucosa on the other. These include the cutaneous lymphocyte antigen (CLA) and chemokine receptors CCR4 and CCR10/CTACK expressed on skin-homing lymphocytes, the integrin a4b7 which directs homing to the gastric mucosa, and integrin a4b1 expressed on lymphocytes which are directed to non-intestinal mucosa such as those of the lungs (see, e.g., Kunkel, E. J., and E. C. Butcher. 2000 *Immunity* 16:1-4). In addition to these T-cell gene products, B-cells have been reported to express different heavy chains depending on their target tissue. NK T-cells, which are associated with the IL-12 dependent rejection of some tumors (Cui, J., et al. 1997 *Science* 278:1623-16263) express different sets of Va and Vb T-cell receptor chains that are associated with homing to different lymphoid organs (e.g. bone marrow, liver, spleen (Eberle, J., et al. 1999 *J Invest Dermatol* 112: 925-9324).

Few of these above-noted microarray studies translate the results to assays suitable for clinical use. For example, a "gene expression ratio" method differentiates patients with mesotheliomas from adenocarcinomas of the lung by using simple ratios of pairs of expressed genes determined by PCR (Gordon, G. J., et al, 2002 Cancer Res, 62: 4963-4967). This method is dependent on being able to identify gene pairs whose differences in expression levels are very highly significant between the 2 tumor types being compared. These types of differences might be expected where the organ or cell-type of tumor origin are different.

Cutaneous T-cell Lymphoma (CTCL), the most common of the T-cell lymphomas, is a non-Hodgkin lymphoma of epidermotropic lymphocytes. Approximately 1500-2000 new cases are reported in the United States each year. Causative roles in the development of CTCL have been suggested for various environmental factors and infectious agents, but the etiology of the disease remains unknown (Li, G et al, *J. Invest. Dermatol.*, 107:308-313; Kim, Y. H., and R. T. Hoppe. 1999 *Semin Oncol*, 26:276-289). CTCL is characterized by the accumulation of malignant cells with a low mitotic index, suggesting that the regulatory defect allowing these cells to accumulate may reside in the apoptotic pathways (Dereure, O., et al, 2000 *Brit. J. Dermatol.* 143:1205-1210; Edelson, R. L. 2001 *Ann N Y Acad Sci* 941:1-11). Mycosis fungoides (MF) and Sezary syndrome (SzS) are the two major clinical variants of CTCL (Kim, Y. H. and Hoppe, R. T. 1999 *Semin Oncol*, 26: 276-289 (Kim III); Kim, Y. H. et al, 1996 *Arch. Dermatol.*, 132: 1309-1313 (Kim II); and Diamandidou, E. et al. 1996 *Blood*, 88: 2385-2409).

MF is skin associated and progresses through increasing cutaneous, and finally organ involvement. Although treatable in early stages, MF is frequently misdiagnosed because of similarities to more benign forms of skin disease. Even with early diagnosis, 10% of MF patients who present with limited disease and about 25% of those with extensive patches or plaques will develop progressive disease, eventually succumbing despite extensive therapy (Kim I; Kim, et al 1999 *Arch Dermatol* 135:26-32 (Kim IV). SzS, a leukemic and erythrodermic variant of CTCL, is characterized by the presence of circulating lymphocytes with atypical cerebriform nuclei (Sezary cells) in the skin, lymph nodes, and peripheral blood. It is a more aggressive form of CTCL, which is associated with a poor prognosis and with a mean survival of three years from the time of diagnosis. Immunophenotyping and genotyping of Sezary cells indicates that they arise as a clonal expansion of mature helper memory T-cells (Dereure, cited above and Edelson, cited above). They express cytokines characteristic of T-helper type 2 (Th2) cells, including IL-4, IL-5, and IL-10 (Dummer, R., et al, 1996 *Blood* 88:1383-1389; Nickoloff, B. J., et al, 1994 *Clin Immunol Immunopathol* 73:63-68; Rook, A. H., et al 1993 *Arch Dermatol* 129:486-489) and fail to express Th-1 cytokines, IL12, and IFN-γ (Vowels, B. R., et al., 1994 *J Invest Dermatol* 103:669-673). Patients with MF can have blood findings typically observed in SzS, and in rare cases MF can evolve into SzS, confirming a close relationship between the two conditions.

In both MF and SzS, early detection and treatment is directly correlated with outcome (Duvic, M. *Clin Lymphoma*, 1 Suppl 1: S15-20, 2000; Foss, F. M. 1 Suppl 1: S9-14, 2000; Kim, Y. H. et al, *Arch Dermatol,* 131: 10031008, 1995 (Kim 1). However, although CTCL is readily treatable in early stages, this relatively rare cancer can be difficult to diagnose because of similarities to a variety of benign skin diseases and frequently goes undetected for years. Therapies using biological response modifiers, such as extra-corporeal photopheresis and IFN-α, have improved survival of patients with SzS (Rook, A. H et al, 1999 *J Investig Dermatol Symp Proc* 4:85-90; Gottlieb, S. L et al., 1996 *J Am Acad Dermatol* 35:946-957). However, 50% of patients who present with advanced disease do not respond to therapy and 25% of those that respond initially will relapse and progress to fatal disease. There are presently no well-defined clinical markers for CTCL that permit an early identification of patients most likely to develop progressive disease.

There remains a need in the art for novel methods using gene expression as a useful diagnostic method for cancer, and in particular, for a more efficient and inexpensive method for detecting the presence of cancer in a normal population for purposes of screening, as a replacement for diagnostic imaging.

SUMMARY OF THE INVENTION

The present invention meets the need in the art, because it relates to the detection of cancer in a subject, e.g., a nominally healthy subject, to staging of cancer in a subject with advanced disease, and/or to determination of the tissue or origin of such a cancer, and more specifically to the use of characteristic patterns of gene expression by cells as a method of diagnosis.

In one aspect, the invention provides a method of developing a gene expression profile indicative of the presence or stage of a selected a disease, disorder or genetic pathology in a mammalian subject. The method involves the analysis of an array of gene expression levels from a biological sample of one or more subjects having the disease in question by applying penalized discriminant analysis and recursive feature elimination steps to the array. A gene expression profile is thereby obtained that is a characteristic of the selected disease, disorder or genetic pathology or a stage of the selected disease, disorder or genetic pathology. The characteristic profiles may then be used in individual patient diagnostic assays.

In another aspect, the invention provides a method of diagnosing a disease, disorder or pathology, such as a cancer characterized by a solid tumor, and/or monitoring the effect of treatment of such cancer, in a mammalian subject. This method involves examining a biological, e.g., peripheral blood, sample containing circulating immune cells or cancer cells of the subject and obtaining a first profile of a plurality of genes and comparing same to a gene expression profile, such as described above for certain cancers, and/or to a second profile of the genes from a healthy subject or from a subject with another disease. In another aspect, the invention provides a method of diagnosing a cancer characterized by circulating cancer cells and/or monitoring the effect of such cancer treatment in a mammalian subject. This method involves examining a sample containing circulating cancer cells or tumor cells of the subject and detecting a characteristic profile of variance in the expression of a statistically significant number of genes using the steps described above. Variance in expression of these genes compared to expression of the same genes in a normal control correlates with the type and/or location of the cancer.

In another aspect, the invention provides a method of identifying the effects of a therapeutic agent or regimen on a patient having a cancer, such as described above. The method comprises administering the therapeutic agent or treatment regimen to the patient. Periodically during and after administration of the agent or regimen to the patient, another sample containing immune cells and/or circulating cancer or tumor cells of the patient is examined using the steps described above and arrays are prepared of genes that are then compared to a characteristic expression profile for that disease or stage of disease/therapy. The patient's expression profile can also be then compared to the same profile obtained from the patient prior to the administration. Optionally, the current expression profile is compared to a control profile from a healthy subject. Detection of a variance in expression of the genes in the current profile from the prior profile or from the normal control indicates the level of efficacy of the agent or regimen.

In yet another aspect, the invention provides a method of identifying a cancer therapeutic agent or regimen useful for the treatment of a cancer. This screening method comprises the steps of administering the therapeutic agent or treatment regimen to a test mammalian subject. Periodically during and after administration of the agent or regimen, another sample containing immune cells and/or cancer cells of the subject is examined using the steps described above and a current expression profile of a statistically significant number of genes is obtained. The current profile is compared to gene expression profiles for that disease or stages or that disease, as well as to the same profile obtained from the subject prior to the administration and optionally to a control profile from a healthy subject. Detection of a variance in expression of the genes in the current profile from the prior profile and to the characteristic profile, which variance is closer to the profile of the normal control, indicates that the agent or regimen is a desirable cancer therapeutic for the cancer.

In still another aspect, the invention provides a method for determining the response of an individual patient to a therapeutic agent or regimen by employing the above-described methods.

In still further aspects of this invention, certain gene profiles characteristic of certain diseases are provided.

In yet a further aspect, the invention provides a method for diagnosing, staging or monitoring a cutaneous T cell lymphoma (CTCL). This method involves detecting in a biological sample, e.g., peripheral blood, the level of one or more significant genes, which exhibit variant expression from its expression in a normal sample. In one embodiment, this aspect involves detecting the variant expression of at least two of five specific genes. In another embodiment, the method involves detecting the variant expression of five specific genes. In still additional embodiments, this method of the invention involves detecting variant expression of 10 or more than 10 variant genes from their respective expression in a normal sample.

In yet another aspect, the invention provides a non-naturally occurring or purified ligand that binds to plastin tissue protein (PL3) within one of two specifically identified epitope sequences. In one embodiment, the ligand is an antibody. In another embodiment, the ligand is associated with a detectable label or label system.

In still another aspect, the invention provides a method for diagnosing CTCL in a sample comprising contacting said sample with a ligand of PLS3 and detecting the presence of the ligand in the sample.

In yet a further aspect, the invention provides a kit for diagnosis of CTCL in a mammalian patient comprising a ligand of plastin T and a detectable label or label system Other aspects and advantages of the present invention are described further in the following detailed description of the preferred embodiments thereof.

DETAILED DESCRIPTION OF THE INVENTION

Figures 1A, 1B:
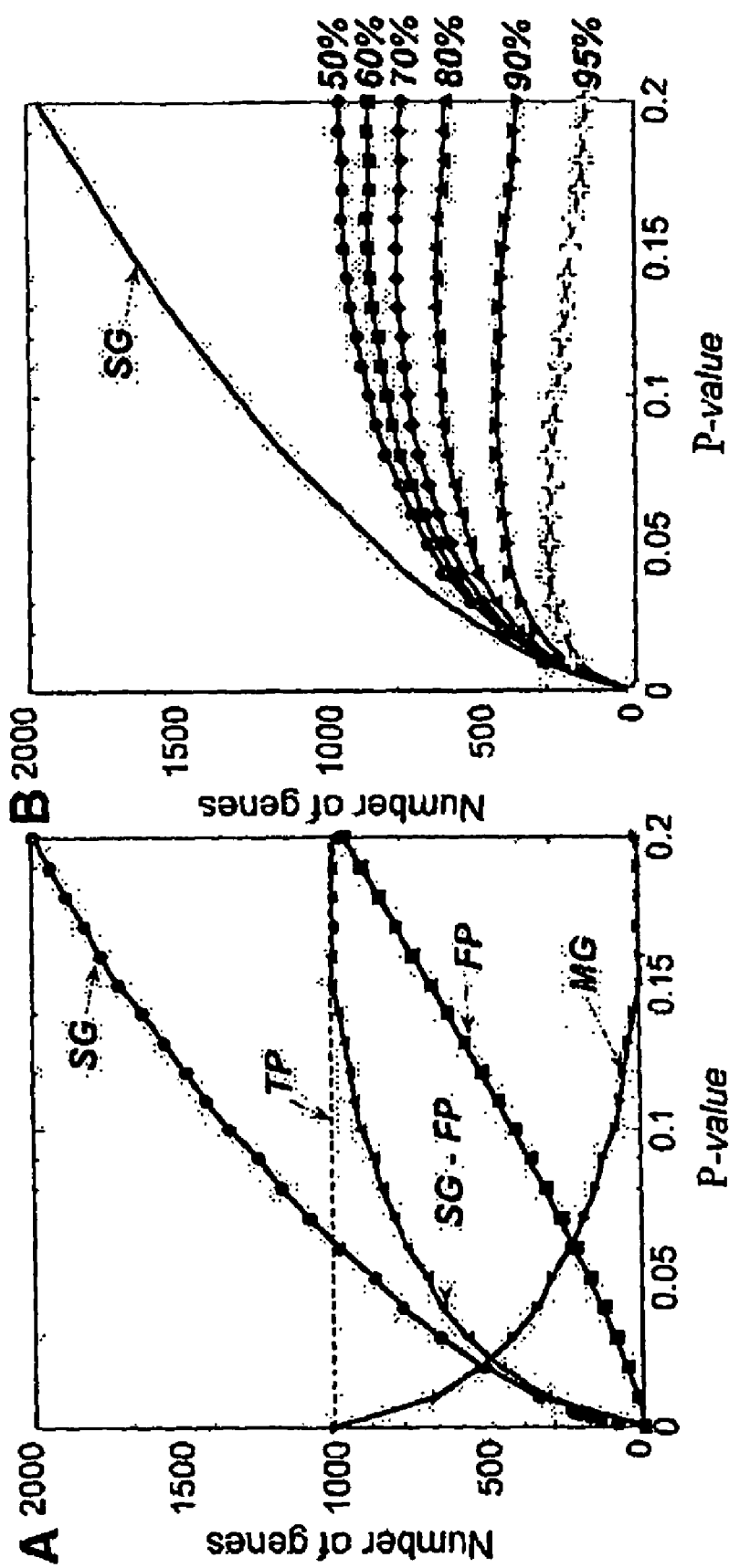
FIG. 1A is a graph showing genes differentially expressed by t-test in PBMC from SzS patients compared to Th2 controls. Significant genes (SG) were detected at each p-value. False positives (FP) were estimated by permuting the sample labels 10,000 times (SG-FP). Estimates of the number of true positives are indicated by TP. The "true positive" curve attains a maximum value of 1000, suggesting that a significant number of differentially expressed genes are present at p-values>0.01. The number of missed genes, (MG, defined as 1000-TP) is less than 100 at p=0.10.
FIG. 1B is a graph showing the number of observed significant genes corrected by the maximum number of significant genes found in permuted data as a function of p-value cutoff and percentile of the permutations.

The present invention answers the need in the art by providing novel methods for diagnosis of cancers based on gene expression profiling.

In one embodiment, the invention provides a method of developing a gene expression profile indicative of the presence or stage of a selected a disease, disorder or genetic pathology in a mammalian subject. The method involves the analysis of an array of gene expression levels from a biological sample of one or more subjects having the disease in question by applying penalized discriminant analysis and recursive feature elimination steps to the array. The recursive feature elimination identifies and eliminates the least informative up-regulated and down-regulated genes from the first profile. These steps are optionally repeated until a gene expression profile is obtained containing statistically significant number of genes that vary in expression from the expression of the same genes in the array of the healthy or disease control. This gene expression profile is a characteristic of the selected disease, disorder or genetic pathology or a stage of the selected disease, disorder or genetic pathology. The profile of variance in expression of the genes compared to a normal control or to a disease control correlates with the type and/or location of the disease, disorder or genetic pathology. For example, variance in expression of these genes compared to expression of the same genes in a normal control correlates with the type and/or location of the cancer. One such cancer is cutaneous T cell lymphoma (CTCL). This characteristic profile may then be used in individual patient diagnostic assays.

In one embodiment according to this method, the gene expression profiles of the immune cells circulating in the peripheral blood of cancer patients reflect the presence of a solid tumor. Preferably, for cancers characterized by solid tumors, the genes examined for the profiles are genes normally expressed by the patients' immune cells. For cancers in which the tumor or cancer cells circulate in the peripheral blood, e.g., CTCL, the genes examined fro the profiles are genes on the cancer or tumor cells themselves. Each profile is sufficiently specific to indicate the type and location of the cancer or tumor. In some embodiments, this characteristic gene expression is detectable earlier than any other sign of tumor presence. Gene expression profiling of peripheral blood samples thus is a powerful tool for cancer diagnosis and staging, as well as the monitoring of therapeutic efficacy.

A. DEFINITIONS

"Patient" or "subject" as used herein means a mammalian animal, including a human, a veterinary or farm animal, a domestic animal or pet, and animals normally used for clinical research.

"Sample" as used herein means any biological fluid or tissue that contains immune cells and/or cancer cells. A suitable sample for use in this invention, whether the cancer is a solid tumor cancer or a cancer characterized by circulating cancer cells, includes peripheral blood. Other useful biological samples include, without limitation, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a patient having cancer. Such samples may further be diluted with saline, buffer or a physiologically acceptable diluent. Alternatively, such samples are concentrated by conventional means.

"Immune cells" as used herein means B-lymphocytes, T-lymphocytes, NK cells, macrophages, mast cells, monocytes and dendritic cells.

As used herein, the term "cancer" means any cancer. In one embodiment, the cancer is characterized by the presence of a solid tumor. Among such cancers are included, without limitation, breast cancer, neuronal cancer, prostate cancer, pancreatic cancer, brain cancer, melanoma, other skin cancers, esophageal cancer, colorectal cancer, ovarian cancer, small cell carcinoma, adrenal cancer, lung adenocarcinoma, mesothelioma, Hodgkins lymphoma and non-Hodgkins lymphoma without blood involvement. In another embodiment, the cancer is characterized by the presence of circulating cancer cells in the peripheral blood, e.g., CTCL, T-ALL, B-ALL, CML, CLL, APL, AML, B-CLL, or hairy cell leukemia. Suitable cancers for diagnosis or screening with the methods described below include early stage cancers or late stage cancers.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, etc.

By "non-tumor genes" as used herein is meant genes which are normally expressed in other cells, preferably immune cells, of a healthy mammal, and which are not specifically products of tumor cells.

The term "statistically significant number of genes" in the context of this invention differs depending on the degree of change in gene expression observed. The degree of change in gene expression varies with the type of cancer and with the size or spread of the cancer or solid tumor. The degree of change also varies with the immune response of the individual and is subject to variation with each individual. For example, in one embodiment of this invention, a large change, e.g., 2-3 fold increase or decrease in a small number of genes, e.g., in from 5 to 8 characteristic genes, is statistically significant. This is particularly true for cancers without solid tumors. In another embodiment, a smaller relative change in about 30 or more genes is statistically significant. This is particularly true for cancers with solid tumors. Still alternatively, if a single gene is profiled as up-regulated or expressed significantly in cells which normally do not express the gene, such up-regulation of a single gene may alone be statistically significant. Conversely, if a single gene is profiled as down-regulated or not expressed significantly in cells which normally do express the gene, such down-regulation of a single gene may alone be statistically significant. As an example, a single gene, which is expressed about the same in all members of a population of patients, is 4-fold down regulated in only 1% of individuals without cancer. Four such independently regulated genes in one individual, all 4 fold down-regulated, would occur by chance only one time in 100 million. Therefore those 4 genes are a statistically significant number of genes for that cancer. Alternatively, if normal variance is higher, e.g., one healthy person in 10 has the gene 4-fold down-regulated, then a larger panel of genes is required to detect variance for a particular cancer.

Thus, the methods of this invention contemplate examination of the expression profile of a "statistically significant number of genes" ranging from 1 to 100 genes in a single profile. In one embodiment, the gene profile is formed by a statistically significant number of at least 1 gene. In another embodiment, the gene profile is formed by a statistically significant number of at least 4 genes. In still another embodiment, the gene profile is formed by at least 10 genes. In still other embodiments, the gene profiles examined as part of these methods, particularly in cases in which the cancers are characterized by solid tumors, contain, as statistically significant numbers of genes, 20, 30, 40, 50, 60, 70, 80, or 90 genes in a panel.

The terms HA-01 through HA-06 refer to microarrays of known genes. These microarrays are publicly available and sold by the Genomics facility of The Wistar Institute, Philadelphia, Pa. The lists of the genes forming these microarrays and means for ordering the arrays are published on the internet at (http://www.wistar.upenn.edu/researchfacilities/facilities/genomics/review.html). However, one skilled in the art may readily reproduce such microarrays by use of the sequences of the genes, all of which are publicly available from conventional sources, such as GenBank.

B. GENE EXPRESSION PROFILE AND USE IN DIAGNOSTIC METHODS

According to the present invention, there is provided a method of diagnosing a cancer in a mammalian subject. Since the body is under continuous surveillance by the immune system for evidence of infection or aberrant cells (Dunn, G. P., et al., 2002 *Nat Immunol* 3:991-998.), a sampling of immune cells from the peripheral blood, properly analyzed, can be used to diagnose any condition which is detected as abnormal, including cancer. Expression profiling from non-tumor cells in peripheral blood is useful as a diagnostic tool for cancer detection, because there are effects of cancer cell or tumor growth on gene expression of various classes of immune cells found in the peripheral blood, and the effects have sufficient specificity for cancer or tumor type to indicate, e.g., the localization of the tumor if it has not metastasized to multiple sites or the stage of cancer, if metastatic. Similarly, expression profiling using circulating cancer cells from peripheral blood is useful as a diagnostic tool for cancer detection, because there are effects of cancer cell or tumor growth directly expressed on the cancer cells or tumor cells themselves.

A method of developing a gene expression profile indicative of the presence or stage of a selected a disease, disorder or genetic pathology in a mammalian subject includes the following steps. A first array of expression levels of a plurality of genes obtained from a biological sample of one or more patients having the disease, disorder or genetic pathology in question is assembled by conventional means. Preferably, the sample contains immune cells or cancer cells. Expression of the genes is analyzed in comparison to expression of the same genes in a second array of genes obtained from the same source of biological tissue or fluid from one or more healthy controls or from one or more patients having a different disease, disorder or genetic pathology that the one in question.

Penalized discriminant analysis is applied to the first array by comparison to a second array of expression levels of a plurality of genes. PDA is an extension of Fisher's linear discriminant analysis, which allows analysis of problems in which the number of variables greatly exceeds the number of examples. So, PDA is well adapted to microarray analysis. PDA is described, e.g., in Hastie, T., et al, 1995 *Annals of Stats.*, 23:73-102. This analysis is coupling with recursive feature elimination. Recursive feature elimination is applied to the first array to identify and eliminate the least informative up-regulated and down-regulated genes from the comparison. In every comparison or analysis, a number (preferably an equal number) of the least informative up-regulated and down-regulated genes are eliminated from the profile, which is then analyzed. For example, genes in excess of 800 are reduced in increments of 100 to 800 genes. From 800 to 400, the decrement is 20 genes, and from 400 to 2, the decrement is 2 genes. Shrunken centroids are used to determine whether any known classes of the disease or disorder in question have a distinct expression profile. Shrunken centroid analysis is a new univariante algorithm for multiclass classification recently described by Tibshirani, R., et al., 2002 *Proc Natl Acad Sci USA* 99:6567-6572. The resulting class is compared separately to controls and samples from patients with other types of cancer in subsequent analyses using PDA. The addition of recursive feature elimination to PDA is preferably included in the program for PDA so that this analysis is performed automatically.

These steps are optionally repeated until a gene expression profile for the disease in question containing a statistically significant number of genes that vary in expression from the expression thereof in the array of said healthy or disease control, is obtained. This gene expression profile is a characteristic of the selected disease, disorder or genetic pathology or a stage of said selected disease, disorder or genetic pathology. PDA with recursive feature analysis is a technique that to Applicants' knowledge has not previously been applied to the evaluation or diagnosis of disease.

It is anticipated that this process can work similarly to generate characteristic gene expression profiles for disorders including cancer, and any genetic pathology that is diagnosed by characteristic variances in gene expression.

In other embodiments of the methods of this invention, one can employ other known techniques to develop the expression profile of certain genes normally expressed in immune cells or in cancer cells. Transcription profiling using cDNA microarrays collects information about the expression level of thousands of genes and is an extremely sensitive method for distinguishing between cell types or between different differentiation states or physiological states of the same cell type. See, e.g., Khan, J et al., 2001 *Nat Med* 7:673-679; Golub et al, cited above; Hamalainen et al, cited above. Another useful method for establishing an expression profile is the use of support vector machines analysis.

In one embodiment, this method involves examining a sample containing immune cells of the disease subjects to obtain a gene expression profile of a statistically significant number of non-tumor genes in the immune cells. Preferably, as described above, an embodiment of this method results in an expression profile involving the expression characteristics of at least four non-tumor genes. In other embodiments, an expression profile involves characteristics of more than 30 genes. Still other statistically significant numbers of genes of greater than 50 may form a profile as described above.

The number and identity of the statistically significant genes associated with a particular type or location of a tumor accurately and sensitively assign a new patient to a class (diseased or healthy). See, for example, the genes listed immediately below and in the following Tables 1 and 11-15, among others. Statistically significant variances in the expression profiles of the patient from those of the normal/diseased profiles correlate with a cancer type and/or location of a solid tumor.

Uses of the methods of this invention are described in detail in the examples below. These methods and results for an exemplary immune cell cancer, cutaneous T cell lymphoma, as well as for exemplary solid tumor cancers, such as lung cancers are summarized below. These gene expression profiles may then be employed in diagnosis, staging and therapy monitoring of specific individual patients.

Another embodiment of this invention includes a method of diagnosing or staging a disease, disorder or genetic pathology in a mammalian subject. The steps of such a diagnostic method include comparing the expression of a statistically significant number of genes obtained from a biological sample of the individual subject containing immune cells or cancer cells and to a gene expression profile characteristic of the selected disease, disorder or genetic pathology or a stage of the selected disease, disorder or genetic pathology and to a gene expression profile from a similar biological sample of a healthy subject. Variance in the expression of genes in the patient sample from those of the characteristic gene expression profiles is analyzed. Variance in expression of patients' genes compared to a normal control and similarly to the characteristic gene expression profile correlates with the type and/or location of the disease, disorder or genetic pathology.

For example, a profile established for the patient sample in question is compared with characteristic immune cell gene expression profiles or profiles of gene expression from other tissue from a number of normal, healthy control subjects and from subjects with known diseases. The detection algorithm of the method employed compares the profile of the new patient with that of the average healthy/diseased profiles previously established and returns a mathematical value or score reflecting which population the new patient most closely resembles.

Such characteristic gene expression profiles may desirably be included in diagnostic kits for the diseases or disorders in question.

1. Non-Solid Tumor Profiles, i.e., CTCL

Expression profiles for diagnosis of cancers in which cancer cells are found in the peripheral blood can be generated by the methods of this invention. Thus, in another embodiment of this invention as supported in Examples 1-6 below, cDNA microarrays were used to study gene expression patterns in patients with a selected cancer that is not characterized by solid tumors, i.e., Sezary Syndrome, the leukemic form of cutaneous T-cell lymphoma (CTCL). These cDNA microarrays identified markers useful for diagnosis and prognosis and provided new targets for therapy. Specifically, the method of this invention identified gene expression profiles in peripheral blood mononuclear cells that could diagnose patients with leukemic forms of cutaneous T-cell lymphoma, primarily Sezary syndrome.

Gene expression profiles of peripheral blood mononuclear cells (PBMC) from patients with the high numbers of circulating Sezary cells were analyzed using cDNA arrays.

a. Selection of Significant Genes.

The analysis of gene expression in patients with high Sezary cell counts was compared to Th2 skewed PBMC control cells from healthy volunteers. Th2 skewed PBMC was used as the standard for comparison because of the overwhelming evidence of the Th2 nature of Sezary cells. In this way, the detection of differences, which were related to Th2 differentiation, rather than the development of CTCL, was minimized. Patients were tested against 4500 unique genes. In comparing Th2 skewed controls to patients, significant changes in gene expression are found for less than 10% of the genes on the arrays. A comparable number of changes are found (data not shown) when comparing normal PBMC to PBMC skewed to a Th1 or Th2 response, suggesting very few events are required to alter expression of so many genes. Nevertheless, the changes in expression observed account for many of the observed characteristics of the disease, provide markers for diagnosis, and prognosis and may also provide targets for therapy.

A univariante t-test was used as a primary screen to determine the number of genes that are differentially expressed between the high Sézary cell patients and Th2 skewed controls. Two thresholds of significance were used for the different analyses (Allison, D. B., et al 2002 *Computational Statistics and Data Analysis* 39:1-20). Because of patient variability, the most accurate class distinctions between patients and controls or early and late-stage disease must be based on expression levels of many genes. When expression data for patients with high blood tumor burden (Sezary cells>60% of the lymphocytes) and healthy controls were compared by t-test, at p<0.01, 385 genes were differentially expressed. The genes selected at the p<0.01 threshold included few false positives, exhibited low variance among patients, and were likely to be the most useful for understanding the biology of CTCL and for designing single-gene diagnostic reagents.

Numerous genes with p>0.01 that were informative as a group, even though their individual variability was high.

Using penalized discriminant analysis (PDA) (Hastie, T et al, 1995 *Annals of Statistics* 23:73-102; Raychaudhuri, S. 2001 *TIBS* 19:189-193), trained on patients with high Sezary cell counts, several small groups of genes were identified that were able to accurately classify patients with high tumor burden (60-99% of circulating lymphocytes) from normal controls with 100% accuracy.

When patients with lower tumor burden (5-62% of circulating lymphocytes) were tested according to this method, a panel of 8 genes was identified that can correctly distinguish Sezary syndrome in patients with as few as 5% circulating tumor cells from normal controls with 100% accuracy. These results suggest that even in early disease, Sezary cells produce chemokines and cytokines that induce an expression profile in the peripheral blood distinctive to Sezary syndrome. The ability to identify patients with as few as 5% circulating Sezary cells using PDA suggests that the malignant cells, as a function of the cytokines and chemokines they release, induce a pattern of gene expression in the peripheral blood that is distinctive to CTCL.

b. Expression of Genes Associated with Th2 Differentiation.

The array studies confirmed and extended evidence of the skin homing and Th2 nature of Sezary cells. Highly overexpressed genes required for Th2 differentiation included Th2 specific transcription factors Gata-3, which also suppresses Th1 development (Grogan, J. L., et al., 2001 *Immunity* 14:205-215; Rao, A., and O. Avni. 2000 *Br Med Bull* 56:969-984), and JunB required for Th2 specific IL-4 transcription (Li, B., et al., 1999 *Embo J* 18:420-432). Amplification and overexpression of JunB was recently described in a subset of CTCL patients (Mao, X., et al. 2003 *Blood* 101:1513-1519).

Other highly overexpressed genes included genes that are important for tissue specific homing characteristic of Th2 cells, such as selectin-L ligand, preferentially found on CD4+ cells expressing Th2 cytokines (Kannagi, R. 2000 *Seikagaku* 72:1399-1415); selectin-P ligand, which forms the skin homing cutaneous lymphocytic antigen (CLA-1) when modified by alpha-fucosyl transferase (Pober, J. S., et al. 2001 *Ann NY Acad Sci* 941:12-25); and integrin β-1 (Jaspars, L. H., et al. 1996 *J Pathol* 178:385-392; Clissi, B., et al., 2000 *J Immunol* 164:3292-3300), another marker for skin-homing T-cells. Still other highly overexpressed genes included proteoglycan 2, the RhoB oncogene, and dual-specificity phosphatase-1.

Highly underexpressed genes included CD26, Stat-4 and the Interleukin 1 receptors.

c. Genes that Affect Apoptosis.

There has been much speculation that CTCL cells are defective in their apoptotic pathways. However, observations at the message level from the array studies are not, in all cases, consistent with this hypothesis. The antiapoptotic gene Bcl2 was underexpressed in the samples. Additionally, although Fas ligand message levels were decreased, T-cell associated Fas message levels were essentially unchanged. Several other patterns of gene expression that contribute to a defect in the apoptotic pathways were found.

The overexpression of the proinflammatory cytokine IL-1β, a primary activator of T-cell death pathways (Luft, T., et al, 2002 *J Immunol* 168:713-722), and Caspase 1 required for IL-1β activation, was unexpected in light of the primarily anti-inflammatory phenotype exhibited by patients. However, IL-1β overexpression is offset by the significant underexpression of both IL-1 receptors (IL-1Rs) in patients, suggesting this important apoptotic pathway is inactive in CTCL cells. The significance of the underexpression of the IL-1Rs to CTCL is supported by PDA studies that identify the reduction in IL-1R expression as second only to that of STAT4 in classifying patients and controls.

The chemokine receptor CX3CR1 is normally expressed on Th1 but not on Th2 T-cells (Fraticelli, P., M. et al, 2001 *J. Clin. Invest.* 107:1173-1181), yet it was overexpressed by more than 4-fold in patients. In the CNS, CX3CR1 on microglia is suggested to prevent Fas mediated cell death in response to stress (Boehme, S. A., et al, 2000 *J Immunol* 165:397-403). If CX3CR1 has a similar function in Sezary cells, this could also contribute to the proposed apoptotic defect in these cells. ICAM 2, also overexpressed, has been shown to suppress TNF-α and Fas-mediated apoptosis through its activation of the PI3K/AKT pathway (Perez, O. D., et al, 2002 *Immunity* 16:51-65). AKT overexpression has been associated with a variety of different cancers. The combined up-regulation of genes known to interfere with apoptosis, such as CX3CR1 and ICAM2, and down-regulation of the IL-1R's contributes to the observed resistance to apoptosis in Sezary cells.

d. Genes not Normally Expressed in Th2 T-Cells.

There are presently no CTCL specific markers. Identification of genes expressed in the malignant T-cells, which are not normally expressed in that cell type can be very useful for diagnosis and perhaps act as targets for intervention. The plastin gene family has three known members that function as actin bundling proteins and have tissue restricted expression patterns (Namba, Y., et al, 1992 *J Biochem (Tokyo)* 112:503-507), i.e., Plastins 1, 2 and 3, also known as Plastins L, I and T, respectively that are highly conserved in sequence. Tissue plastin (PLS3) is expressed in a variety of tissues but not in normal lymphoid cells that express lymphoid cell plastin (LCP1) instead.

In the present invention, the cDNA microarrays detected message for plastin-T, not normally expressed in lymphoid tissue, only in patient samples. LCP1 was abundantly expressed in both patients and controls, but inappropriate PLS3 expression is restricted to the CTCL samples. PLS3 expression was detected in 35 of the 45 patient samples surveyed by arrays. Both lymphoid and tissue plastins were co-expressed in all cases. Transfection studies have suggested that these highly related proteins have differences in localization patterns and in their interactions with cytoskeletal accessory proteins and therefore may have somewhat different functions (Arpin, M., et al. 1994 *J Cell Biol* 127:1995-2008).

The inappropriate expression of a non-lymphoid marker, such as PLS3, and a non-Th2 marker, such as CX3CR1, in the malignant cells are thus useful as robust markers for diagnosis. Thus the present invention further presents these genes as new single gene markers for diagnosis of CTCL. Ligands that bind specifically to tissue plastin (PLS3) are presented below as new diagnostic reagents for diagnosis of CTCL according to this invention. These ligands can identify the presence of PLS3, even in the company of other plastin forms.

e. Genes that have High Predictive Power to Classify Patients and Controls.

The loss of STAT4 expression in CD4+ Sezary cells was noticed in a small group of patients (Showe, L. C., et al., 1999 *J Immunol* 163:4073-4079), and further observed in the 45 patient samples analyzed in the examples below. The loss of expression of Stat-4, which is required for Th1 T-cell differentiation (Frucht, D. M., et al. 2000 *J Immunol* 164:4659-4664; Fukao, T. et al., 2001 *J Immunol* 166:4446-4455), is one of the most significant characteristics of CTCL patent samples. STAT4 is one of two genes that can be used in PDA to classify high Sezary cell patients from controls by themselves and one of eight genes that classify patients with low percentages of circulating Sezary cells, suggesting that the loss of STAT4 is an early event in the development of CTCL.

The small GTPase, RhoB is another of the top classifiers identified in the PDA studies. Like PLS3, RhoB interacts with the actin cytoskeleton. As a GTP binding protein RhoB has the capacity to modulate downstream events, and its activity is dependent on post-translational modifications that can be catalyzed by either farnesyl transferases or geranyltransferases. Farnesyl transferase inhibitors have been under intense scrutiny for their potential in treating cancers that harbor Ras mutations. Although there are some observations that contradict the model (Namba, Y. et al., 1992 *J Biochem (Tokyo)* 112:503-507), there is a large body of evidence that supports the hypothesis that the efficacy of these inhibitors in treating cancers is due to their effects on RhoB (Crul, M., et al. 2001 *Anticancer Drugs* 12:163-184; Prendergast, G. C. 2001 *Nature Rev Cancer* 1:162-168; Sebti, S. M., and A. D. Hamilton. 2000. *Expert Opin Investig Drugs* 9:2767-2782).

Although the high Sezary cell patients and controls were classified with as few as two genes, STAT4 and RhoB, biomarkers that could identify patients with low tumor burdens that are more difficult to recognize clinically were also identified. When the classification gene set was reduced to the twenty top genes, all controls and all but one patient were properly classified. On reexamination, the misclassified patient had skin findings typical of Kimura's disease (Lichter, H., et al., 1998 *Harefuah* 134:760-762, 832) but blood findings in keeping with leukemic phase CTCL including a high $CD4^+/CD8^+$ ratio, eosinophilia, and a circulating T-cell clone identified by a chromosomal abnormality. Despite the many similarities to SzS, this Kimura's patient was properly identified by PDA. Expression patterns of Stat-4 and RhoB alone could be used to correctly classify 26 of the 29 CTCL patients and all but one untreated control, but there are many sets of ten genes that are as good as or better classifiers than these two genes.

f. Classification of Short Term Survivors.

Patients who are ST survivors, and are usually resistant to additional therapy, have a detectably different gene expression pattern from patients classified as MT and LT survivors, independent of their tumor burden. PDA was used to identify expression patterns of 10 genes, which distinguish patients with short survival times (i.e., who will succumb within six months of sampling), regardless of the blood tumor burden when they were sampled. Thus, diagnosis of an advanced stage of Sezary syndrome is possible by monitoring expression patterns of these 10 genes by microarray analysis of tumor or blood samples in a clinical setting.

The finding of a "terminal signature" in these patients has a number of implications. Perhaps the most obvious and important is that an accumulation of a high percentage of Sezary cells is not an optimal index of the severity of disease. Since CTCL patients may die from a number of different causes, it is striking that a characteristic gene expression pattern can be detected in their peripheral immune cells when death is imminent. This pattern is useful in identifying patients who might benefit from more aggressive therapies that would otherwise not be recommended until later times.

In another specific embodiment of this invention disclosed in the examples below, a simple and reliable method for diagnosis of SzS is disclosed using quantitative real time PCR (qPCR) measurements and linear discriminant analysis (LDA). For simplicity, this procedure is referred to as DAPD (Discriminant analysis of quantitative PCR (qPCR) data). Because LDA assigns a predictive score to each classified sample, a confidence level is associated with each result making this approach robust and simple to apply. Using expression levels of STAT4, Cd1d, GATA3, TRAIL and PLS3 in purified PBMC, CTCL patients are diagnosed with 95% accuracy, including those with as few as 5% circulating malignant cells. Detection of PLS3, normally not expressed in lymphoid cells, is by itself diagnostic for 70% of the patients tested.

This invention thus provides a composition and method of diagnosis that is effective for identifying early disease. Such a method/assay must be able to accurately diagnose patients with very few tumor cells as well as those with high tumor burden. In developing the diagnostic method, 4 different criteria were met. First, the material to be assayed is easily accessible. Second, the technology is robust and can be easily applied at different locations. Third, the false positive and false negative calls are low; and fourth, the classification gives a measure of the accuracy of diagnosis.

Successful diagnosis based on the expression of just a few genes is made possible in this invention by identifying the best discriminant genes from 5800 genes analyzed in microarray experiments, and by the showing that the results are replicable using two different methodologies, i.e., microarray and qPCR, with the same accuracy (FIGS. 1A-1F). The present invention's diagnostic method is a platform independent, discriminant method. Instead of using the calculated gene expression values, which can be different for different methods and might vary from one clinical setting to another, the relative ranks of gene expression are used in this method. By using the ranks of gene expression, the analysis is remarkably robust. It is also method independent, in the sense that genes selected by microarrays of amplified RNA can be used to diagnose by PCR using total RNA. The discriminant function itself is transferable from one method to another, if a calibration standard is employed.

As shown in the examples below, for the selected genes, LDA trained on datasets acquired either by arrays or PCR and using either aRNA or total RNA produce virtually identical classification of the test sets. As a result, analysis of patient samples does not require that the "training set" be performed on the same platform, although a single sample should be carried from one platform to the next to standardize the gene ranks. LDA using gene ranks was 99% accurate on the data of Gordon et al, cited above with 4 genes, and 100% accurate with 5 genes. The ratio-based method of Gordon et al was 95% and 99% percent accurate respectively on the same data.

An additional positive characteristic of the DAPD classification method of the present invention is that each sample receives a quantitative score that is a measure of its quality of classification by the genes being tested. Although only five genes were used in the examples, that number is increased to further characterize patients that appear to be close to the cut-off. The set of five genes used in the examples for diagnosis of CTCL is not the only possible classifier. The array studies identified several small sets of genes that were equally good at classifying patients and control samples, and are equally good at diagnosis by DAPD. It is anticipated that because of the known relationship between MF and SzS, genes identified in these examples may also be useful in the diagnosis of MF, the most frequently misdiagnosed form of CTCL.

Thus, use of the methods of this invention permit early diagnosis of CTCL and staging of terminal CTCL by monitoring expression patterns of a small number of genes by microarray analysis of tumor or blood samples in a clinical setting. These methods and the results obtained thereby are described in detail in the following examples.

The following Table 1 provides an additional list of genes significant for use in the methods of this invention and for which the PDA with recursive feature elimination technique can be applied, as described herein. The gene names and symbols are indicated. All of these genes are upregulated. Table 1, Column A lists the genes in order of significance for diagnosis of CTCL, i.e., the best classifiers of CTCL by PDA according to this invention. Column A lists the genes in ratio of gene expression in purified CTCL tumor cells to expression in the corresponding normal cells (i.e. CD4 T cells). The listings from 1 to 100 reflect relative levels of significance.

Table 1, Column B provides the significant genes showing the best correlation with percent SzS cells, i.e., genes the expression of which best reflects tumor burden. The number assigned to each gene reflects relative levels of significance in this column with 1 as most important. When comparing unpurified patient PBMC to unpurified normal PBMC, the ratio of the expression levels of these genes most highly correlates with the percentage of tumor cells in the patient. That is, a patient with 90% circulating tumor cells has a very high ratio compared to a patient with only 5 or 10%. This is likely true because more tumor cells affect all the PBMC to a greater degree than few tumor cells, but it is possible that these genes are mainly in the tumor cells themselves.

Table 1, Column C lists those genes most useful for detecting disease in unpurified PBMC, i.e., genes which are most informative at classification when comparing PBMC from patients to PBMC from normals. This reflects differences which characterize the disease state and not necessarily changes specific to the tumor cells. The number assigned to each gene reflects relative levels of significance in this column with 1 as most important.

TABLE 1

| GENE NAME | SYMBOL | A | B | C |
|---|---|---|---|---|
| plastin 3 (T isoform) | PLS3 | 1 | 36 | 4 |
| tumor necrosis factor (ligand) superfamily, member 7 | TNFSF7 | 2 | 35 | 2 |
| cysteine dioxygenase, type I | CDO1 | 3 | 18 | 34 |
| liver-specific bHLH-Zip transcription factor | LISCH7 | 4 | 39 | 70 |
| tumor necrosis factor (ligand) superfamily, member 11 | TNFSF11 | 5 | 48 | 3 |
| ESTs, Highly similar to A35049 ankyrin 1, erythrocyte splice form 2 - human [*H. sapiens*] | N/A | 6 | 70 | 13 |
| calcium channel, voltage-dependent, alpha 2/delta subunit 1 | CACNA2D1 | 7 | 27 | 36 |
| Proteglycan 4 | PGR4 | 8 | 1 | 54 |
| fibroblast growth factor receptor 1 (fms-related tyrosine kinase 2, Pfeiffer syndrome) | FGFR1 | 9 | 14 | 29 |
| PAS domain containing serine/threonine kinase | PASK | 10 | 8 | 35 |
| chromosome 18 open reading frame 1 | C18orf1 | 11 | 92 | 32 |
| tumor necrosis factor (ligand) superfamily, member 9 | TNFSF9 | 12 | 38 | 5 |
| *Homo sapiens* cDNA FLJ32507 fis, clone SMINT1000048, moderately similar to *Mus musculus* GTPase Rab37 mRNA, mRNA sequence | N/A | 13 | 67 | 12 |
| cadherin 1, type 1, E-cadherin (epithelial) | CDH1 | 14 | 49 | 31 |
| cell division cycle 25B | CDC25B | 15 | 16 | 24 |
| *Homo sapiens* cDNA FLJ36496 fis, clone THYMU2018819, mRNA sequence | N/A | 16 | 64 | 11 |
| tumor suppressing subtransferable candidate 4 | TSSC4 | 17 | 74 | 30 |
| GS3955 protein | GS3955 | 18 | 11 | 33 |
| transducer of ERBB2, 1 | TOB1 | 19 | 69 | 1 |
| GATA binding protein 3 | GATA3 | 20 | 2 | 25 |
| EST, Highly similar to JC2398 PMS3 homolog mismatch repair protein - human [*H. sapiens*] | N/A | 21 | 54 | 9 |
| pleckstrin homology, Sec7 and coiled/coil domains 1(cytohesin 1) | PSCD1 | 22 | 60 | 80 |
| ESTs, Highly similar to IgG Fc binding protein [*Homo sapiens*] [*H. sapiens*] | N/A | 23 | 59 | 10 |
| 5-hydroxytryptamine (serotonin) receptor 2B | HTR2B | 24 | 45 | 38 |
| *Homo sapiens* cDNA FLJ32847 fis, clone TESTI2003376, mRNA sequence | N/A | 25 | 46 | 8 |
| TEA domain family member 4 | TEAD4 | 26 | 61 | 81 |

TABLE 1-continued

| GENE NAME | SYMBOL | A | B | C |
|---|---|---|---|---|
| gamma-aminobutyric acid (GABA) A receptor, alpha 1 | GABRA1 | 27 | 15 | 22 |
| annexin A6 | ANXA6 | 28 | 71 | 28 |
| nucleolar protein family A, member 1 (H/ACA small nucleolar RNPs) | NOLA1 | 29 | 79 | 87 |
| serum-inducible kinase | SNK | 30 | 41 | 71 |
| tumor necrosis factor receptor superfamily, member 25 | TNFRSF25 | 31 | 5 | 53 |
| src family associated phosphoprotein 1 | SCAP1 | 32 | 28 | 66 |
| brain-specific protein p25 alpha | p25 | 33 | 31 | 67 |
| chemokine (C—C motif) receptor 7 | CCR7 | 34 | 58 | 79 |
| kangai 1 (suppression of tumorigenicity 6, prostate; CD82 antigen (R2 leukocyte antigen, antigen detected by monoclonal and antibody IA4)) | KAI1 | 35 | 42 | 52 |
| asparagine synthetase | ASNS | 36 | 13 | 48 |
| ESTs, Moderately similar to 2203412A polycystin [*Homo sapiens*] [*H. sapiens*] | N/A | 37 | 93 | 20 |
| keratin 1 (epidermolytic hyperkeratosis) | KRT1 | 38 | 68 | 44 |
| lymphocyte-specific protein tyrosine kinase | LCK | 39 | 76 | 84 |
| ESTs, Highly similar to serine/threonine kinase 14 alpha [*Homo sapiens*] [*H. sapiens*] | N/A | 40 | 84 | 17 |
| aquaporin 3 | AQP3 | 41 | 22 | 63 |
| *Homo sapiens* full length insert cDNA clone YI61E07, mRNA sequence | N/A | 42 | 10 | 7 |
| EST | N/A | 43 | 80 | 15 |
| pim-2 oncogene | PIM2 | 44 | 19 | 60 |
| similar to RIKEN cDNA 1110002C08 gene | MGC9564 | 45 | 65 | 41 |
| ESTs, Highly similar to cadherin EGF LAG seven-pass G-type receptor 2; EGF-like-domain, multiple 2; epidermal growth factor-like 1; multiple epidermal growth factor-like domains 3; cadherin, EGF LAG seven-pass G-type receptor 2, flamingo (*Drosophila*) homo | N/A | 46 | 82 | 16 |
| potassium intermediate/small conductance calcium-activated channel, subfamily N, member 4 | KCNN4 | 47 | 63 | 43 |
| mevalonate (diphospho) decarboxylase | MVD | 48 | 51 | 75 |
| uracil-DNA glycosylase | UNG | 49 | 20 | 61 |
| bridging integrator 1 | BIN1 | 50 | 98 | 95 |
| endothelial differentiation, sphingolipid G-protein-coupled receptor, 1 | EDG1 | 51 | 12 | 58 |
| transcription factor 7 (T-cell specific, HMG-box) | TCF7 | 52 | 47 | 73 |
| paraneoplastic antigen MA1 | PNMA1 | 53 | 43 | 72 |
| hypothetical protein FLJ20551 | FLJ20551 | 54 | 52 | 76 |
| EST | N/A | 55 | 88 | 19 |
| hypothetical gene BC008967 | BC008967 | 56 | 9 | 57 |
| hypothetical protein MGC14439 | MGC1443 | 57 | 94 | 92 |
| fatty-acid-Coenzyme A ligase, long-chain 6 | FACL6 | 58 | 29 | 23 |
| interleukin 11 receptor, alpha | IL11RA | 59 | 21 | 62 |
| collagen, type VI, alpha 3 | COL6A3 | 60 | 83 | 47 |
| T cell receptor beta locus | TRB@ | 61 | 55 | 77 |
| *Homo sapiens* full length insert cDNA clone YI61E07, mRNA sequence | N/A | 62 | 4 | — |
| FtsJ homolog 1 (*E. coli*) | FTSJ1 | 63 | 6 | 56 |
| coproporphyrinogen oxidase (coproporphyria, harderoporphyria) | CPO | 64 | 96 | 27 |
| chemokine (C—X—C motif) ligand 1 (melanoma growth stimulating activity, alpha) | CXCL1 | 65 | 56 | 37 |
| guanylate cyclase activator 2B (uroguanylin) | GUCA2B | 66 | 95 | 93 |
| SH2-B homolog | SH2B | 67 | 75 | 83 |
| TNF-induced protein | GG2-1 | 68 | 78 | 86 |
| ligase I, DNA, ATP-dependent | LIG1 | 69 | 62 | 82 |
| cytochrome P450, subfamily XXIV (vitamin D 24-hydroxylase) | CYP24 | 70 | 66 | 26 |
| CD28 antigen (Tp44) | CD28 | 71 | 73 | 51 |
| diacylglycerol kinase, alpha 80 kDa | DGKA | 72 | 30 | 46 |
| 5',3'-nucleotidase, cytosolic | NT5C | 73 | 90 | 90 |
| ankyrin 3, node of Ranvier (ankyrin G) | ANK3 | 74 | 87 | 89 |

TABLE 1-continued

| GENE NAME | SYMBOL | A | B | C |
|---|---|---|---|---|
| cofilin 2 (muscle) | CFL2 | 75 | 97 | 94 |
| peroxisomal biogenesis factor 12 | PEX12 | 76 | 86 | 88 |
| CDC14 cell division cycle 14 homolog A (S. cerevisiae) | CDC14A | 77 | 24 | 65 |
| HSPC041 protein | LOC51125 | 78 | 37 | 69 |
| Down syndrome critical region gene 1-like 2 | DSCR1L2 | 79 | 33 | 49 |
| death associated protein 3 | DAP3 | 80 | 103 | 98 |
| tumor protein p53 binding protein, 1 | TP53BP1 | 81 | 53 | 40 |
| CD4 antigen (p55) | CD4 | 82 | 32 | 68 |
| translocase of outer mitochondrial membrane 70 homolog A (yeast) | TOMM70A | 83 | 77 | 85 |
| IL2-inducible T-cell kinase | ITK | 84 | 17 | 59 |
| EST | N/A | 85 | 101 | 21 |
| acetyl-Coenzyme A acetyltransferase 2 (acetoacetyl Coenzyme A thiolase) | ACAT2 | 86 | 3 | 55 |
| EphA1 | EPHA1 | 87 | 40 | 74 |
| cysteine-rich protein 2 | CRIP2 | 88 | 89 | 45 |
| profilin 2 | PFN2 | 89 | 100 | 97 |
| RNA cyclase homolog | RNAC | 90 | 34 | 39 |
| recoverin | RCV1 | 91 | 99 | 96 |
| ESTs, Highly similar to C5HU complement C5 precursor - human [H. sapiens] | N/A | 92 | 85 | 18 |
| myeloid/lymphoid or mixed-lineage leukemia (trithorax homolog, Drosophila); translocated to, 3 | MLLT3 | 93 | 40 | 50 |
| ectodermal-neural cortex (with BTB-like domain) | ENC1 | 94 | 57 | 78 |
| azurocidin 1 (cationic antimicrobial protein 37) | AZU1 | 95 | 91 | 91 |
| hypothetical protein MGC17330 | MGC17330 | 96 | 7 | 42 |
| CD5 antigen (p56-62) | CD5 | 97 | 23 | 64 |
| ESTs, Moderately similar to PIGC_HUMAN Phosphatidylinositol-glycan biosynthesis, class C protein (PIG-C) [H. sapiens] | N/A | 98 | 72 | 14 |
| tumor necrosis factor receptor superfamily, member 7 | TNFRSF7 | — | 25 | — |
| fibroblast growth factor receptor 1 (fms-related tyrosine kinase 2, Pfeiffer syndrome) | FGFR1 | — | 26 | — |
| fatty-acid-Coenzyme A ligase, long-chain 6 | FACL6 | — | 44 | — |
| ESTs, Highly similar to cadherin EGF LAG seven-pass G-type receptor 2; EGF-like-domain, multiple 2; epidermal growth factor-like 2; multiple epidermal growth factor-like domains 3; cadherin, EGF LAG seven-pass G-type receptor 2, flamingo (Drosophila) homo | N/A | — | 81 | — |
| tumor necrosis factor receptor superfamily, member 7 | TNFRSF7 | — | — | 6 |

Application of the methods of this invention to such lists of genes can produce characteristic gene expression profiles useful as diagnostic signatures indicative of CTCL. Comparable diagnostic signatures are detectable in the immune cells of patients with other types of cancers, e.g., those with solid tumors, and other types of diseases. For example, one gene expression profile indicative of the presence or stage of CTCL contains expression levels of a statistically significant number of genes selected from the genes encoding PLS3, STAT4, TRAIL, CD26, RhoB, GATA3, TNFRSF5, SCYA2, PF4, CSPG2, S100A12, KLF4, ARHB, KAL1, JUNB, DUSP1, ITGB1, TOB1, GS3955, IL11RA, C1orf29, MNDA, CD1D, CX3CR1, DTR, RPA3, MADH7, CD79A, PLAU, SEC61G, and SCYA4.

2. Solid Tumor Profiles

In one embodiment, the genes in the characteristic expression profile for a cancer characterized by a solid tumor, which demonstrate a variance from normal controls in a patient with a solid tumor, are genes associated with cell growth. Exemplary genes associated with cell growth include, without limitation, PTMA, HNRPA1, RPL41, SERPINB6, TACC1, CX3CR1, and HNRPA2B1. In another embodiment, the genes in the expression profile, which demonstrate a variance from normal controls in a cancer patient, are genes associated with actin remodeling. Such actin remodeling genes include, without limitation, ACTR1A, ARPC3, WASF2, SMARCA5, ACTB ARPC4 and MYO1F. In another embodiment, the genes in the expression profile, which demonstrate a variance from normal controls in a cancer patient, are genes associated with energy production. Some exemplary energy production genes include, without limitation, LDHA, LDHB, and ATP5G3. In yet another embodiment, the genes in the expression profile, which demonstrate a variance from normal controls in a cancer patient, are genes associated with mitosis. Such mitosis-associated genes include, without limitation, NIMA, CCNF, CDC25A and CDC25B. In yet another embodiment, the genes in the expression profile, which demonstrate a variance from normal controls in a cancer patient, are genes associated with natural killer cells (NK) and genes associated with cytotoxic T cells (CTL). Such NK and CTL genes include without limitation, FCGR3A, GNLY, PRF1, CD8A, CD2, IS2RG, GZMK, ITGAM, PFN1, TIA1, GZMB, and IL2RB.

In one embodiment of the methods of this invention, Examples 7-9 demonstrate gene expression analysis in peripheral blood lymphocytes from patients at early and late stages of solid tumors and normal controls. Both T-cell lymphoma and 6 different types of advanced solid tumors create expression profiles in peripheral blood mononuclear cells which are easily distinguished from the corresponding profiles obtained from healthy volunteers. As indicated in the example below, the samples from patients with solid tumors can be easily distinguished from controls by hierarchical clustering (see, e.g., Eisen et al 1998 Proc. Natl. Acad. Sci. USA, 95:14963-14868; Sorlie, T., et al., 2001 Proc Natl Acad Sci USA, 98:10869-10874) or supervised procedures including shrunken centroids (Tibshirani, R., et al., 2002 Proc Natl Acad Sci USA 99:6567-6572) or penalized discriminant analysis (PDA). These references are incorporated by reference for teachings concerning these techniques.

Figure 13:
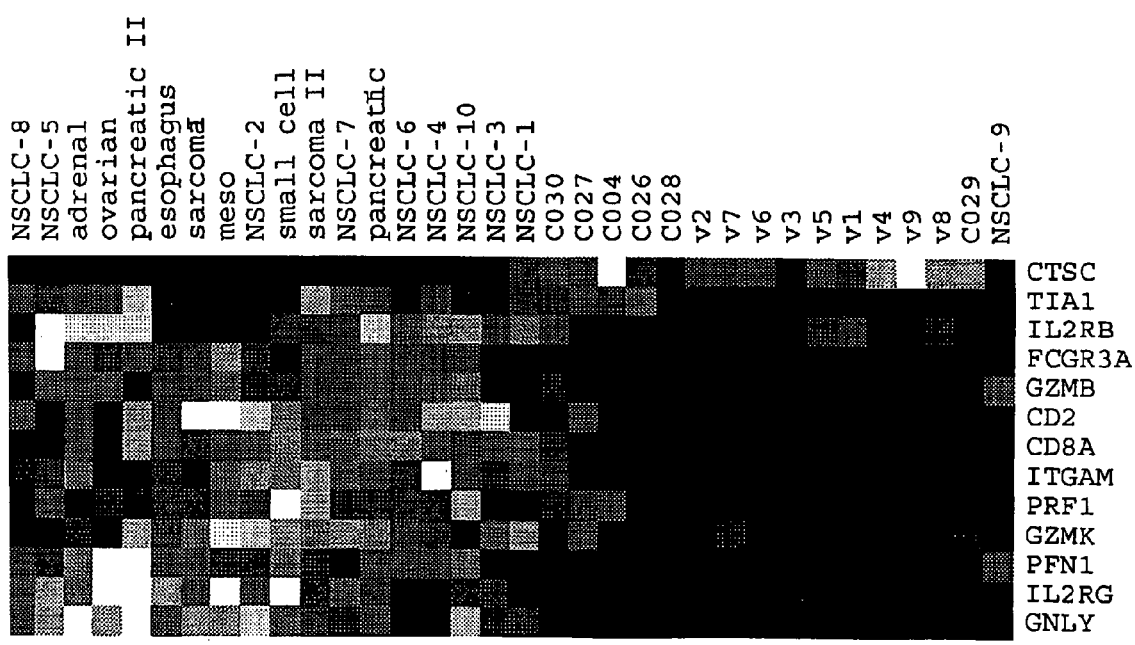
FIG. 13 is a treeview cluster diagram showing unsupervised hierarchical clustering of patients and controls using genes with known functions in NK cells and cytotoxic (CD8) lymphocytes. Individual patients are represented as column headings along the top of the diagram. Genes forming the profile are indicated as row labels.

An example of expression profiles generated from samples from NSCLC patients, patients with a variety of cancers, including adrenal, ovarian, pancreatic mesothelioma, and sarcoma, and controls using hierarchical clustering is shown in FIG. 13. Expression profiles were established using the following panel of genes: cathepsin C, TIA1 cytotoxic granule-associated RNA binding protein, interleukin 2 receptor β, Fc fragment of IgG, low affinity IIIa, receptor for CD16, granzyme B, granzyme 2, cytotoxic T-lymphocyte-associated serine esterase 1, CD2 antigen p50, sheep red blood cell receptor, CD8 antigen, alpha polypeptide p32, integrin, alpha M complement component receptor 3α (also known as CD11b), perforin, granzyme K serine protease, granzyme 3; tryptase II, profilin 1, interleukin 2 receptor, gamma severe combined immunodeficiency, and granulvsin. As with all the treeviews, the black squares indicate up-regulated genes in the sample; the white squares indicate down-regulated genes; and the gradations of gray squares indicate genes with expressions of relative intermediate over- or under-expression depending upon their closeness to the black or white sides of the color scale.

In spite of the consistency of the cancer group, it has a substantially greater variance than the control group. Part of this variance stems from a variable degree of progressive failure of the immune response in cancer patients. Disease progression is estimated by projecting each sample on the AverageControl-AverageCancer vector, by the shrunken distance to control centroid, and by crossvalidation with PDA. To identify the most significant genes, either the median distance from the control centroid, or discriminant loadings obtained from PDA performed on Control-Cancer groups after the outliers have been removed is employed as the method. Two main groups were identified as having genes changed the most with disease progression. The highest scores obtained with both methods described above identified the first group, which contains genes associated with cell growth, actin remodeling, energy production, and mitosis. The second group was identified by selecting genes associated with NK cells and cytotoxic T-cells, and demonstrating that all of these genes are significantly downregulated. See FIG. 15.

For example, a characteristic gene expression profile indicative of the presence or stage of a solid tumor cancer comprising expression levels of a statistically significant number of genes selected from the genes encoding PTMA, HNRPA1, RPL41, SERPINB6, TACC1, CX3CR1, and HNRPA2B1, ACTR1A, ARPC3, WASF2, SMARCA5, ACTB ARPC4, MYO1F, LDHA, LDHB, ATP5G3, NIMA, CCNF, CDC25A, CDC25B, FCGR3A, GNLY, PRF1, CD8A, CD2, IS2RG, GZMK, ITGAM, PFN1, TIA1, GZMB, and IL2RB.

C. MONITORING METHOD

Another aspect of the present invention involves identifying or monitoring the effects of a therapeutic agent or regimen on a patient having a cancer. According to this method, a selected therapeutic agent or treatment regimen is administered to the patient. Periodically during and/or after administration of the agent or during and/or after completion of the therapeutic regimen, a sample containing immune cells and/or cancer cells of the subject is examined for expression of a statistically significant number of non-tumor or tumor genes in the cells. One embodiment of this method employs an expression profile to diagnose a solid tumor cancer involving the expression characteristics of at least one non-tumor gene. Preferably, as described above, an embodiment of this method employs an expression profile involving the expression characteristics of at least four non-tumor genes. Preferably, as described above, an embodiment of this method employs an expression profile involving the expression characteristics of at least eight non-tumor genes. In other embodiments, an expression profile involves characteristics of more than 10 genes or more than 30 or more than 50 non-tumor genes, such as those listed specifically above and in the examples for solid tumor cancers. Still other statistically significant numbers of genes may form a profile as described above. The profile is obtained using the techniques as described above.

In other embodiments in which the cancer to be diagnosed is not characterized by solid tumors, such as CTCL, an expression profile involves the expression characteristics of at least one gene that is the product of the cancer. Preferably, as described above, an embodiment of this method employs an expression profile involving the expression characteristics of at least four such genes. Preferably, as described above, an embodiment of this method employs an expression profile involving the expression characteristics of at least eight such genes. In other embodiments, an expression profile involves characteristics between 10 to about 20 such genes or about 40 such genes, such as those listed specifically above and in the examples for CTCL. Still other statistically significant numbers of genes may form a profile as described above. The profile is obtained using the techniques as described above.

Thereafter, this patient's current profile is compared to the same profile obtained from the patient prior to administration or treatment and to the characteristic disease profile. Optionally this current profile is also compared to a control profile, or average of a number of profiles, from one or a population of healthy subjects. A statistically significant variance in expression of the genes in the current profile from the prior profile or from the characteristic profile or that of normal controls indicates the response of the patient to the therapy.

Thus, this method is adapted to determine preferred therapies for individual patients, because different patients respond differently to the variety of existing therapies for cancer treatment. Application of this method enables the selection of the therapy for which the patient is most responsive. In fact, the invention contemplates the establishment of multiple expression profiles for various cancers based on the collection of profiles of multiple cancer patients. The development of average profiles for certain cancers, as well as average profiles of patients responsive to selected therapies for selected cancers enables the use of a modified method of determining a patient's likely response to a selected therapy.

For example, the patient's own expression profile is obtained before any therapy is applied. The patient's profile is compared with the profiles of other populations of cancer patients, who were responsive to different types of therapies ("therapeutic profiles"). The therapeutic profile, which the patient's profile most closely matches, is used to predict the patient's response to that same therapy. Thus, this modified method does not require that the patient be treated before the profile is obtained.

Still other variations on these diagnostic methods are likely.

D. SCREENING METHODS

In yet another aspect, the present invention provides a screening method for identifying a cancer therapeutic agent or regimen useful for the treatment of a cancer. This method can be employed to determine the appropriate selection from among many pharmaceutical reagents or therapies for the treatment of individual cancers or groups of cancers. According to this method, a selected therapeutic agent or treatment regimen is administered to test a mammalian subject having a cancer. The test subject is desirably a research animal, e.g., a laboratory mouse or other. Periodically during and after administration of said agent or regimen, a sample containing immune cells of the test subject is examined and an expression profile of a statistically significant number of non-tumor genes is generated. The genes in the test profile are compared to the genes in a characteristic gene expression profile for a cancer. The characteristic profile is obtained and compared using the methods described above. Thereafter, this test subject gene profile is compared to the same profile obtained from the subject prior to the start of the therapy. Optionally the current subject profile can be compared to an average control profile from a population of healthy subjects. A variance in expression of the statistically significant genes is reviewed among the current profile, characteristic profile, healthy profile, and the prior profiles. If a variance in the current test profile is closer to the profiles of the normal control than to the disease profile, such results indicate that the therapeutic agent or regimen is a desirable cancer therapeutic for the particular cancer in question.

E. NEW DIAGNOSTIC METHODS AND REAGENTS FOR CTCL

The inventors surprising discovered that human tissue plastin protein or PLS3 was uniquely expressed in the malignant T-cells of CTCL patients. As supported by the following examples, PLS3 is expressed only in patients and never in control PBMC, as expression of this gene is normally not found in lymphoid cells. This makes PLS3 an extremely sensitive marker for CTCL. Its presence is diagnostic for CTCL in 70% of the patients tested. PLS3 is a 627 amino acid sequence SEQ ID NO: 1. See the NCBI database Accession No. P13797.

Thus, as one aspect of the invention, a novel diagnostic method for diagnosing CTCL involves detecting the presence of PLS3 in lymphoid cells of a suspected CTCL patient. Useful in such a method are ligands to PLS3, such as the ligands described below. An assay for detection of PLS3 may be employed to monitor the status of a CTCL patient undergoing therapy. The selection of particular assay steps for detection of PLS3 as a peptide or for detection of a nucleic acid sequence encoding PLS3 may be readily selected from among known assay formats by one of skill in the art. Such known assay formats, include, without limitation, e.g., ELISA, Western blotting, FACS analysis for protein or polymerase chain reaction, quantitative real-time PCR (qRT-PCR) for nucleic acids, and immunofluorescence and confocal microscopy, among others. Such selection of assay steps is routine and does not limit the present invention.

For example, a method for diagnosing CTCL can involve detecting and identifying the level of expression of PLS3 in a patient by assaying a peripheral blood or whole blood sample with a labeled ligand capable of binding PLS3 or nucleic acid sequences encoding PLS3. The method includes the steps of incubating the subject's peripheral blood with plates or beads on which are bound one or more ligands to PLS3, washing away unbound biological materials, and detecting or measuring any PLS3 peptide or nucleic acid molecules expressing PLS3 remaining in the washed sample. Depending on the type of label employed, the signal produced by the label may be evoked by further adding a substrate which reacts with the enzyme, e.g., producing a color change or by irradiating the sample with an excitation wavelength suitable to detect a fluorochrome, among other methods. Other conventional labels may also be incorporated into this assay design.

The use of such ligands that bind the above-described epitope of PLS3 and the methods described herein provide a novel method of diagnosing most cases of CTCL.

Such ligands may be readily selected from among various antibodies to PLS3, antisense sequences or ribozyme sequences capable of hybridizing specifically to an amino acid or nucleic acid sequence encoding the designated epitope of PLS3. Similarly such ligands include those compositions that hybridize to naturally occurring variants of the polypeptide or nucleic acid sequences encoding the above-defined epitope.

In addition to known ligands to PLS3, the invention also discloses as another aspect of this invention a novel ligand which specifically binds to a PLS3 epitope sequence located within a peptide or polypeptide of the formula Ser-Lys-Asp-Glu-Leu-Asp-Glu-Leu-Lys-Glu-Ala-Phe-Ala-Lys (amino acids 7-20 of SEQ ID NO:1) or which specifically binds to a nucleic acid sequence encoding the above-defined peptide or polypeptide or other sequences specific to PLS3.

Another novel ligand is one that specifically binds to a PLS3 epitope sequence located within a peptide or polypeptide of the formula Arg-Glu-Ile-Ile-Gln-Lys-Leu-Met-Leu-Asp-Gly-Asp-Arg-Asn-Lys-Asp (amino acids 51-66 of SEQ ID NO: 1) or which specifically binds to a nucleic acid sequence encoding the above-defined peptide or polypeptide or other sequences specific to PLS3.

The term "antibody" as used herein is intended to encompass an isolated polyclonal, or monoclonal, synthetic or recombinant antibody of classes IgG, IgM, IgA, IgD and IgE. Antibody fragments are also useful, including without limitation, a Fab fragment, a Fab' fragment, a F(ab')2 fragment or an Fc antibody fragment of one or more of the above intact antibodies. Similarly a single chain Fv antibody fragment or a recombinant construct comprising a complementarity determining region of an antibody may be employed as the antibodies useful in these methods. Further, a synthetic antibody or chimeric antibody or humanized antibody construct which shares sufficient CDRs to retain functionally equivalent binding characteristics of an antibody that binds a desired cell surface antigen may also be employed as the antibody of choice.

In one embodiment, an isolated antibody directed which binds PLS3 is a polyclonal antibody. Such antibodies are typically produced by immunizing a mammal, preferably a primate, with the above-defined peptide/polypeptide, optionally bound to a carrier. Such antibodies may be produced in laboratory animals, preferably primates, in transgenic animals, including so-called "humanized" transgenic animals. However, a desirable host for raising polyclonal antibodies to a composition of this invention includes humans. The titer of such polyclonal antibodies raised in the mammal exposed to the PLS3 epitope of this invention can be monitored by standard techniques, such as with an enzyme-linked immunosorbent assay. If desired, the antibody molecules can be isolated from the mammal, e.g., from the whole blood, plasma or serum, and further purified from the plasma or serum of the immunized mammal by conventional techniques. Conventional harvesting techniques can include plasmapheresis, protein A chromatography, among others. Such polyclonal antibody compositions may themselves be employed as pharmaceutical compositions of this invention.

Alternatively, antibody producing cells may be obtained from the mammals and used to prepare other forms of antibodies and ligands, e.g., monoclonal antibodies, chimeric antibodies, humanized antibodies, human antibodies, ligands produced by screening phage displays, antibody fragments and mixtures thereof, and synthetic antibodies, monoclonal antibodies, chimeric antibodies, humanized antibodies and fully human antibodies. Preparative techniques for generation of these types of ligands are known and the ligands themselves may be generated using the disclosed amino acid sequences of the PLS3 epitope and optional immunogens. See, e.g., Kohler and Milstein 1975 *Nature*, 256:495-497; Kozbor et al, 1983 *Immunol. Today*, 4:72; Cole et al, 1985 *Monoclonal Antibodies and Cancer Therapy*, Alan R. Liss, Inc., pp. 77-96; Harlow et al., *Antibodies A Laboratory Manual*, Cold Spring Harbor Laboratory, 1988; Queen et al., *Proc. Nat'l. Acad. Sci. USA*, 86:10029-10032 1989; Hodgson et al., *Bio/Technology*, 9:421 1991; International Patent Application No. PCT/GB91/01554, International Patent Publication No. WO92/04381 and International Patent Application No. PCT/GB93/00725, International Patent Publication No. WO93/20210).

Other antibodies to the PLS3 epitope may be developed by screening a recombinant combinatorial immunoglobulin library (e.g., antibody phage displays) with the epitope of this invention to isolate immunoglobulin library members that bind to the PLS3 peptide (W. D. Huse et al., *Science*, 246: 1275-1281 1988). Kits for generating and screening phage display libraries are commercially available, e.g., Pharmacia Recombinant Phage Antibody System, Catalog No. 27-9400-01; Strategene Phage Display kits, etc. See, e.g., U.S. Pat. No. 5,223,409, International Patent Publication Nos. WO92/09690, WO90/02809, etc. Chimeric antibodies may similarly be developed using known techniques (Morrison et al, 1984 *Proc. Natl. Acad. Sci. USA*, 81:6851; Takeda et al, *Nature*, 313:452 1984, among others). Chimeric antibodies are molecules in which different portions are derived from different animal species. Single chain antibodies may also be prepared by conventional methods (see, e.g., U.S. Pat. Nos. 4,946,778 and 4,704,692) using the variable portions of the polyclonal or monoclonal antibodies produced according to this invention. Antibody fragments, such as the Fab, $F(ab')_2$ and Fv fragments and libraries thereof may also be employed in various aspects of this invention.

In other embodiments of this invention, the ligand is a nucleic acid molecule. For example, a nucleic acid probe is readily generated to bind to the nucleic acid sequences encoding the epitope sequences identified above or other PLS3 specific sequences. Such an "antisense" sequence as used herein is intended to encompass a single-stranded, partially single stranded or double stranded compound that is sufficiently complementary to the nucleic acid sequence encoding the above-defined sequences, to be specifically hybridizable thereto. Such a sequence may hybridize completely to the epitope, i.e., be 100% complementary. Alternatively, the sequence may hybridize with less than 100% avidity, but sufficiently to identify the epitope of PLS3 from non-PLS3 sequences. Alternatively, such a sequence may hybridize over one or more segments such that intervening or adjacent segments of the antisense sequence are not involved in the hybridization event (e.g., a loop structure or hairpin structure, such as a ribozyme).

In certain embodiments of this invention, the ligand, e.g., antibody or nucleic acid molecule, of this invention is desirably associated with, or conjugated to, a detectable label. The label on the reagent may be selected from the many known diagnostic labels, such as radioactive compounds, fluorescent compounds and proteins, calorimetric enzymes, etc. In one embodiment, the label can be a colorimetric enzyme, which upon contact with a substrate produces a detectable color signal. As another example, fluorochromes are commonly used labels for diagnostic reagents. Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and Alexa dyes. Any fluorochrome may be employed, include those excitable by radiation in the red, blue or green wavelengths or combinations thereof. All of these fluorescent dyes are commercially available, and their uses known to the art. Still other fluorescent dyes may be available from other sources or may be developed in the future. Such dyes are anticipated to be useful in the compositions and methods of this invention.

Methods for coupling or associating the label with the ligand are similarly conventional and known to those of skill in the art. Known methods of label attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995). Thus, selection of the fluorochrome label(s) and coupling methods do not limit this invention.

Ligands of this invention are usefully assembled into kits, which also contains miscellaneous reagents and apparatus for reading labels, e.g., certain substrates that interact with an enzymatic label to produce a color signal, etc., apparatus for taking blood samples, coated solid supports, miscellaneous substrates and apparatus for evoking or detecting the signals provided by the labels, conventional apparatus for taking blood samples, as well as appropriate vials and other diagnostic assay components, and suitable packaging. Thus an embodiment of this invention is a diagnostic kit for use in diagnosing CTCL, which contains a ligand of this invention as well as other conventional diagnostic kit components. One of skill in the art may also readily select other conventional diagnostic components for this kit.

Such kits and reagents may be employed in a method for detecting the presence of PLS3 in lymphoid cells.

In addition to their use as diagnostic markers, such ligands, preferably antibodies may be coupled with a therapeutic protein, such as a toxin by conventional techniques and employed in a therapeutic method for killing the tumor cells. In this embodiment of a composition of this invention, exemplary conventional therapeutic proteins include toxins such as diphtheria toxoid and tetanus toxin. One of skill in the art can readily select an appropriate therapeutic protein for delivery to the cancer cell via the above-noted ligands. Such antibody-toxin complexes may be used by administering an effective amount of the complex to a patient with CTCL. The ligand targets the toxin to the PLS3 epitope and can be used to kill the cell.

The genes listed in Table 1, Column A, above provide are the best candidates for making additional ligands useful in diagnosis and therapy of CTCL.

EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1

Analyses of PBMC from Patients with CTCL

A. Purification of PBMC from CTCL Samples and Preparation of Normal Controls.

PBMC were obtained by Ficoll gradient separation from peripheral blood of both normal volunteers and leukemic phase CTCL (Showe, L. C. et al, *Ann N Y Acad Sci*, 795: 413-415, 1996 (Showe I); Gerosa, F., et al., *Clin Immunol*, 92: 224-234, 1999 (Gerosa II)). A total of 48 viably frozen CTCL patient samples with Sezary cells ranging from 5-99% of the lymphocyte population were analyzed. The Ficoll-purified PBMC fraction from high SS patients was 60-95% $CD4^+$ malignant cells with a predominantly Th2 phenotype, and in decreasing abundance small percentages of B cells, monocytes and dendritic cells. Th2 skewed PBMC, prepared by culturing for 4 days in IL-4 and anti-IL-12, were used as controls for the high Sezary cell patients, as many characteristics of advanced disease are associated with a Th2 polarized immune response. Under these conditions >95% of the $CD4^+$ T cells express the Th2 phenotype (Nakamura, T., et al. 1997 *J Immunol* 158:1085-1094; Nakamura, T., et al. 1997 *J Immunol* 158:2648-2653; Gerosa II). Th1 skewed PBMC were prepared by culturing in IL-12 and anti-IL4 for 4 days (Gerosa, F., et al, 1996 *J Exp Med* 183:2559-2569). CTCL patients are described as high or low Sezary with reference to the blood tumor burden and were selected based on percent circulating Sezary cells regardless of whether erythroderma was also present. All samples were collected with appropriate patient consent and IRB approval. See Tables 2 and 3.

TABLE 2

| Patient Code | Survival Time (mos) | % Sezary |
|---|---|---|
| S1042 | 44 | 15 |
| S1051 | 102 | 5 |
| S1052 | 92 | 8 |
| S1061 | 16 | 15 |
| S1062 | 10 | 15 |
| S1072 | 5 | 97 |
| S1082 | 5 | 75 |
| S1091 | 73 | 66 |
| S1103 | 20 | 99 |
| S1111 | 76 | 75 |
| S1125 | 3 | 90 |
| S1134 | 45 | 75 |
| S1143 | 5 | 99 |
| S1151 | 4 | 60 |
| S1161 | 15 | 90 |
| S1182 | 44 | 90 |
| S1183 | 24 | 90 |
| S1192 | 37 | 90 |
| S1201 | 3 | 5 |
| S1211 | 3 | 15 |
| S1221 | 14 | 32 |
| S1231 | 2 | 91 |
| S1241 | 51 | 21 |
| S1251 | 69 | 37 |
| S1261 | 17 | 34 |
| S1271 | 3 | 64 |
| S1281 | 69 | 62 |
| S1291 | 21 | 60 |
| S1301 | 112 | 48 |
| S1311 | 84 | 61 |
| S1331 | 61 | 46 |
| S1341 | 3 | 34 |
| S1351 | 1 | 32 |
| S1361 | 46 | 67 |
| S1381 | 24 | 79 |
| S1391 | 67 | 15 |
| S1401 | 11 | 39 |
| S1411 | 9 | 63 |
| S4121 | 64 | 30 |
| S1431 | 60 | 22 |
| S1441 | 43 | 49 |
| S1451 | 51 | 36 |
| S1461 | 65 | 24 |
| S1471 | 2 | 53 |
| S1481 | 25 | 28 |
| S1491 | 59 | 83 |
| S1492 | 107 | 50 |
| S1501 | 43 | 71 |

TABLE 3

| Control Code | Type |
|---|---|
| C0022 | Th2 |
| C0032 | Th2 |
| C0041 | Untreated PBMC |
| C0081 | PHA Blast |
| C0101 | Th1 |
| C0102 | Th2 |
| C0111 | Th1 |
| C0112 | Th2 |
| C0172 | Tha |
| C0173 | Th1 |
| C0183 | Th1 |
| C0186 | Th2 |
| C0196 | Th2 |
| C0206 | Th2 |
| C0211 | Untreated PBMC |
| C0212 | Th1 |
| C0213 | Th2 |
| C0221 | Untreated PBMC |
| C0222 | Th1 |
| C0223 | Th2 |

B. cDNA Arrays cDNA filter arrays were purchased from the Wistar Institute Genomics facility. (http://www.wistar.upenn.edu/genomics/). Three 2.5×7.5 cm nylon filters, HA-01, -02, and -03, carrying a total of 6600 probes for 4500 individual known genes were used to analyze the eighteen high Sezary count (>60% Sezary cells) samples, and twelve samples from healthy controls. The 30 samples were hybridized as a single batch on sequentially printed arrays. An additional 30 low Sezary count samples and eight controls were analyzed only on gene filter HA03. All arrays used in the study were printed from the same PCR preparations. Reproducibility studies show a >90% correlation between samples hybridized in triplicate. Sequence verified clones were purchased from Research Genetics. Clones for significant genes were sequenced for verification.

C. RNA Isolation, Amplification, and Hybridization

Complete protocols can be accessed at http://www.wistar.upenn.edu/genomics/. RNA was isolated using Trireagent™ reagent (Molecular Research Center) and total RNA samples were amplified (aRNA) using a modified T7 protocol (Van Gelder, R. N., et al, 1990 *Proc Natl Acad Sci USA* 87:1663-1667), accessed at http://cmgm.stanford.edu/pbrown/protocols/. The aRNA target (0.5 μg) was labeled with $^{33}P$, 3000-5000 Ci/mM using Reverse transcriptase. Hybridization was in 2.5 ml of Micro-Hyb™ reagent (Research Genetics) at 42° C. for 18 hours. HA-01 and HA-03 filters were hybridized with the same labeled target. HA-02 was hybridized separately with the same aRNA preparation. Filters were exposed to a PhosphorImager™ screen for four days, scanned at 50 micron resolution on a Storm PhosphorImager™ apparatus, and visualized using ImageQuant™ software (Molecular Dynamics).

D. Real-Time PCR

The cDNAs were generated from 0.5 μg of aRNA using Superscript II™ reagent (Life Technologies, Inc). Gene specific primers (IDT, Inc., IA) are listed in Table 4. PCR was performed in a Light Cycler™ apparatus (Roche Diagnostics). Cycle parameters were: 94° C., 3 minute hot start and then, 40 cycles of 94° C., 10 seconds; 56° C. or 60° C., 10 seconds; and 72° C., 25 seconds. Product specificity was checked by melting curve analysis and gel electrophoresis and relative gene expression levels were determined by comparison with a standard curve and normalized by dividing the relative gene expression by the average expression of three housekeeping genes, SF3A1, CCT3, and MBD4.

TABLE 4

| SYMBOL | FORWARD | SEQ ID NO: | REVERSE | SEQ ID NO: | SIZE (bp) | Tm (° C.) |
|---|---|---|---|---|---|---|
| SF3A1 | GGATAAGACGGAATGGAAACT | 2 | AATGGCAGGGACTTGACA | 3 | 271 | 56 |
| CCT3 | AGCTGGGACAGAAAGAAAGGGACT | 4 | AACAGTGGAAGACGGCAGTT | 5 | 436 | 56 |
| GATA3 | TATCCATCGCGTTTAGGC | 6 | CCCAAGAACAGCTCGTTTA | 7 | 280 | 60 |
| ARIO3 | ATAGGCCCCAATACTTGT | 8 | ACACTTAATGCACTCGTCA | 9 | 237 | 60 |
| DUSPI | TGAAGGCAGACACCTAC | 10 | GCACATTCGGGACCAATA | 11 | 305 | 60 |
| PLS3 | GCTTGACAAAGCAAGAGT | 12 | GCATCTTCCCTCTCATACC | 13 | 300 | 60 |
| CDSIW | CCCTGCTATACATAAAGGTG | 14 | GCTTGTGAGATTGAGAATGAAC | 15 | 241 | 60 |
| ISGI5 | GCTTGAGGCCGTACTCCC | 16 | CAAATGCGACGAACCTCTGA | 17 | 203 | 60 |
| ITGB1 | GCTTCCATATCAGCAGTAAT | 18 | GTAGAAAGTCGGGACAAAT | 19 | 241 | 60 |
| CDKN2 | DCTGCTGAAGCAAGGTG | 20 | CAGTGTGACCCTCTTGAA | 21 | 181 | 60 |
| CCR1 | GGGTAAATGGAAATGATGAGT | 22 | GAGTTGAGACCTAACGAGAAA | 23 | 195 | 60 |
| JUNB | ACTCTTTAGAGACTAAGTGCG | 24 | CCACCTCGACGTTTACAA | 25 | 258 | 60 |
| CYPTB1 | TTGGTATATCAAACAGTAAAGGC | 26 | TCATGTCCCAGAACTTAGC | 27 | 321 | 60 |
| STAT2 | TCCTAGAACCTGGATATTTACAAAG | 28 | GTGTATGCCGGTGTTGA | 29 | 197 | 60 |
| ARIIGEF6 | TGCTCTCAGATTAACATGGC | 30 | GGAATACTTTAGTTGATTGCTGAA | 31 | 199 | 60 |
| SELL | CTCATCATGGGTTGGATTAG | 32 | CTGCAAGTGACATCTCTTT | 33 | 211 | 60 |
| CDSA | ATAACAGCATAGTACAACCCT | 34 | GTATGGTACAAGCAATGCC | 35 | 190 | 60 |
| DPPS | TTGAATTATCCGGTCGGG | 36 | CCTGGTCGTGTTGGTATG | 37 | 280 | 60 |
| PPIA | CGTAAACCCTGGAATAATTCT | 38 | CTGTGTCTCCTTCGAGGTA | 39 | 197 | 60 |
| ZNF161 | CAGGTCACAATCCCTATTATAC | 40 | ACACTAGCAGGACTCTTC | 41 | 286 | 60 |
| SOD1 | CCACATAATAAGTGCCATACAG | 42 | CCTTAAAAGTGTAATTGTGTC | 43 | 229 | 60 |
| ICAM2 | AGAAGGTATTCGAGGTACAC | 44 | GTACACGCTGACGTTG | 45 | 257 | 60 |
| TNFRST6 | ACGTCTGTTGCTAGATTATCG | 46 | CACGCAGTCTGGTTCA | 47 | 213 | 60 |
| TNFST6 | AAGGTCTACATGAGGAACT | 68 | AGCCGAAAAACGTCTGA | 49 | 205 | 60 |
| LCP1 | ATAGAGGGCGTCTTGC | 50 | CTCACATACACACACACC | 51 | 229 | 60 |
| ILI8 | GGATGAATTGGGGGATAGA | 52 | GTCACTACACTCAGCTAATTT | 53 | 218 | 56 |
| TNFRST5 | CACTATCACAAACAATGCTG | 54 | ACCTTGAAGAACCTCTCAC | 55 | 221 | 60 |
| TNFST5 | TATACACTCCAAGGCATGTAG | 56 | CTCCCCATTTCCCTTCTG | 57 | 279 | 60 |
| MGAM | ATTATTCCTCCCACCGC | 58 | TGAACTGGGTCCATGAT | 59 | 187 | 60 |
| CD44 | ATGGTTATGTTTCCAACGG | 60 | GTGGACTCAACGGAGAGG | 61 | 189 | 56 |
| NFKDIA | GTACAGCATTTACAGGAGGG | 62 | CTCACCTTTGTGGGGTT | 63 | 198 | 56 |
| NFKB1 | TACAGGTCCAGGGTATAGC | 64 | GCTCTGTGGTTTCAATAACT | 65 | 203 | 56 |
| MBO4 | CACATCTCTCCAGTCTGC | 66 | CGACGTAAAGCCTTTAAGAA | 67 | 207 | 56 |
| CDID | TGAGACGCCTCTGTTTC | 68 | ACACCTCAAATACATACCTACT | 69 | 189 | 60 |
| CX3CR1 | AGTAATGGCAAGTAAATTGGG | 70 | CAAATAGTGCTCGCTTTCT | 71 | 201 | 60 |
| IL1R2 | AGGACACAGCGGTAATAG | 72 | CCATTGAGCCTCAGAGT | 73 | 269 | 60 |
| 1%FSF10 | ACGTGTACTTTACCAACGA | 74 | ATGCCCACTCCTTGAT | 75 | 380 | 60 |
| IL1R1 | ATGGCTCAATACCTTTTATTGC | 76 | AAAACTTTAATGCCTTCCAC | 77 | 198 | 60 |

E. Array Analysis

The data for each array was analyzed with ArrayVision™ software (Imaging Research), using the median pixel for each spot and local background correction. Expression values for each array were normalized by the background corrected signal median spot of the array and then transformed to corresponding z-scores for clustering. T-tests, frequency analysis, and permutations were done using Excel™ software and Visual Basic™ software. Dynamic range of signals was, on average, 10-20,000 (normalized median density of 0.15 to 3000). The detection limit for these conditions and arrays, calibrated by quantitative PCR (QPCR) with a plasmid standard, is approximately 0.03 molecules per cell.

F. Penalized Discriminant Analysis

Supervised classification of genes and arrays was carried out using penalized discriminant analysis (PDA), as described in Hastie et al, 1995 and Raychouderi, 2001, cited above, and as provided by CLEAVER (Classification of Expression Array Version 1.0: http://classify.stanford.edu/) internet site. This program, a variant of linear discriminant analysis, classifies unknown samples based on the information from a two class training set used to identify genes whose expression levels have a maximum variation between the training classes, and a minimal variation within each training class. PDA adds a "penalty" in the form of a diagonal matrix, which is added to the covariance matrix, allowing the latter to be inverted even though genes greatly outnumber samples. The exact value of this penalty (between 100 and 1000) did not significantly alter the ranks of the informative genes. The implementation of PDA used in the CLEAVER™ program limits the number of genes used in training and subsequent classification to the 500 genes, whose expression best distinguishes between the positive (patient) and negative (control) examples. Although more genes are input to the program and are correlated with the training classes, no more than 500 are used in classification. The program outputs two sets of results: a positive or negative score that indicates how well a sample is assigned to a particular class and a "predictive power" assigned to each gene as a measure of its ability to discriminate the two classes.

After demonstrating 100% cross-validation accuracy with a complete gene set, a t-test filter of p<0.1 was added to the input data to help to identify the best classifiers by eliminating genes which contribute a disproportionate amount of noise to the analysis.

G. Selection of Correlated Gene Clusters

Clusters of genes whose expression patterns among patients were highly correlated with selected seed genes in a microarray data set were selected as follows. An average expression profile for the seed is calculated as a weighted sum of the gene expression values for all genes that have a correlation coefficient with the seed gene higher than 0.7. The correlation coefficients are used as weights for this calculation. Then the correlation coefficients between the computed average profile and each gene in the data set are determined. The correlation coefficients are binned, and their distribution determined to permit assignment of genes to the cluster that are above a selected correlation coefficient. Each gene in the data set is used as a seed. When this analysis is repeated on permuted expression values for each gene, there is no correlation over 0.7.

H. Results

The eighteen samples from seventeen patients used for the initial studies were selected to have high Sezary cell counts, ranging from 60-99% of total circulating lymphocytes. Two samples from patient S118 were taken one year apart. All patients had ratios of $CD4^+$ to $CD8^+$ T-cells greater then ten. This extreme departure from the normal 3:2 $CD4^+/CD8^+$ ratio is characteristic of leukemic phase disease.

Th2 skewed PBMC were selected as controls for the high Sezary cell patients as many characteristics of advanced disease are associated with a Th2 polarized immune response, including: (1) high serum levels of IgE and IgA, (2) increasing serum levels of anti-inflammatory cytokines IL-4, IL-5, and IL-10, (3) a general loss of T-cell responsiveness to mitogens and antigens (Vowels, B. R., et al, 1992 *J Invest Dermatol* 99:90-94), (4) lack of expression of the β2 chain of the IL-12 receptor (Showe et al, 1999, cited above). For the discriminant analysis of samples with low Sezary cell counts, data was included for untreated PBMC and Th1 skewed controls where indicated, in order to provide greater diversity within the control population.

To find candidate differentially expressed genes, normalized expression levels were compared between eighteen high Sezary cell samples and nine Th2 skewed controls. The data set was first analyzed gene-by-gene with a univariate t-test. FIG. 1A shows the number of significant genes (SG) detected as a function of p-value. At p<0.01, 385 unique genes were found to be significantly upregulated or downregulated in patients relative to the controls, rising to 1400 genes at p<0.10. To estimate the number of false-positive genes, the experimental and control labels were permuted (10,000 times); t-tests were performed on each permutation, and the number of "significant genes" that would arise by chance if patients and controls were drawn from the same population was determined. The median number of these significant genes, which are false positives relative to the original data set, was calculated for each permutation at each p-value cut-off as shown (FP).

The median number of false positives at p<0.01 was 27, or approximately 8% of the 385 significant genes at that p value (see line FP). The number of true positive genes, the number of observed significant genes minus the number of false positives (SG-FP), rises to a near-constant value of approximately 1000 at p=0.15. This ignores the number of false negative genes arising in the observed data that would increase the number of truly positive genes. If this value is compared to the number of true positives at a given p-value, and if only the genes detected at p<0.01 are considered, many potentially "significant genes" would be missed (MG in FIG. 1A).

If stringency is increased and higher percentiles of permutations are used (60-95th) and these values are subtracted from SG, then fewer and fewer true positive genes are reported (FIG. 1B). However, even if the 95th percentile of the permuted samples is used, 300 true positive genes are still identified at p<0.01. Of the 385 differentially expressed genes identified at p<0.01, average changes in expression relative to Th2 controls range from 25-fold for overexpression to 7-fold for underexpression.

Figure 2A:
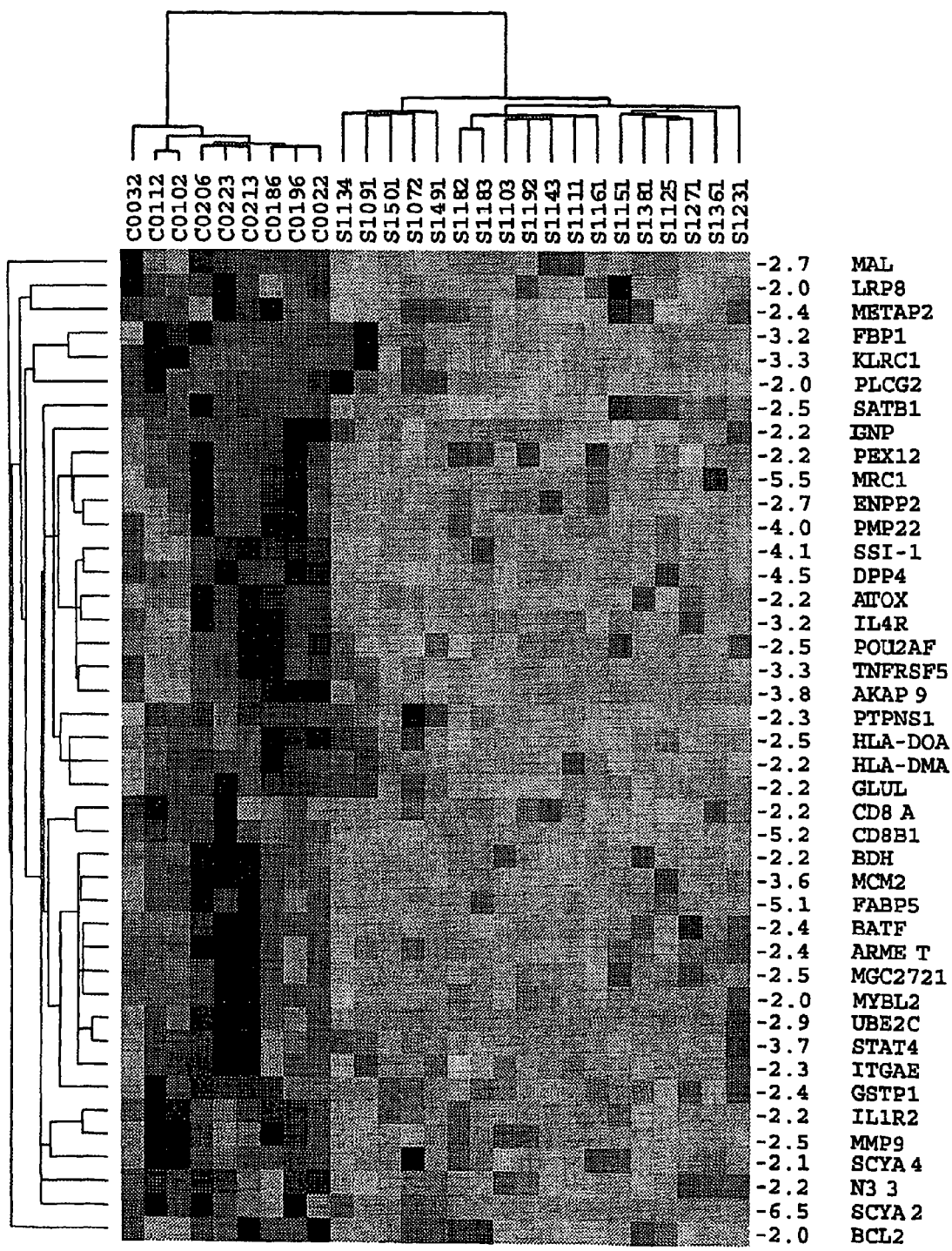
FIG. 2A is the top portion of a treeview showing the variation in expression of the 135 p<0.01 significant genes that are either upregulated (black squares) or downregulated (white squares)>2-fold in eighteen high tumor CTCL burden patients as compared to nine Th2-skewed controls. The pale cluster identifies genes which are downregulated and the dark cluster genes which are upregulated in patients versus controls. Gray squares show variation between up and down-regulation. Values for fold increases or decreases (−) precede the gene symbols.
Figure 2B:
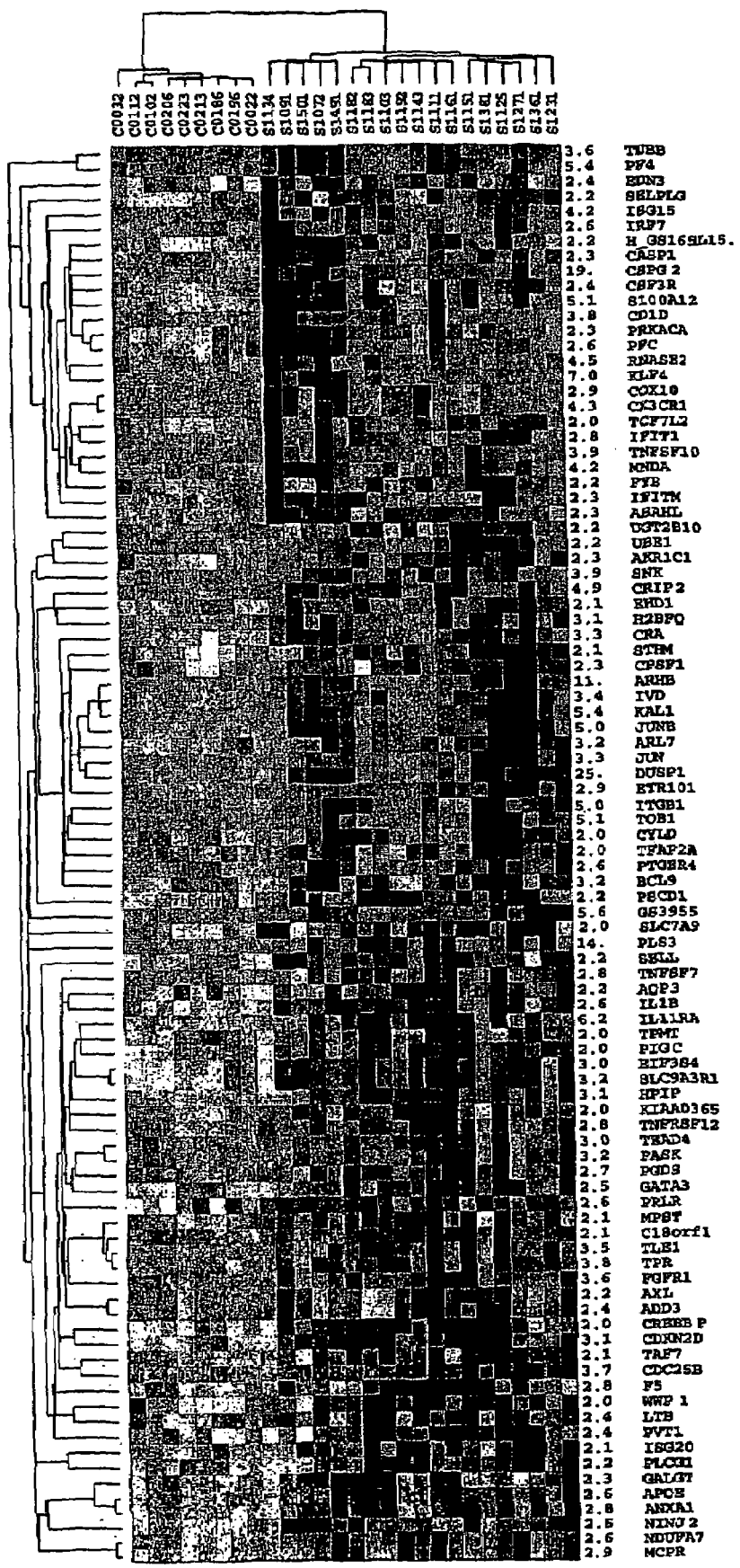
FIG. 2B is the lower portion of the treeview of FIG. 2A.
Figure 3:
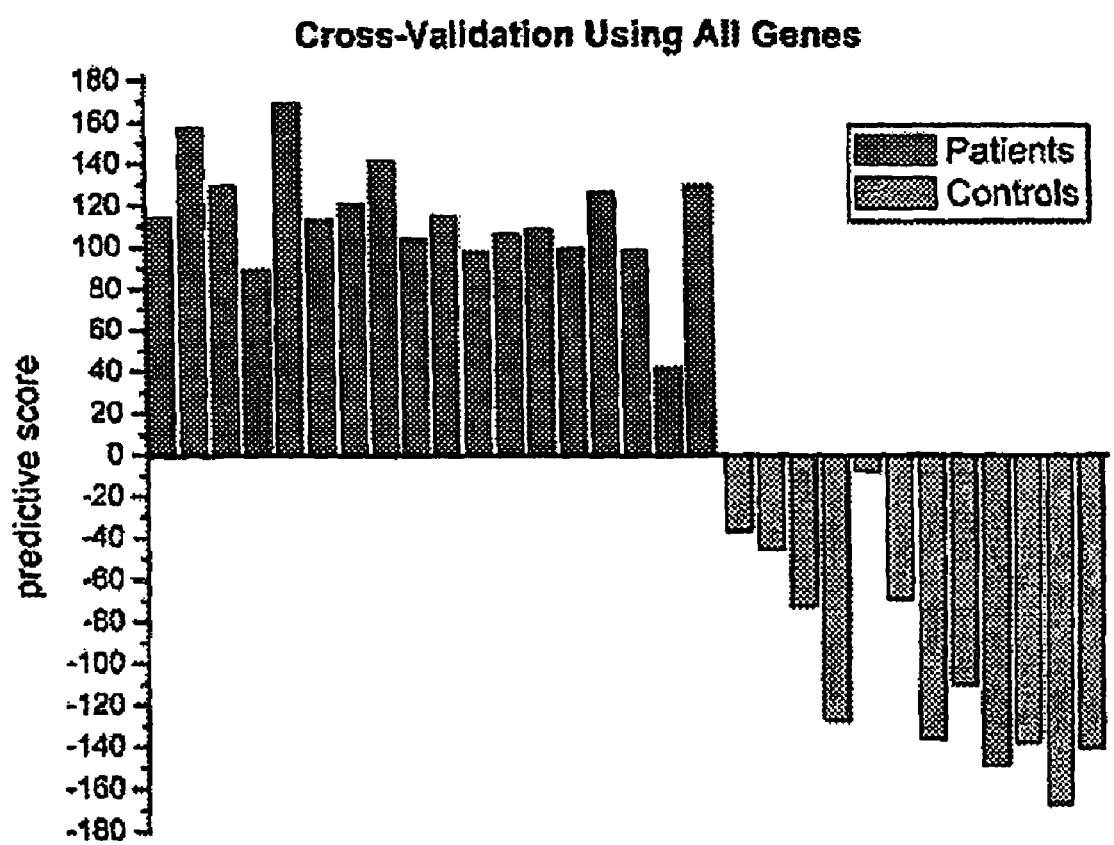
FIG. 3 is a bar graph showing the cross-validation of high SzS patients and normal controls by PDA, using all the genes on HA01-HA03 gene arrays (The Wistar Institute, Philadelphia, Pa.). Positive scores indicate patients. The accuracy of cross validation is 100%.

The treeview of FIG. 2 was prepared as described in Eisen, M. B. et al, 1998 *Proc Natl Acad Sci USA* 95:14863-14868 showing the variation in expression of the 135 p<0.01 significant genes that are either upregulated or downregulated >2-fold in eighteen high tumor burden patients was compared to nine Th2-skewed controls. The significant genes are listed on the right side of the tree view using gene symbols from Source (http://genome-www5.stanford.edu/cgi-bin/SMD/source//BatchSearch). The pale cluster identifies genes which are downregulated and the dark cluster genes which are upregulated in patients versus controls. Values for fold increases or decreases (−) precede the gene symbols.

The most highly changed expression levels are for dual specificity phosphatase 1 (DUSP1), 25-fold overexpressed, and CD40 (TNFRSF5), 7-fold underexpressed. Other genes overexpressed more than 10-fold in patients include versican, a cell surface protein that binds L-selectin and regulates chemokine function (Hirose, J. et al, 2001 *J Biol Chem* 276: 5228-5234.); T-plastin (PLS3), an actin bundling protein not normally expressed in T-cells (Lin, C. S., et al, 1999 *DNA Cell Biol* 18:27-37); and the small GTP-binding protein, RhoB (ARHB), involved in cytoskeleton reorganization and signal transduction (Ridley, A. J. 2001 *Traffic* 2:303-310; Small, J. V. et al, 1999 *Curr Opin Cell Biol* 11:54-60; Narumiya, S. et al, 1997 *FEBS Lett* 410:68-72). In addition, message for the receptor for IL-11 (IL-11R) and the TNF related cytokine, TRAIL (TNFSF10) are significantly increased. IL-11 is a strong inducer of Th2 differentiation and signals the down-regulation of IL-12 (Bozza, M. et al, 2001 *J Interferon Cytokine Res* 21:21-30), both characteristic of Sezary cells. Under-expressed genes include CD26 (DPP4), whose loss has been suggested to be a strong marker for CTCL (Jones, D., et al, 2001 *Am J Clin Pathol* 115:885-892). Both CD8+ α and CD8+ β message levels are also down, consistent with the observed decrease in CD8+ T-cell numbers (Bernengo, M. G., et al, 1998 *Ann Oncol* 9:857-863) with advancing disease. Other significantly downregulated genes include the IL-1 receptors, signal transducer and activator of transcription 4 (STAT4), and the IL-2 receptor beta chain.

Example 2

Validation of Array Results Using Quantitative Real-Time PCR

To determine the accuracy of changes in gene expression reported by the arrays in Example 1, selected genes were assayed by quantitative real-time PCR (QPCR) for the eighteen high Sezary cell samples and nine Th2 controls. The direction of change by PCR was in agreement for every gene tested. Of 32 genes tested, only one gene, PLS3, showed an important difference in the two assays (500-fold up by QPCR and only 14-fold up by array, probably attributable to some cross-hybridization which raised the array control values.

Over the remaining 31 genes, for approximately 75%, the two ratios agreed within a factor of two, the average of the microarray ratio to the QPCR ratio was 0.70, and the median was 0.61. The comparison of the PCR and microarray assay in Table 5 shows that the arrays give a highly reliable estimate of the direction of change in gene expression with a tendency to underestimate quantitative differences.

TABLE 5

Verification of Array Using Quantitative Real-Time PCR

| Genes | | Array Experiment | | | | Real-time Experiment | | | |
|---|---|---|---|---|---|---|---|---|---|
| Name | Symbol | Th2 Mean + SD | Patient Mean + SD | Ratio | P value[a] | Th2 Mean + SD | Patient Mean + SD | Ratio | P value[a] |
| Dual specificity phosphatase 1 | DUSP1 | 0.2 + 0.1 | 3.9 + 2.9 | 25 | <0.001 | 0.1 + 0.1 | 1.8 + 1.5 | 31 | <0.001 |
| Plastin T | PLS3 | 0.7 + 0.2 | 10 + 9.7 | 14 | <0.001 | 0.01 + 0.01 | 3.5 + 6.4 | 479 | 0.034 |
| Rho B | ARHB | 0.3 + 0.2 | 3.4 + 3.7 | 11 | 0.002 | 0.2 + 0.1 | 1.6 + 1.6 | 8 | 0.002 |
| JunB | JUNB | 1 + 0.3 | 4.9 + 3.2 | 5 | <0.001 | 0.3 + 0.2 | 3.1 + 2.9 | 10 | <0.001 |
| Integrin β1 | ITGB1 | 1 + 0.7 | 4.6 + 5.4 | 4.5 | 0.013 | 0.1 + 0.1 | 1.4 + 1.5 | 12 | 0.003 |
| TRAIL/APO-2 ligand | TNFSF10 | 0.7 + 0.2 | 3 + 3.5 | 4.2 | 0.015 | 0.3 + 0.1 | 1.7 + 1.4 | 6 | <0.001 |
| CX3C receptor 1 | CX3CR1 | 0.7 + 0.4 | 3.4 + 3.4 | 4.5 | 0.006 | 0.3 + 0.2 | 2.1 + 2.4 | 8 | 0.004 |
| Interferon-stimulated protein | ISG15 | 1 + 0.3 | 4. + 4.0 | 4.2 | 0.005 | 0.4 + 0.3 | 3.4 + 4.2 | 9 | 0.009 |
| Cyclin-dependent kinase I 2D | CDKN2D | 1 + 0.4 | 2.8 + 1.6 | 2.7 | <0.001 | 0.4 + 0.1 | 1.7 + 0.9 | 4.3 | <0.001 |
| Intercellular adhesion mol. 2 | ICAM2 | 3.7 + 1.2 | 9.8 + 3.8 | 2.7 | <0.001 | 0.4 + 0.2 | 1.4 + 0.8 | 3.3 | <0.001 |
| CD1D | CD1D | 0.4 + 0.1 | 0.9 + 0.7 | 2.6 | 0.005 | 0.1 + 0.1 | 2.4 + 2.5 | 16 | 0.001 |
| GATA3 | GATA3 | 1.3 + 0.6 | 3.2 + 1.6 | 2.5 | <0.001 | 0.3 + 0.2 | 2.2 + 1.5 | 7 | <0.001 |
| Selectin L | SELL | 5.4 + 2.2 | 10.8 + 4.6 | 2 | <0.001 | 0.6 + 0.4 | 1.8 + 1.1 | 2.8 | <0.001 |
| CD44 | CD44 | 13.3 + 3.7 | 7.3 + 3.0 | −1.8 | 0.001 | 2.3 + 2.3 | 1 + 0.6 | −2.3 | 0.188 |
| CD8+α | CD8A | 1.4 + 0.7 | 0.6 + 0.3 | −2.2 | 0.01 | 1.3 + 0.7 | 0.1 + 0.1 | −14 | <0.001 |
| Chemokine (C—C motif) Rec. 1 | CCR1 | 6.8 + 3.6 | 2.7 + 4.4 | −2.5 | 0.019 | 1.4 + 1.0 | 0.9 + 1.4 | −1.6 | 0.277 |
| Signal trans. & act. of trans. 4 | STAT4 | 2.7 + 1.6 | 0.7 + 0.8 | −3.7 | 0.005 | 1.4 + 0.4 | 0.3 + 0.3 | −4.5 | <0.001 |
| Interleukin 1 receptor type II | IL1R2 | 2 + 0.8 | 0.5 + 0.2 | −3.8 | <0.001 | 2.2 + 1.3 | 0.1 + 0.1 | −26 | 0.001 |
| CD8+β | CD8B | 3.7 + 2.2 | 0.7 + 0.3 | −5 | 0.004 | 1.7 + 0.8 | 0.4 + 0.3 | −4.6 | <0.001 |
| CD26 | DPP4 | 1.5 + 0.6 | 0.2 + 0.1 | −7 | <0.001 | 1.5 + 0.9 | 0.1 + 0.1 | −19 | 0.001 |
| CD40 | TNFRSF5 | 3.3 + 1.8 | 0.5 + 0.3 | −7 | <0.001 | 1.9 + 0.9 | 0.3 + 0.3 | −6 | <0.001 |
| Cytochrome P450 1B1 | CYB1B1 | 15 + 13.4 | 1.1 + 1.0 | −13 | 0.015 | 1.7 + 1.3 | 0.2 + 0.2 | −6 | 0.001 |
| Interleukin 1 receptor type I | IL-1R1 | 4.0 + 3.9 | 0.6 + 0.2 | −18 | 0.032 | 2.1 + 1.8 | 0.2 + 0.2 | −11 | 0.014 |

TABLE 5-continued

Verification of Array Using Quantitative Real-Time PCR

| Genes | | Array Experiment | | | | Real-time Experiment | | | |
|---|---|---|---|---|---|---|---|---|---|
| Name | Symbol | Th2 Mean + SD | Patient Mean + SD | Ratio | P value[a] | Th2 Mean + SD | Patient Mean + SD | Ratio | P value[a] |
| IκBα | NFKBIA | 7.2 + 2.9 | 9.5 + 6.2 | 1.3 | 0.193 | 0.5 + 0.4 | 1.1 + 1.6 | 2.2 | 0.135 |
| Rac/Cdc42 GEF 6 | ARHGEF6 | 5.9 2.3 | 7.8 + 2.4 | 1.3 | 0.066 | 7.2 + 2.9 | 7.2 + 2.9 | 2.2 | 0.013 |
| Zinc finger protein 161 | ZNF161 | 2.8 + 0.7 | 3.1 + 0.5 | 1.1 | 0.366 | 1.3 + 1.0 | 1.5 + 1.2 | 1.2 | 0.586 |
| Superoxide dismutase 1 | SOD1 | 14 + 5.2 | 14.8 + 5.8 | 1.1 | 0.737 | 1.1 + 0.9 | 2.4 + 2.4 | 2.2 | 0.051 |
| Cyclophilin A | PPIA | 10.6 + 3.6 | 10.7 + 3.6 | 1 | 0.939 | 1 + 1.3 | 1.6 + 1.2 | 1.7 | 0.207 |
| NFκB1 (p105) | NFKB1 | 2.7 + 0.8 | 2.8 + 1.4 | 1 | 0.875 | 0.7 + 0.6 | 0.5 + 0.3 | −1.4 | 0.408 |
| Maltase-glucoamylase | MGAM 1 | 1 + 0.4 | 0.9 + 0.4 | −1.2 | 0.368 | 0.8 + 1.2 | 1.3 + 1.3 | 1.7 | 0.314 |
| Fas | TNFRSF6 | 1.1 + 0.5 | 0.9 + 0.4 | −1.2 | 0.374 | 0.7 + 0.6 | 0.6 + 0.6 | −1.2 | 0.631 |
| Plastin L | LCP1 | 40.4 + 25 | 24.0 + 11 | −1.7 | 0.095 | 0.9 + 0.4 | 0.9 + 0.3 | −1 | 0.958 |
| CD40 ligand | TNFSF5 | na | na | na | na | 0.3 + 0.1 | 1.5 + 2.0 | 6 | 0.015 |
| IL-18 | IL-18 | na | na | na | na | 1 + 0.9 | 1.5 + 1.0 | 1.5 | 0.22 |
| Fas ligand | TNFSF6 | na | na | na | na | 12. + 0.6 | 0.5 + 0.5 | −2.4 | 0.014 |

[a]Determined by Student's t test.

Example 3

Expression Profiles of a Small Number of Genes Identified by Penalized Discriminant Analysis Correctly Classify High Sezary Patients and Normal Control Samples PDA, as implemented by CLEAVER was used to identify genes with the highest power to correctly distinguish patients from controls. To identify the best genes for distinguishing the two sample classes, the PDA program was trained on the eighteen high Sezary cell samples versus nine Th2-skewed and three untreated controls. Crossvalidation of the samples in these two classes is 100% accurate.

To select the best features for classification a p<0.10 p-value cut-off was applied to eliminate genes that contribute a disproportionate number of false positives. The genes identified by t-test at p<0.10 were used rather than the 385 p<0.01 gene set, in order to include genes with higher variance that might be good class predictors. To assess the total number of genes that were good classifiers, the genes were ranked according to the absolute value of their assigned predictive power. When the logarithm of the predictive power was plotted against the logarithm of the rank, 200 genes were found to have a faster rise in predictive power than in rank. According to Zipf's law (Zipf, G. 1949 *Human Behavior and Principle of Least Effort: An Introduction to Human Ecology* Addison Wesley, Cambridge, Mass.), these 200 genes are expected to most effectively differentiate patients from controls.

As few as four of these genes, for example, either
1) STAT4, TOB1, CD26 and TRAIL, or
2) STAT4, TOB1, SEC61A1 and GS3686, can be used for correct classification.

Figure 4A:
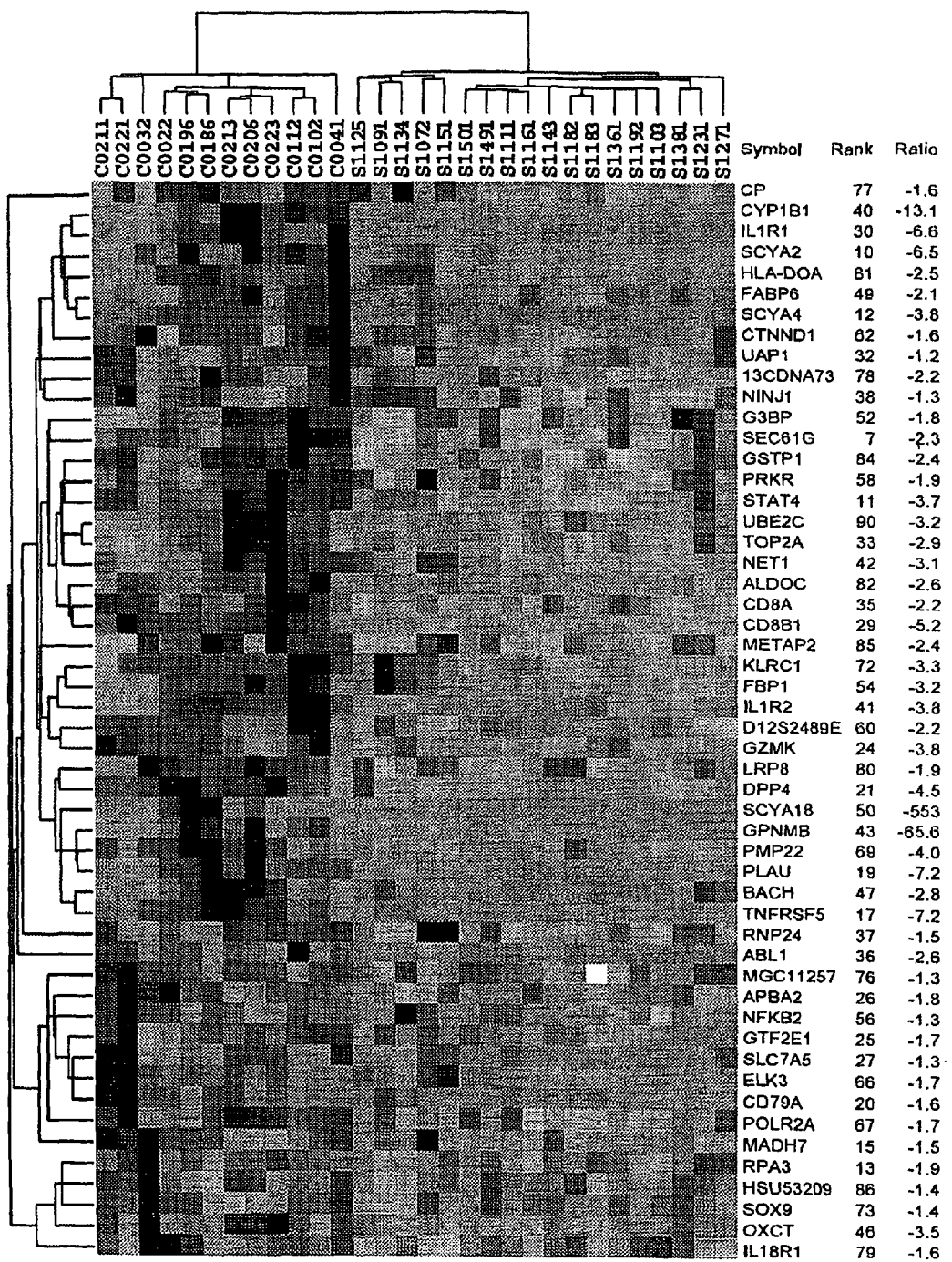
FIG. 4A is the top portion of a treeview showing the 90 best classifiers (e.g., most informative genes) that discriminate high Sezary patients from normal controls. Patient labels (e.g., S1134, etc.), and Th2 controls (e.g., C0032, etc) are listed above the treeview. Genes are listed to the right of the treeview of FIG. 4. The symbols are as described for FIG. 2A.
Figure 4B:
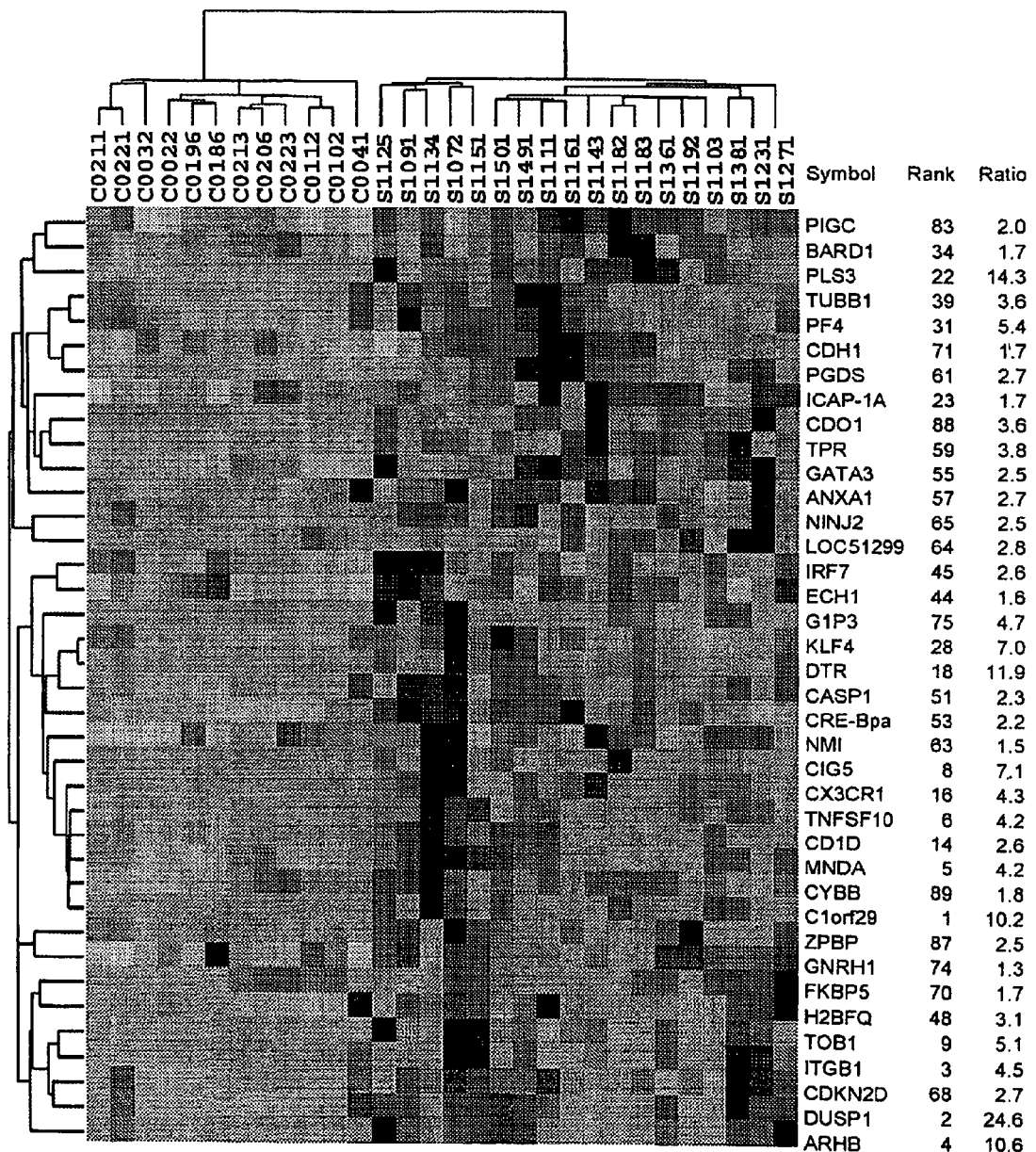
FIG. 4B is the lower portion of the treeview of FIG. 4A.

FIG. 4 lists the 90 best classifiers (e.g., most informative genes) that discriminate high Sezary patients from normal controls using PDA. Rank is a measure of the predictive power and ratio is the average fold change between patients and controls, minus indicates down-regulation in patients. It is important to note that half of the 90 genes are in the p<0.10 data set, but not the more restricted p<0.01 data set.

Classification of Sezary Patients with Low Tumor Burden.

Having achieved a 100% cross-validation on the high blood tumor burden data set, PDA was used to classify a holdout set of 27 patient samples with 5-53% circulating Sezary cells, and eight additional controls, including 1 untreated PBMC and seven Th1 skewed PBMC. The high Sezary cell samples were again used as the training set. Since the additional patients and controls had been analyzed using only the genes on human array HA-03, the 500 genes from HA-03, which were in the p<0.10 data set, were used to train the PDA. To determine the minimal number of genes needed to classify the holdout set, the up and down regulated genes with lower predictive powers, as determined by the training set, were progressively removed. From 40 to 500 genes, the classification is virtually identical, and classification is 100% accurate (data not shown). The 40 genes remaining are listed in Table 6.

When the classification set is reduced to twenty genes (i.e., the top 20 genes listed in Table 6), one patient sample, S139.1, is classified as a control. This patient was subsequently found to suffer from a peripheral T-cell lymphoma resembling Kimura's disease (Gilliam, A. C., and G. S. Wood. 2000 *Semin Cutan Med Surg* 19:133-141), not SS. If the number was reduced to eight genes, one normal control C022-1 is misclassified. To determine whether the twenty genes with the highest predictive powers were uniquely required for accurate classification, the procedure was reversed, and genes with the highest, rather then the lowest, predictive power from the 500 gene data set were sequentially removed. The best 85 genes, equally divided between positive and negative classifiers, can be removed before classification becomes less than 100% (data not shown). This shows that although many more genes are required, the 300 genes with lower predictive powers can still classify accurately.

Figure 5:
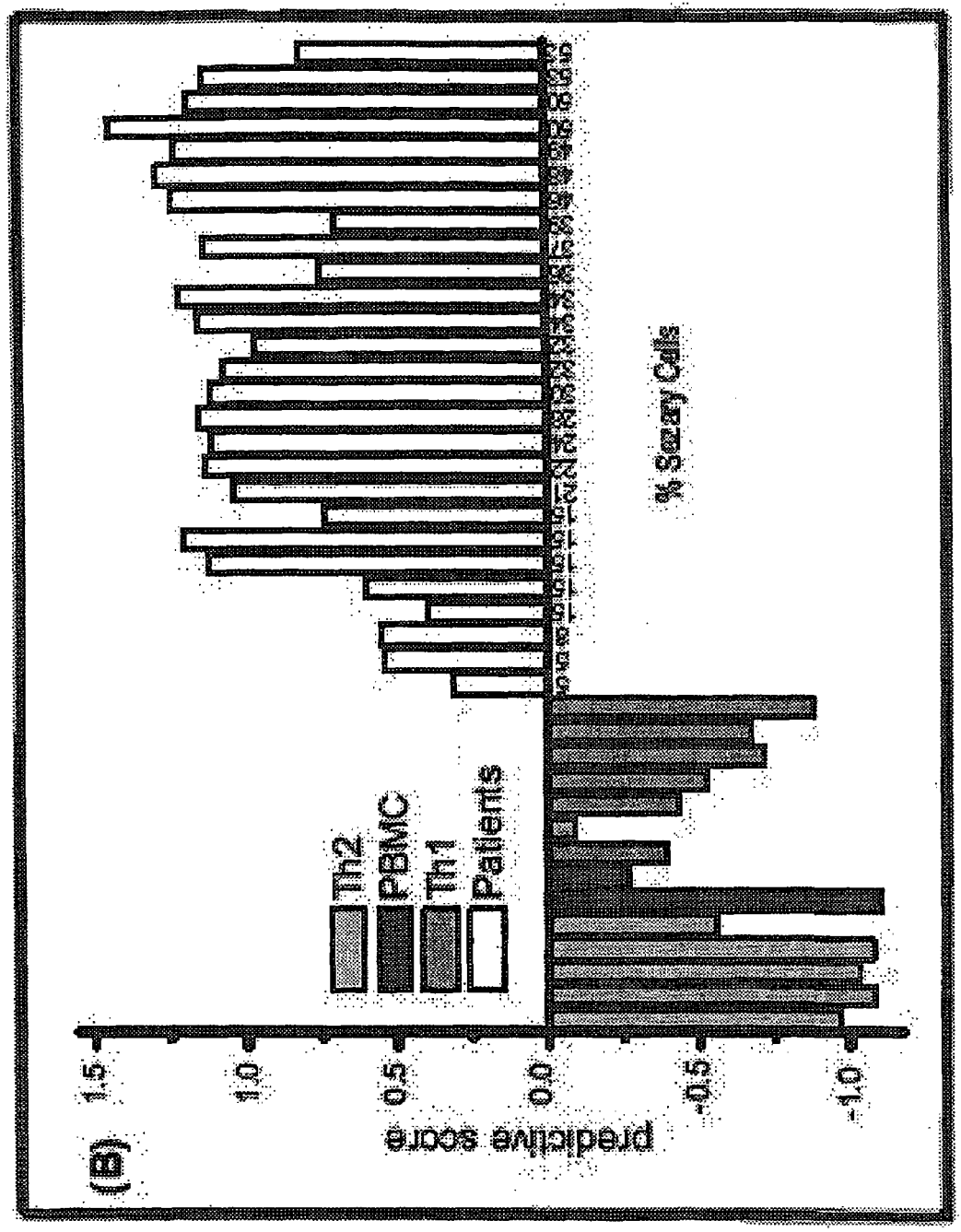
FIG. 5 is a bar graph showing classification of 27 low tumor burden CTCL patients and 14 controls with 40 genes (PBMC=untreated). Negative values indicate the expression profiles that define the negative or control class and positive values identify samples assigned to the positive or patient class. The height of the columns measure how well each samples is classified by the list of 40 genes. Percent Sezary cells are indicated for each sample.

FIG. 5 shows the classification when the number of controls in the training set was reduced to four Th2 and two untreated PBMC controls. This permitted inclusion of more of the Th2 controls in the test set. The 40 genes identified in the training set with fewer controls also perfectly classify the additional 27 CTCL patients and fourteen normal controls. If the number of classifiers was reduced to the top twenty genes, once again the Kimura's disease sample fails to classify as a CTCL patient.

The list of the 40 best classifier genes used for the classification is shown below in Table 6. Genes are listed top to bottom, sorted by the value of their predictive power.

TABLE 6

| Genes Down-Regulated In Patients | Genes Up-Regulated in Patients |
| --- | --- |
| STAT4 | ARHB |
| MGAM | TNFSF10 |
| IL1R2 | CD1D |
| IL1R1 | DUSP1 |
| TNFRSF5 | PLS3 |
| SCYA4 | RBL2 |
| NINJ1 | CYP24 |
| NFKB2 | PDE6C |
| ST13 | SPK |
| ELK3 | GATA3 |
| CYP1B1 | CDKN2D |
| GTF2E1 | NINJ2 |
| APOE2 | DTR |
| KLRC1 | SIRT5 |
| BCL7A | ING1 |
| ABL1 | MAOB |
| FABP6 | AKR1C2 |
| IL2RB | PK-120 |
| POU6F1 | EST |
| AMFR | XPC |

Example 4

Expression Patterns for Clusters of Genes are Found to Vary Coordinately Among CTCL Patients Among the differentially expressed genes in the CTCL patients, overexpressed genes exhibit much greater patient-to-patient variability in expression levels than underexpressed genes do. This is evident from FIGS. 2A-2B. The alternating expression levels across patient samples for some of the top classifiers and highly differentially expressed genes appeared to be highly correlated, for example, RHOB with DUSP1. These correlations are important for the identification of patient subsets. Therefore, clusters of genes with highly correlated expression among the upregulated genes in the p<0.10 data set were identified.

Figure 6:
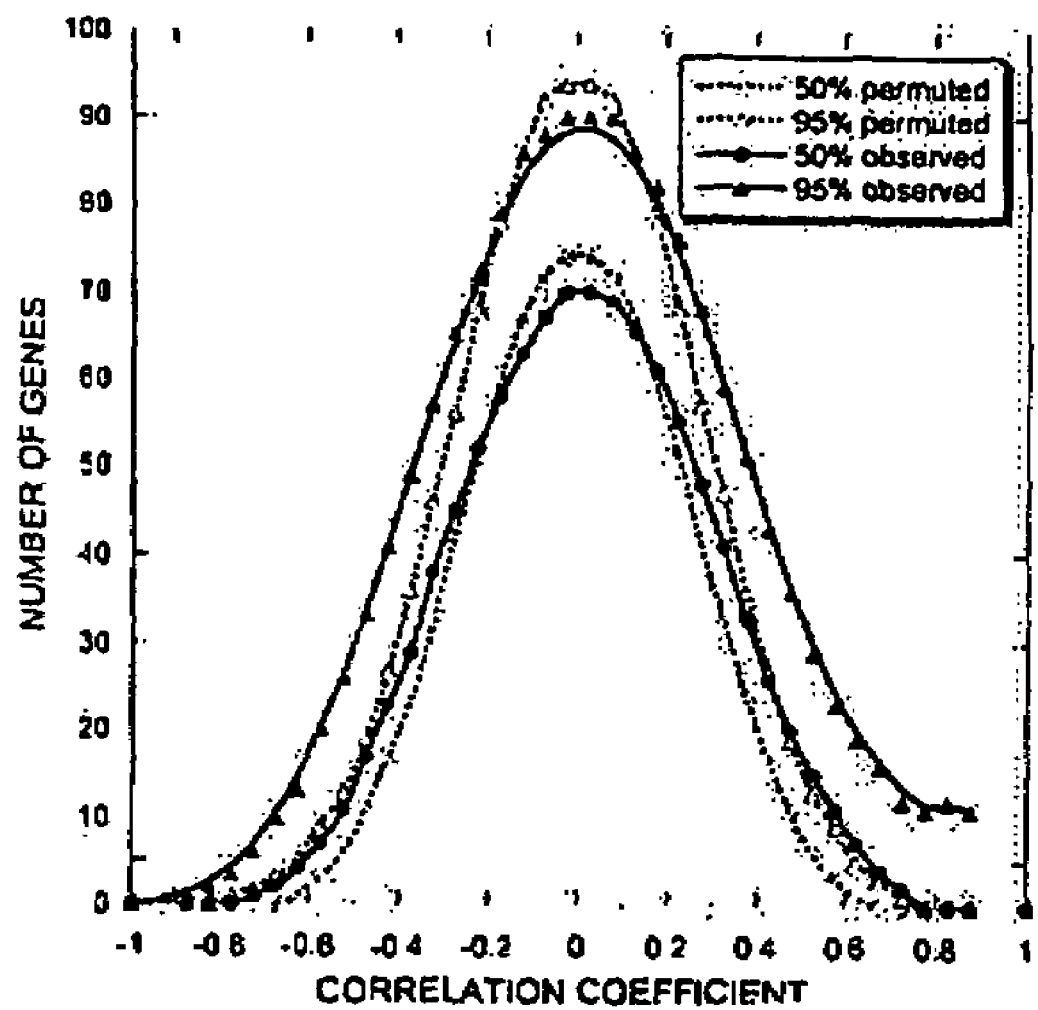
FIG. 6 is a graph showing the distribution of the number of clusters of genes in patients that correlate with an average expression profile calculated for each of 1065 p<0.1 genes: closed symbols, observed expression values; open symbols, permuted expression values; circles, $50^{th}$ percentile of observations; triangles, $95^{th}$ percentile of observations.

To identify an expression cluster for a seed gene, an average profile for this gene was first calculated, and included all the genes that had a correlation with the average profile that was above 0.7 in the cluster. The rationale for using 0.7 as a cutoff is provided in FIG. 6, which compares the degree of correlation of expression values among genes in the observed data set with that in a data set in which the expression values for each gene were randomly permuted. FIG. 6 shows the mean and $95^{th}$ percentile distributions of correlation coefficients, on a data set containing only upregulated genes from p<0.10 data set and the same distributions calculated on the same data set but with the expression values randomly permuted. The distributions of correlated genes obtained on the permuted data set show no genes with correlation coefficients above 0.7, even for the $95^{th}$ percentile of permutations. The distributions obtained on the real data set have a substantial number of genes with correlation coefficients above 0.7, suggesting that they do not belong to a cluster by chance.

Correlated clusters were calculated for all 1065 upregulated genes in the data set and only three clusters were identified that included a significant number of members with correlations greater then 0.7. Many of the genes included are genes from the p<0.01 data set. The cluster identified using the RhoB as the seed gene contains DUSP1, v-JUN, IEP, JunB, JunD, and DNAj, all immediate early genes. The cluster identified with farnesyldiphosphate farnesyltransferase 1 (FDFTase1) as the seed gene includes small GTP binding proteins, vav2 and cdc42, which are modified by this enzyme, but not RhoB which is also modified by FDFTAse1. Finally there is a cluster with CD1D including caspase 1, versican, and S100A12, all included in the p<0.01 gene list.

Example 5

Patients that Survive Less than 6 Months from the Time of Sampling Define a Distinct State of the Disease This example evaluated whether disease progression could be correlated with gene expression patterns. For this analysis, the seventeen high Sezary cell patients were divided into two groups based on observed survival. Six patients that died between one and six months from the time the sample was taken were designated short term survivors (ST); eleven patients who survived more than 12 months (24 months to >5 years) were designated long-term survivors (LT). T-test analysis of the gene expression profiles for the two groups calculated on the 4500 genes analyzed, identified 400 genes that were differentially expressed at p<0.01. Based on 1500 permutations of the patient labels, there is less than a 1% probability that this number of differentially expressed genes could occur by chance.

Figure 7:
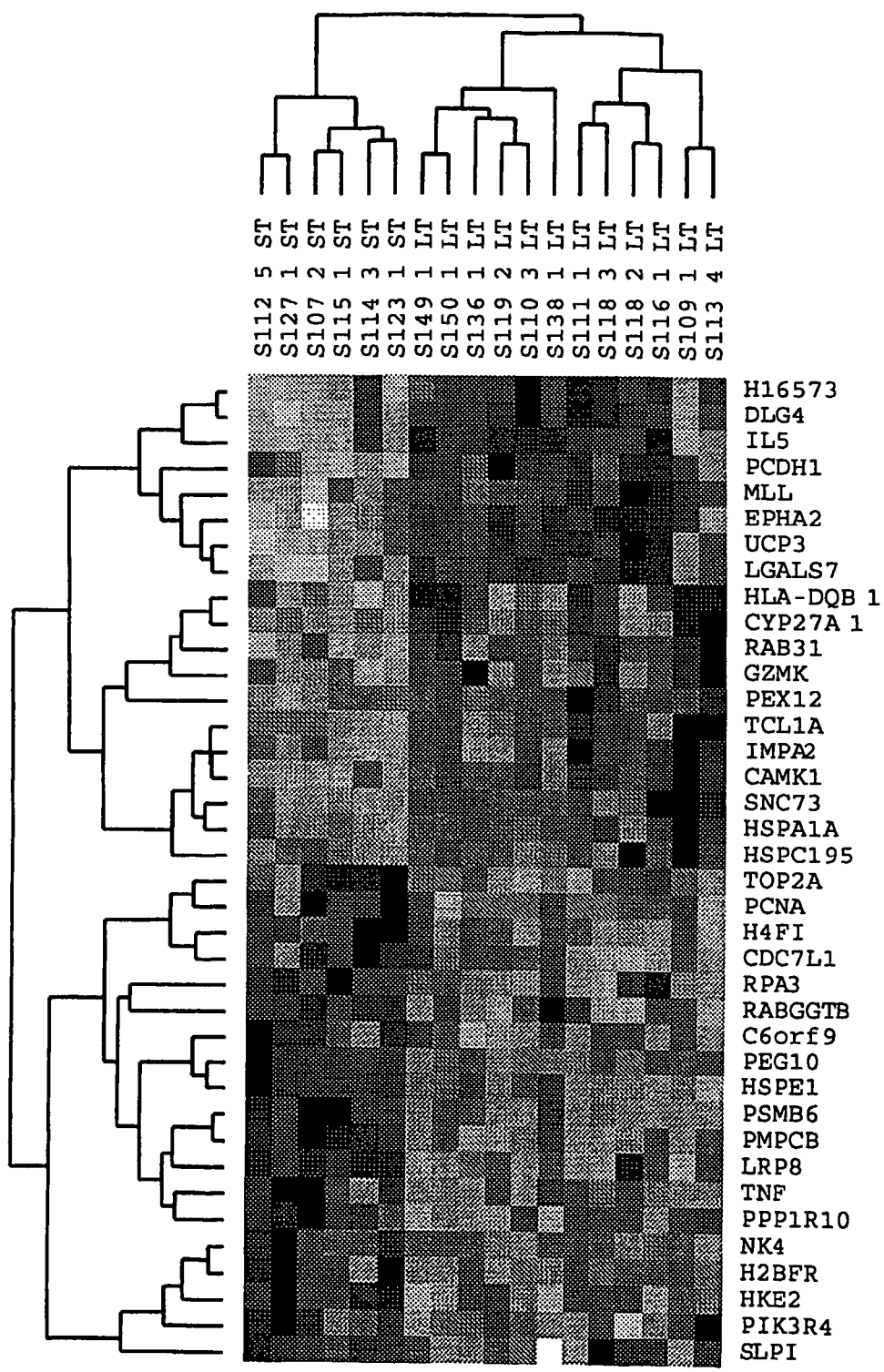
FIG. 7 is a TreeView dendogram showing the 38 genes with highest predictive power (i.e., whose expression levels best distinguish short-term (ST) from long-term (LT) CTCL survivors and the high tumor burden patients that they classify). The genes listed on the right-hand side are listed in order from most overexpressed in LT survivors at the top of the list to least expressed at the bottom of the list.

PDA was applied to the set of 1400 genes that were identified as being differentially expressed at p<0.10 to find the most informative genes for distinguishing between the ST and LT patients. The 38 genes with highest predictive power (i.e., whose expression levels best distinguish short-term (ST) from long-term (LT) CTCL survivors and the high tumor burden patients that they classify) are shown in the TreeView dendogram of FIG. 7.

The analysis was then extended to include patients with low Sezary cell counts, again using the data from only the HA-03 array. The 48 samples in this data set were divided into three groups based on survival: 12 ST (1-6 mos.), 25 LT (more than 40 mos.), and 11 samples with intermediate (MT) survivals (12-40 mos.). The ST and LT groups were used as a training set and the twelve MT samples were withheld for classification.

Figure 8:
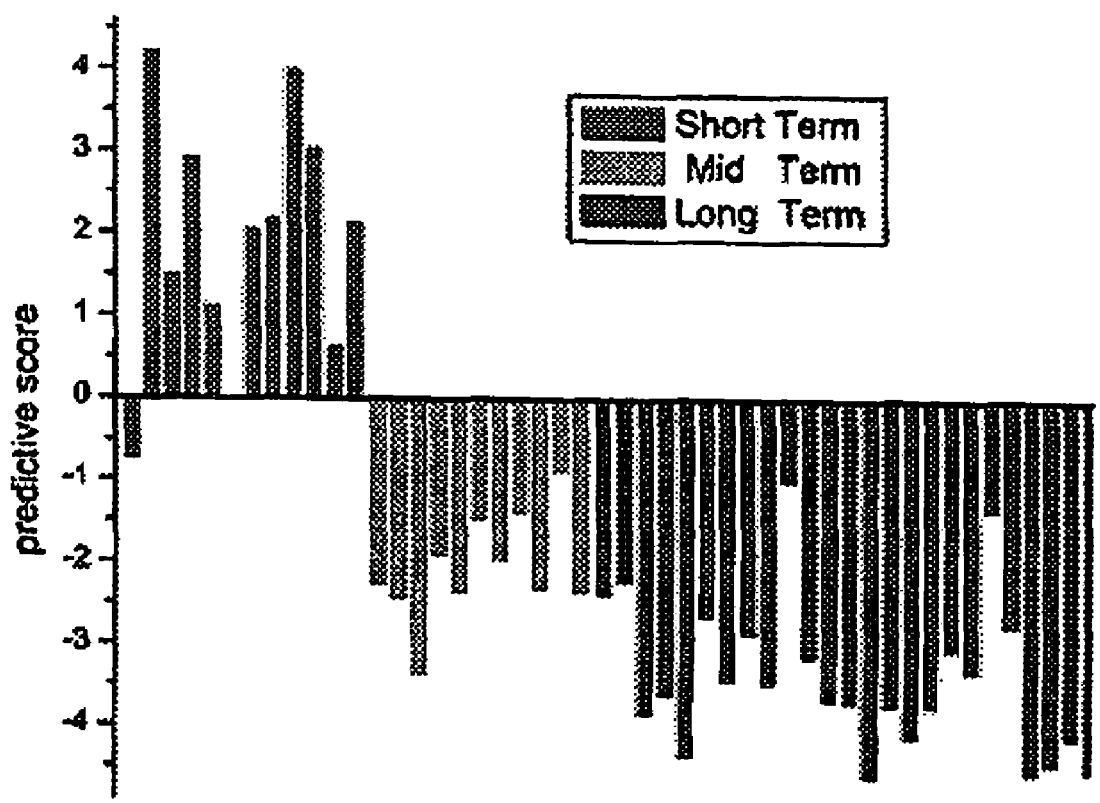
FIG. 8 is a bar graph showing classification of short term (ST), midterm (MT) and long term (LT) surviving CTCL patients using all 2032 genes in the HA03 data set (The Wistar Institute, Philadelphia, Pa.). Eleven ST and 25 LT survivors were used for training. Positive scores indicate classifications as ST patients and negative scores indicate classifications as LT patients.

When all the genes on the HA03 array were used for training, the accuracy of cross validation between ST and LT survivors was greater than 90%, and the MT patients were classified as LT survivors (See FIG. 8). This suggests that the patients that survived less than six months are significantly different from those that survive twelve months or longer.

To determine which genes were the best class predictors, twenty jack knife permutations of PDA were performed on the 37 LT and ST patients with the 2032 genes on HA03. For each permutation a random ⅔ of each class was chosen for training and the remaining ⅓ for validation. The predictive powers of the genes were ranked for each permutation, and the average and standard deviation of the ranks determined. The 40 genes with the highest mean ranks, and the lowest standard deviation of ranks were again used for twenty jack knife permutations of PDA (see Tables 7 and 8 below). The results of 20 classifications using these 40 genes are shown in Table 11. The results show the worst, the best, and the average of the 20 classifications. An accuracy of 75% of ST, or 90% of LT means that 1 of the 4 ST, or 1 of 10 LT patients in the test set was misclassified.

TABLE 7

| Genes Over-Expressed in LT Survivors | Genes Over-Expressed in ST Survivors |
|---|---|
| IL2RB | P4HB |
| TGRBR3 | LY64 |
| BCL2 | HEHU |
| TCN1 | DAD1 |
| SFTPD | BATF |
| HLA-DQB1 | RPA3 |
| ITIH4 | RAD23B |
| PGDS | FLJ32496 |
| ADRB2 | BAX |
| ICSBP1 | CCND2 |
| TCL1A | NRP2 |
| PDCD2 | ENG |
| CHK | HSPE1 |
| HLA-DMB | FKBP5 |
| CDR2 | PASK |
| EIF2B5 | IL9 |
| CD1D | TEAD4 |
| PGRMC1 | AR |
| FGF12B | RARB |
| TRA1 | RPIA |

TABLE 8

Accuracy of Survival Classification Using 20 Permuted Patient Sets

| CLASSIFICATION | Short-Term Survival (%) | Long-Term Survival (%) | COMBINED (%) |
|---|---|---|---|
| Lowest | 75 | 90 | 86 |
| Highest | 100 | 100 | 100 |
| Mean | 91 | 97 | 96 |

This set achieves 100% accuracy in crossvalidation of ST and LT survivors and as few as 10 genes, i.e., the top ten genes in Table 7, five from each column, are sufficient for 100% accurate cross-validation. Thus a small number of genes can be used to distinguish ST survivors from LT survivors despite the fact they vary widely (5 to 99%) in Sezary cell tumor burden and clinical history.

Example 6

Diagnosis of CTCL Patients with High or Low Tumor Burdens by Discriminant Analysis of QPCR Data (DAPD)

In the previous examples, PDA of microarray data was used to identify a subset of genes that could accurately distinguish between SzS patients with 5-99% circulating tumor cells and normal control samples. The 5 genes used in the analysis of this example were selected from a panel of 20 of these genes identified on cDNA arrays, as having high predictive values for making this distinction. The 5 genes selected, and their expression levels relative to controls based on the array data were:

STAT4 (Ratio: −3.7; p=0.0004),

CD1D (Ratio: +2.3; p=0.008),

GATA3 (Ratio: +2.6; p=0.00008),

TRAIL (Ratio: +4.5; p=0.013), and

PLS3 (Ratio: +13; p=0.0007).

STAT4 is the only gene down regulated in patients in this panel. Its loss in $CD4^+$ SzS cells was shown previously in a small number of patients by Western blotting (Showe, L. C. et al, J Immunol, 163: 4073-4079, 1999; Showe II). The remaining 4 genes are all over-expressed in patients relative to controls.

A. Purification of PBMC and Preparation of Samples and Controls

Peripheral blood mononuclear cells (PBMC) were obtained by Ficoll gradient separation from peripheral blood of normal volunteers or SzS patients as described in Example 1. Normal control PBMC were either untreated (UT), or were skewed to Th1 and Th2 phenotypes as previously described in Example 1. Th2 skewed PBMC were used as controls for training. SzS cells closely resemble Th2 T-cells, as mentioned above. The UT and Th1 skewed controls were included in validation sets to provide a more diverse panel of control samples to more stringently test the classification.

Patients and controls from five patient/control groups were divided into several groups in order to have an appropriate balance of patients and various types of controls in both training and validation sets for analysis by microarray and by qPCR (Tables 9 and 10). Training sets were selected from patients with greater than 60% SzS cells, while test sets had patients with 5-62% in order to test the sensitivity of the method.

Group 1 includes 30 samples, 18 patients with SzS cell counts ranging from 60-99% of total circulating lymphocytes, 9 Th2 skewed PBMC (Th2) and 3 UT controls. These samples were used to train the LDA for both array and PCR studies. Groups 2 and 3 include 34 and 48 samples, respectively. Both groups include 26 patient samples with 5-62% SzS cells and 8 controls, primarily Th1 skewed PMBC (Th1). These samples were analyzed by arrays and PCR.

Group 3 also includes an additional 14 control samples only analyzed by PCR. RNA samples analyzed in Groups 1, 2, and 3 were all T7 amplified (Van Gelder, R. N. et al, 1990 Proc Natl Acad Sci USA, 87: 1663-1667). Group 4 includes 16 patients, mostly high SzS cell counts, and 13 controls. These samples are total RNA and were used as a total RNA training set for the samples in Group 5. Group 5 includes 13 patients and 10 controls. It includes an independent set of patient and control samples derived from 3 separate sources with coded identities. PHA indicates that cells were PHA treated for 4 days. N/A means that SzS cell counts were not available.

TABLE 9

Patient Sample Groups 1-5

| Patient | % Sezary Cells | Group | | | | |
|---|---|---|---|---|---|---|
| | | 1 | 2 | 3 | 4 | 5 |
| S104.2 | 15 | − | + | + | − | − |
| S105.2 | 8 | − | + | + | + | − |
| S106.2 | 15 | − | + | + | − | − |
| S107.2 | 97 | + | − | − | + | − |
| S109.1 | 86 | + | − | − | + | − |
| S110.3 | 99 | + | − | − | − | − |
| S111.1 | 75 | + | − | − | + | − |
| S112.3 | N/a | − | − | − | + | − |
| S112.5 | 90 | + | − | − | − | − |
| S113.4 | 75 | + | − | − | + | − |
| S114.3 | 99 | + | − | − | + | − |
| S115.1 | 60 | + | − | − | + | − |
| S116.1 | 90 | + | − | − | + | − |
| S118.2 | 90 | + | − | − | + | − |
| S118.3 | 90 | + | − | − | + | − |

TABLE 9-continued

Patient Sample Groups 1-5

| Patient | % Sezary Cells | Group 1 | 2 | 3 | 4 | 5 |
|---|---|---|---|---|---|---|
| S119.2 | 90 | + | − | − | + | − |
| S120.1 | 5 | − | + | + | − | − |
| S121.1 | 15 | − | + | + | − | − |
| S122.1 | 32 | − | + | + | + | − |
| S123.1 | 91 | + | − | − | + | − |
| S124.1 | 21 | − | + | + | − | − |
| S125.1 | 37 | − | + | + | − | − |
| S126.1 | 34 | − | + | + | − | − |
| S127.1 | 64 | + | − | − | − | − |
| S128.1 | 62 | − | + | + | − | − |
| S129.1 | 50 | − | + | + | − | − |
| S130.1 | 48 | − | + | + | − | − |
| S131.1 | 61 | − | + | + | − | − |
| S132.1 | 84 | − | − | − | − | + |
| S133.1 | 46 | − | + | + | + | − |
| S134.1 | 34 | − | + | + | − | − |
| S135.1 | 32 | − | + | + | − | − |
| S136.1 | 67 | + | − | − | − | − |
| S137.1 | 27 | − | − | − | − | + |
| S138.1 | 79 | + | − | − | − | − |
| S139.1 | 15 | − | + | + | − | − |
| S140.1 | 39 | − | + | + | − | − |
| S141.1 | 53 | − | + | + | − | − |
| S142.1 | 30 | − | + | + | − | − |
| S143.1 | 22 | − | + | + | − | − |
| S144.1 | 40 | − | + | + | − | − |
| S145.1 | 36 | − | + | + | − | − |
| S146.1 | 24 | − | + | + | + | − |
| S147.1 | 53 | − | + | + | − | − |
| S148.1 | 28 | − | + | + | − | − |
| S149.1 | 83 | + | − | − | − | − |
| S150.1 | 71 | + | − | − | − | − |
| S151.1 | N/A | − | − | − | − | + |
| S152.1 | N/A | − | − | − | − | + |
| S153.2 | N/A | − | − | − | − | + |
| S154.2 | N/A | − | − | − | − | + |
| S155.1 | N/A | − | − | − | − | + |
| S156.1 | N/A | − | − | − | − | + |
| S157.3 | N/A | − | − | − | − | + |
| S158.1 | N/A | − | − | − | − | + |
| S159.1 | N/A | − | − | − | − | + |
| S160.1 | N/A | − | − | − | − | + |
| S161.1 | N/A | − | − | − | − | + |

TABLE 10

Control Sample Groups 1-5

| Control | Type | Group 1 | 2 | 3 | 4 | 5 |
|---|---|---|---|---|---|---|
| C002.2 | Th2 | + | − | − | − | − |
| C003.2 | Th2 | + | − | − | + | − |
| C004.1 | UT | + | − | − | + | − |
| C005.1 | UT | − | − | + | + | − |
| C006.1 | UT | − | − | + | + | − |
| C008.1 | PHA | − | + | + | − | − |
| C010.1 | Th1 | − | + | + | − | − |
| C010.2 | Th2 | + | − | − | + | − |
| C011.1 | Th1 | − | + | + | − | − |
| C011.2 | Th2 | + | − | − | + | − |
| C017.2 | Th1 | − | + | + | − | − |
| C017.3 | Th1 | − | + | + | − | − |
| C017.5 | Th2 | − | − | + | + | − |
| C018.1 | UT | − | − | + | − | − |
| C018.3 | Th1 | − | + | + | − | − |
| C018.5 | Th2 | − | − | + | − | − |
| C018.6 | Th2 | + | − | − | + | − |
| C019.4 | UT | − | − | − | + | − |

TABLE 10-continued

Control Sample Groups 1-5

| Control | Type | Group 1 | 2 | 3 | 4 | 5 |
|---|---|---|---|---|---|---|
| C019.6 | Th2 | + | − | − | − | − |
| C020.6 | Th2 | + | − | − | − | − |
| C021.1 | UT | + | − | − | + | − |
| C021.2 | Th1 | − | + | + | − | − |
| C021.3 | Th2 | + | − | − | + | − |
| C022.1 | UT | + | − | − | + | − |
| C022.2 | Th1 | − | + | + | − | − |
| C022.3 | Th2 | + | − | − | + | − |
| C023.1 | UT | − | − | + | − | − |
| C024.1 | UT | − | − | + | − | − |
| C025.1 | UT | − | − | + | − | − |
| C026.1 | UT | − | − | + | − | − |
| C027.1 | UT | − | − | + | − | − |
| C028.1 | UT | − | − | + | − | − |
| C029.1 | UT | − | − | + | − | − |
| C030.1 | UT | − | − | + | − | − |
| C031.1 | UT | − | − | + | − | − |
| C039.1 | UT | − | − | − | − | + |
| C040.1 | UT | − | − | − | − | + |
| C042.1 | UT | − | − | − | − | + |
| C043.1 | UT | − | − | − | − | + |
| C044.1 | UT | − | − | − | − | + |
| C045.1 | UT | − | − | − | − | + |
| C046.1 | UT | − | − | − | − | + |
| C047.1 | UT | − | − | − | − | + |
| C049.1 | UT | − | − | − | − | + |
| C050.1 | UT | − | − | − | − | + |

All samples were collected with informed consent and IRB approval. The method was validated on a set of samples composed of total, rather than amplified RNA. As a final test, the classification was applied to a blinded set of 23 patient and control samples.

B. RNA Isolation and Amplification.

RNA was isolated using Tri-reagent reagent (Molecular Research Ctr., Cincinnati, Ohio) treated with RNAse free DNAse I (Boehringer Mannheim, Indianapolis, Ind.), resuspended in DEPC treated water and concentrations determined spectrophotometrically. RNA integrity was assessed by electrophoresis using SYBR® Green II (Biowhittaker Molecular Applications, Rockland, Me.). 78 total RNA samples (44 patients and 34 controls) were subsequently amplified (aRNA) using a modified Eberwine T7 protocol (Van Gelder, 1990 R. N., et al, *Proc. Natl. Acad. Sc., USA*, 878:1663-1667). See also the internet site at http://cmgm.stanford.edu/pbrown/protocols).

C. cDNA Synthesis.

The cDNAs were generated from 0.5 µg of aRNA or total RNA using Superscript II reagent for 90 minutes at 37° C. in a 15 µL reaction. The reaction mixture contained 150 units Superscript II reagent (Invitrogen Corporation, Carlsbad, Calif.), 1× Buffer (Invitrogen Corporation, Carlsbad, Calif.), 3.3 mM DTT (Invitrogen Corporation, Carlsbad, Calif.), 1 mM dNTP (Promega Corporation, Madison, Wis.), 67 µg/mL oligo-dT (Promega Corporation, Madison, Wis.), 1 µL 10× random decamers (Ambion, Inc., TX.) and aRNA.

D. Quantitative Real Time PCR.

Gene specific primers (IDT, Inc., IA) were designed with the Light Cycler Probe Design Software, Version 1.0 (Idaho Technology Inc., Salt Lake City, Utah) from the sequence of spotted cDNA clones. Primer sequences are shown in Table 11.

TABLE 11

Gene Specific Primers for qPCR

| Symbol | Forward | SEQ ID NO: | Reverse | SEQ ID NO: | Size (bp) | Temp (° C.) |
|---|---|---|---|---|---|---|
| GATA3 | TATCCATCGCGTTTAGGC | 78 | CCCAAGAACAGCTCGTTTA | 79 | 280 | 60 |
| PLS3 | GCTTGACAAAGCAAGAGT | 80 | GCATCTTCCCTCTCATACC | 81 | 300 | 60 |
| STAT4 | TCCTAGAACCTGGNTATTTACAAAG | 82 | GTGTATGCCGGTGTTGA | 83 | 197 | 60 |
| CD1D | TGAGACGCCTCTGTTTC | 84 | ACACCTCAAATACATACCTACT | 85 | 189 | 60 |
| TRAIL | ACGTGTACTTTACCAACGA | 86 | ATGCCCACTCCTTGAT | 87 | 380 | 60 |

PCR was performed in 20 μl in a Light Cycler Instrument (Roche Diagnostics, Mannheim, Germany). The reaction mixture contained 1 μl Platinum Taq (Invitrogen Corporation, Carlsbad, Calif.), 1× Buffer (Invitrogen Corporation, Carlsbad, Calif.), 2.5 mM Magnesium Chloride (Invitrogen Corporation, Carlsbad, Calif.), 1:20000 SYBR Green I reagent (Biowhittaker Molecular Applications, Rockland, Me.), 0.2 mM dNTP (Promega Corporation, Madison, Wis.), 750 μg/mL BSA (Sigma-Aldrich, Inc.), 0.5 μM Primer each and cDNA Template. The cycle parameters were: 94° C. 3 min hot start, 40 cycles of: 94° C. 10 sec, 56° C. or 60° C. 10 sec, 72° C. 25 sec. SYBR Green I fluorescence intensity was measured at the end of each 72° C. extension. Product specificity was checked by melting curve analysis and gel electrophoresis.

E. qPCR Normalization.

Values for fluorescence intensity of each gene for each subject were reported as the ratio of the determined value to that from a standard curve for each gene of serial dilutions of one subject of the day's tests. The training set was normalized to a unit mean. To compare values from different days, determinations from several subjects were repeated and the average values for each gene used to normalize the values from one day to another.

F. Linear Discriminant Analysis.

Supervised classification of samples was carried out using PDA as provided by the CLEAVER website (Hastie, T. et al, Annals of Statistics, 23: 73-102, 1995; and Raychaudhuri, S. TIBS, 19: 189-193, 2001) (http://classify.stanford.edu/documentation.html). Gene expression values for each patient and control array were ranked, and the ranks were input instead of absolute expression values. To obtain the short list of candidate genes for analysis with qPCR, PDA was applied to ranked microarray expression data consisting of all the genes on the arrays, and the genes with the highest "predictive power" (discriminant weight multiplied by standard variation) were selected, as described in the preceding examples. To obtain discriminant functions for expression values obtained from these few genes by qPCR, PDA was applied to the ranked expression data with no penalty value, reducing the procedure to linear discriminant analysis.

G. Classification with 5 Genes using LDA and Array Data.

Figure 9A:
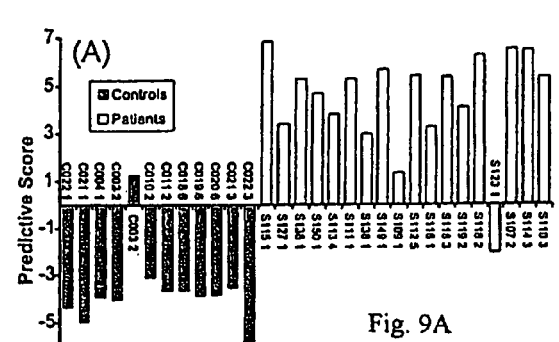
FIG. 9A is a bar graph showing the classification of CTCL and control samples using 5 genes based on microarray data from high-tumor burden patients. Positive predictive scores denote patients (clear bars), negative scores denote controls (grey bars). This graph shows the leave-one-out cross-validation of the training set.
Figure 9B:
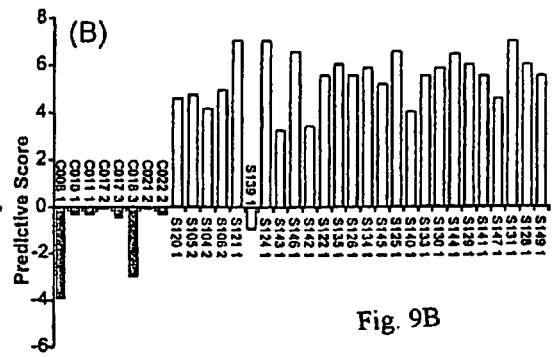
FIG. 9B is a bar graph showing the classification of CTCL and control samples using 5 genes based on validations on microarray data from low tumor burden patients. The labels on the X-axis are individual (S) samples and (C) controls. This graph shows the results of classifying the corresponding validation set.

The ability of the 5 selected genes STAT4, CD1D, GATA3, TRAIL and PLS3, to correctly classify patients and controls was first tested by applying LDA to the expression data from microarrays, using the array data from the previous examples. When trained on the 18 high tumor burden patients and 12 controls in Group I (Tables 9 and 10), LDA was able to correctly classify 28 out of 30 samples. Only one patient and one control were misclassified (93%) by leave-one out cross-validation (FIG. 9A). When tested on the array data from the validation set of 26 low tumor burden patients and 8 controls in Group 2 (Tables 9 and 10), the accuracy of classification is 97% (FIG. 9B). Only one patient with low SzS cell count was misclassified. This shows that the 5 gene classifier trained on high tumor burden patients can also identify low tumor burden patients using LDA and array data.

H. Results: Classification with 5 Genes Using DAPD.

Figure 9C:
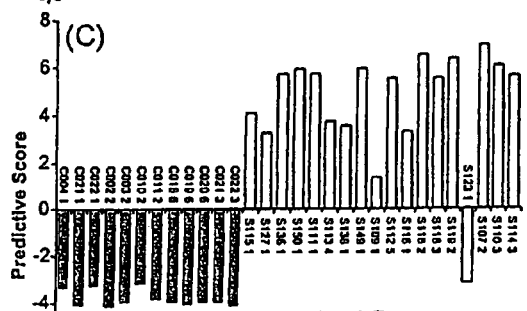
FIG. 9C is a bar graph showing the classification of CTCL samples and controls using 5 genes based on qPCR data from aRNA of high tumor burden patients. Positive predictive scores denote patients (clear bars), negative scores denote controls (grey bars). This graph shows the leave-one-out cross-validation of the training set.
Figure 9D:
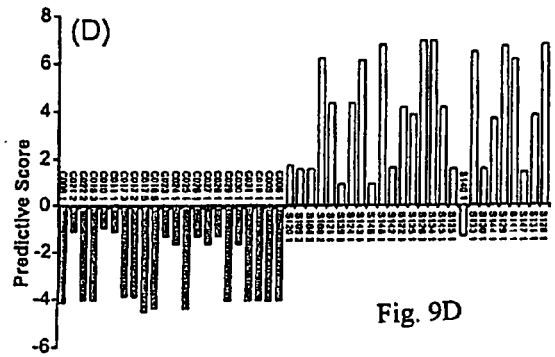
FIG. 9D is a bar graph showing the classification of CTCL and control samples using 5 genes based on validations by qPCR on aRNA from low tumor burden patients. This graph shows the results of classifying the corresponding validation set.

Expression data acquired by qPCR on the same 5 genes from the samples in Group 1 was used to classify patient samples using LDA. When trained on the qPCR data, all but one of the 30 samples is correctly classified by leave-one-out cross validation (FIG. 9C). This is the same patient sample, S123.1 misclassified by the array data. This discriminator was validated on another low tumor burden test set, 26 Sezary patients with Sezary cell counts ranging from 5-62% and 22 normal control samples (Group 3, Tables 9 and 10). Accuracy is 98% and only one patient sample is not classified as CTCL (FIG. 9D). This suggests that genes identified by PDA from cDNA expression arrays are also informative when their relative expression levels determined by qPCR are analyzed by LDA.

I. Results: Classification Using DAPD and Total RNA Samples.

Figure 9E:
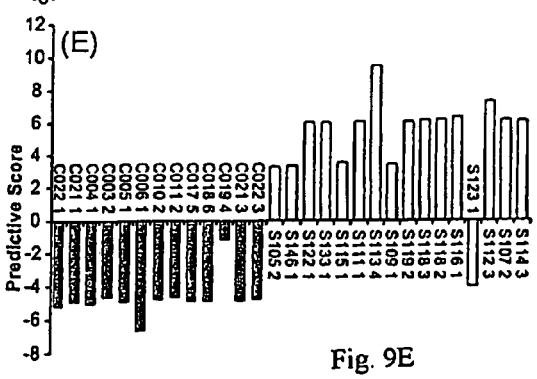
FIG. 9E is a bar graph showing the classification of CTCL and control samples using 5 genes based on qPCR data from total RNA of high tumor burden patients. Positive predictive scores denote patients (clear bars), negative scores denote controls (grey bars). This graph shows the leave-one-out cross-validation of the training set.
Figure 9F:
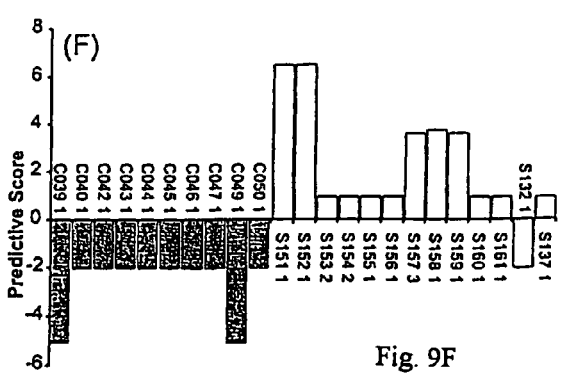
FIG. 9F is a bar graph showing the classification of CTCL and control samples using 5 genes based on validations on qPCR from total RNA for the blinded set. This graph shows the results of classifying the corresponding validation set.

Both the array studies and the qPCR studies described above were carried out using aRNA. RNA amplification was necessary for the array experiments because of the limited amount of patient material available. However the DAPD assay would be much simpler if RNA amplification is not necessary. In order to determine whether genes selected using aRNA could also accurately classify qPCR results obtained from total RNA preparations, 29 samples randomly selected from Groups 1, 2 and 3 (16 patients and 13 controls) for which total RNA was available (Group 4) were trained. 28 of 29 samples (97%) were correctly classified by cross validation (FIG. 9E). The same patient sample, S123.1, is once again misclassified. To test this classifier it was applied to total RNA from a blinded set of 13 patient and 10 normal control samples (Group 5) that were completely independent of the other 4 groups and which had never been analyzed by arrays (FIG. 9F). Twelve of the 13 patient samples and all of the ten controls were correctly classified for an accuracy of 96%.

This example emphasizes the fact that genes selected by array are accurate diagnostic markers for CTCL and are equally accurate when assayed by qPCR. This accuracy is independent of whether aRNA or total RNA is assayed.

To diagnose CTCL, the inventors distinguished patient samples with widely varying percentages of malignant T-cells from the same type of control cells. Therefore almost none of the genes tested in these examples show striking and consistent differences between the two classes of samples that are being compared as described in Gordon et al, cited above.

Only one of the genes tested herein was uniquely expressed in the malignant T-cells. PLS3 (tissue plastin) expression has been confirmed in purified CD4$^+$ SzS cells. In the experiments described herein, PLS3 is expressed only in patient and never in control PBMC, as expression of this gene is normally not found in lymphoid cells. This makes PLS3 an extremely sensitive marker for CTCL. Although its' presence is diagnostic for CTCL in 70% of the patients tested in experiments described herein, the remaining 30% of patients do not express PCR-detectable levels of PLS3. This leaves a significant subgroup of patients that that must be identified by other means. In fact, DAPD using only 4 genes (excluding PLS3) is as accurate as the 5 gene set.

Example 7

Microarray Analysis of Peripheral Blood from Patients with Solid Tumor and Mixed Cell Cancers A. Patients Solid tumor patients comprised 10 non-small cell lung carcinoma, 2 sarcoma, 2 pancreatic carcinoma, and 1 each esophageal, ovarian, small cell, adrenal, and mesothelioma, together with 9 normal controls. Approximately 8000 genes had a complete set of expression values across all patients and controls and these values were used for further analysis.

B. Sample Collection

Sample collection was conducted as follows: Patient and volunteer blood (approx. 10 ml) was collected into Becton-Dickinson Vacutainer™ CPT Mononuclear Cell Preparation tubes. Following centrifugation at 2800 rpm, the buffy coats were removed and washed once with phosphate-buffered saline. The pellets were resuspended in 1 ml of TRIzol™ reagent (Invitrogen) and transferred to 1.5 ml DEPC-treated microfuge tubes. Chloroform (0.2 ml) was added, the samples were vortexed, and centrifuged for 15 minutes at 4° C. at 10,000 rpm. Supernatants were transferred to fresh microfuge tubes and 0.5 ml isopropanol was added. Samples were stored at −20° C. for at least 1 hour.

Following centrifugation, RNA pellets were washed once with 70% EtOH and resuspended in DEPC dH$_2$O. RNA concentrations were determined by spectrophotometry (absorbance at 260 nm).

C. RNA Preparation and cDNA Microarrays

RNA samples were amplified using a modified T7 protocol which can be accessed at the Stanford University microarray protocols website. 0.5 μg amplified RNA target was labeled with P-33 dCTP, 3,000-5,000 Ci/mM using reverse transcriptase. Hybridization was in 2.5 ml Micro-Hyb (Research Genetics) at 42° C. for 18 hours. Filters HA05 and HA06 were sequentially hybridized to the same target RNA. Filters were exposed to a PhosphorImager screen for 4 days, scanned at 50 nm resolution on a Storm PhosphorImager™ apparatus, and quantitated using ImageQuant™ apparatus (Molecular Dynamics). Microarrays were purchased from the Wistar Genomics Facility.

D. Results

Figure 10:
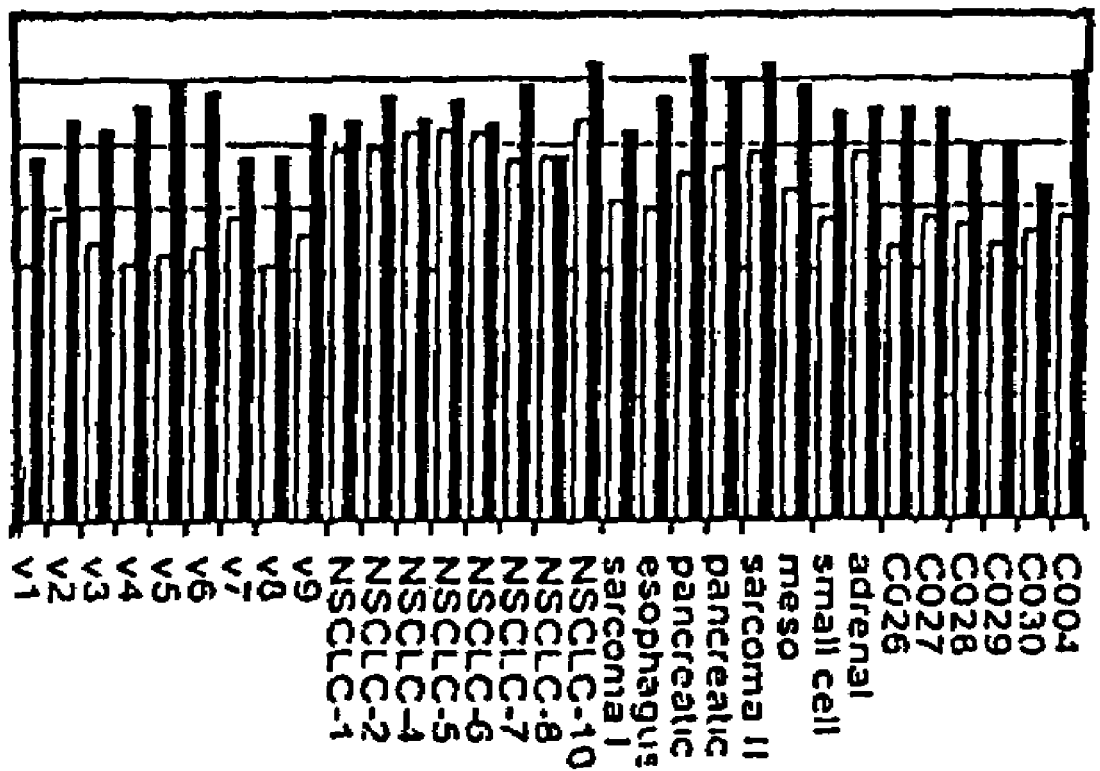
FIG. 10 is a graph depicting gene expression in patient peripheral blood mononuclear cells (PBMC) samples from Example 7. Each patient or control corresponds with two bars. Each individual is indicated as a control (i.e., by a label beginning with C, e.g., C004 or with a V (volunteer), e.g., v3) or a cancer patient. Each cancer patient is identified by cancer type (e.g., adrenal), or by cancer type and number (e.g., NSCLC-4). The most distant samples from the same group are closer than the closest samples from different groups. The clear bars represent the maximum distance to a sample from an individual group. The dark bars represent the minimum distance to a sample from the other group. The most distant samples from the same group are closer than the closest samples from different groups, thereby indicating that this particular gene set can distinguish these different types of samples. Thus, the patients are more similar to each other than to any control.

Analysis of the distance matrix generated using Manhattan or Euclidian distances shows that for most of the samples the most distant member of sample's own group is closer than the closest member of the opposite group (FIG. 10). The only outlier is a lung cancer sample that is positioned exactly halfway between the cancer centroid and control centroid. But this sample is an outlier also relative to the controls: its distance to the control centroid is larger than for any control sample.

The distinction between cancer and control groups using two discriminant methods was confirmed by this data. First, all samples were analyzed with a multiclass shrunken centroids algorithm (Tibshirani, R. et al, 2002 *Proc. Natl. Acad. Sci., USA*, 99:6567-6572). In this analysis, all genes and four samples from each of the two solid tumor groups and control group were used for training and the remaining samples were used as a test set. There is no misclassification of any solid tumor as a control or vice versa. Second, cross-validation using PDA between control and cancer groups is 100% accurate.

Figure 11:
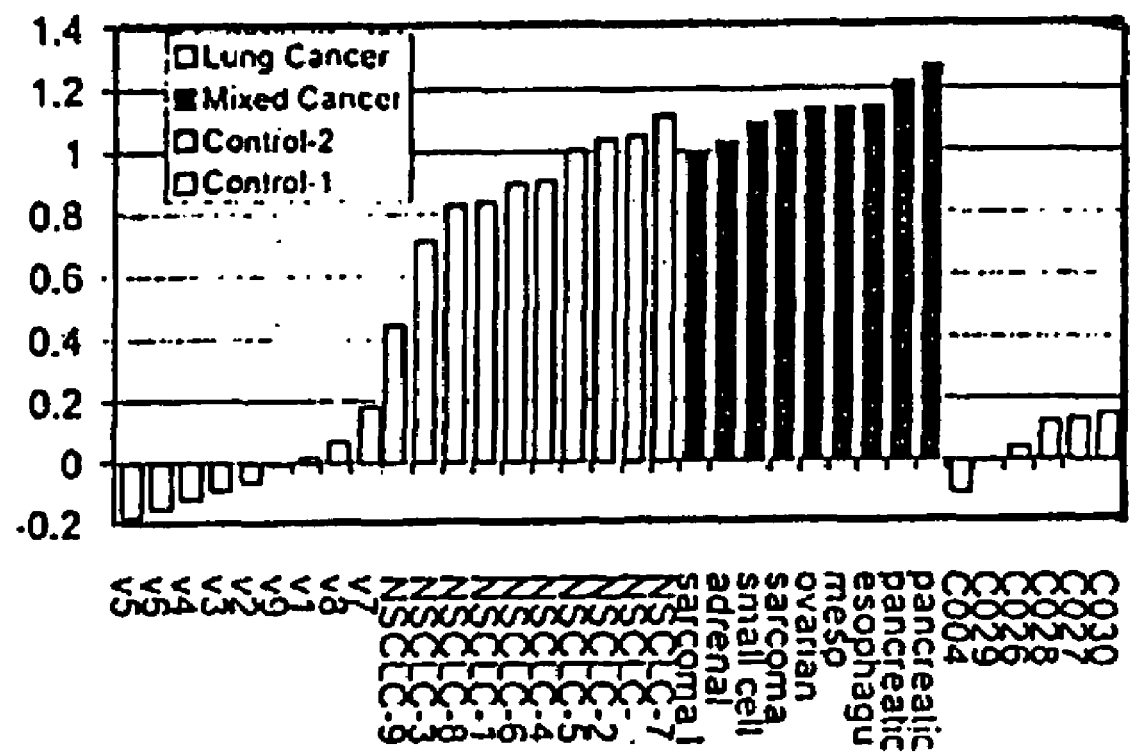
FIG. 11 is a bar graph showing the relative changes in patient's PBMC as determined by the projection on the Control-Cancer Axis for patient samples as described in Example 7.

To estimate the extent of changes in individual patient samples compared to the control group, the following three metrics were used:

(1) Normalized and shrunken distance to control centroid;

(2) Predictive scores for each patient obtained with PDA crossvalidation;

(3) Projection of each sample on the Average Control-Average Cancer vector (see FIG. 11). Metrics 2 and 3 gave similar results.

Several methods were employed to pick out the most informative genes. Although simple t-test between patients and controls identified a substantial number of differentially expressed genes, it was not used as a primary metric because of the substantial variance in the patient group. Indeed, the average distance between cancer samples was observed to be much greater than the average distance between normal controls. The distribution of variance in gene expression is the lowest in the two sets of healthy controls, and the largest in lung adenocarcinomas and a group of "mixed cancers". Therefore, only the variance in the control group was used to normalize the changes in gene expression. Genes were sorted by median Z score in the patient group, relative to the control centroid. Alternatively discriminant loadings from penalized discriminant analysis (PDA) classification of Controls vs Patients was used.

To reduce the variance in the most informative genes, the patient samples that were least advanced in the disease progression as described above were removed. Finally, the genes known to be expressed primarily in cytotoxic T-cells and NK cells were selected and found to be significantly down-regulated.

Drastic changes were observed in gene expression from PBMC of cancer patients compared to normal controls. These changes are much greater than both the noise level and biological variability of normal samples. The changes associated with disease progression were variable among patients and presented the main source of variance in the patient group.

Several methods were used to estimate the extent of disease progression. All of the methods used show that lung carcinoma patients have less change and are more variable as a group than the "mixed cancer" group, which contains many different kinds of cancers. The clinical progression of the patients is followed-up to determine if there is a correlation between outcome and level or type of observed changes in gene expression.

The changes of gene expression that are expected in the cancer patients can be associated with either changes in the cell composition or changes in gene expression in the existing PBMC subpopulations. These data suggest that both are taking place and that changes in cell composition are not the main driving factor. As indicated in Table 12 below, NK and Cytotoxic T-cells genes are significantly downregulated. The most significantly downregulated genes according to median Z test are the Growth Genes.

TABLE 12

| NK and CTL Cytotoxic Genes | t-test | Median Z score | Growth Genes | t-test | Median Z score |
| --- | --- | --- | --- | --- | --- |
| FCGR3A | 6.59E−06 | −15.2611 | PTMA | 7.36E−08 | −75.4871 |
| GNLY | 4.83E−08 | −11.7988 | HNRPA1 | 2.78E−10 | −37.839 |
| PRF1 | 2.06E−05 | −8.43536 | RPL41 | 1.91E−07 | −20.4659 |
| CD8A | 3.11E−09 | −6.84261 | SERPINB6 | 1.1E−07 | −17.6533 |
| CD2 | 3.44E−06 | −6.28723 | LDHA | 5.38E−13 | −15.2629 |
| IL2RG | 1.22E−06 | −5.50725 | TACC1 | 4.02E−09 | −14.7357 |
| GZMK | 0.000137 | −5.26209 | ARPC3 | 8.56E−07 | −12.9633 |
| ITGAM | 3.89E−07 | −5.25155 | CDC25B | 2.16E−06 | −12.824 |
| PFN1 | 1.78E−09 | −3.64608 | CX3CR1 | 2.23E−06 | −12.015 |
| TIA1 | 0.003585 | −3.31555 | LDHB | 7.67E−10 | −11.4787 |
| GZMB | 1.93E−06 | −2.27722 | HNRPA2B1 | 1.34E−07 | −11.3855 |
| IL2RB | 0.000158 | −2.09404 | CDC25A | 9.08E−08 | −11.2665 |

Example 8

Preliminary Analyses of PBMC from Patients with Lung Tumors and Various Other Types of Cancerous Solid Tumors To test the characteristics of PBMC from patients with solid tumors, 19 frozen archived samples of these cells were obtained from phase II clinical trials to compare with PBMC from 9 corresponding healthy volunteers (volunteers 1) and 6 of control PBL from CTCL studies (volunteers 2). RNA from these samples was prepared and compared with expression profiles of the amplified P-33 labeled targets using the methods developed by the inventors in studying CTCL. Each target was probed with two 9,600 gene cDNA arrays carrying a total of 16,000 unique genes, HA05 and HA06 (Wistar Genomics Facility).

Most of the specimens were from patients who had no treatment prior to sampling. However, the supervised classification algorithms detected no significant differences between samples from treated and untreated patients. Ten of the specimens were from patients with non-small-cell lung adenocarcinoma (NSCLC), while the remainder was from a variety of different sarcomas and carcinomas (Table 13).

TABLE 13

Subjects for analysis of gene expression of peripheral blood mononuclear cells from patients with solid tumors.

| Subject | Number |
| --- | --- |
| Non small cell lung carcinoma | 10 |
| Soft tissue sarcoma | 2 |
| Pancreatic | 2 |
| Esophageal | 1 |
| Adrenal | 1 |
| Small cell | 1 |
| Ovarian | 1 |
| Mesothelioma | 1 |
| Volunteers 1 | 9 |
| Volunteers 2 | 6 |

Two supervised multivariate classification techniques were used, i.e., multiclass Shrunken Centroids (Tibshirani et al, cited above) and 2-class Penalized Discriminant Analysis (PDA) (Raychaudhuri, S. 2001 *TIBS* 19:189-193) to compare the expression profiles of the tumor samples to normal controls, and to each other.

The degree of disease progression was estimated by finding the projection of each sample on an AverageControl-AverageCancer Vector. The calculation was done as follows:

1) Normalized median density values for each spot (NMD) were converted to Ranks and Average vectors were found for each group by averaging the gene ranks in each class;

2) Average Control-Average Cancer vector was found by subtracting each Average Cancer vector from the corresponding Average Control vector;

3) Average Control was subtracted from every sample vector;

4) Scalar multiplication was performed on Average Control-Average Cancer and Average Control-sample vectors;

5) The result was divided by the length of Average Control-Average Cancer vector.

Figure 12:
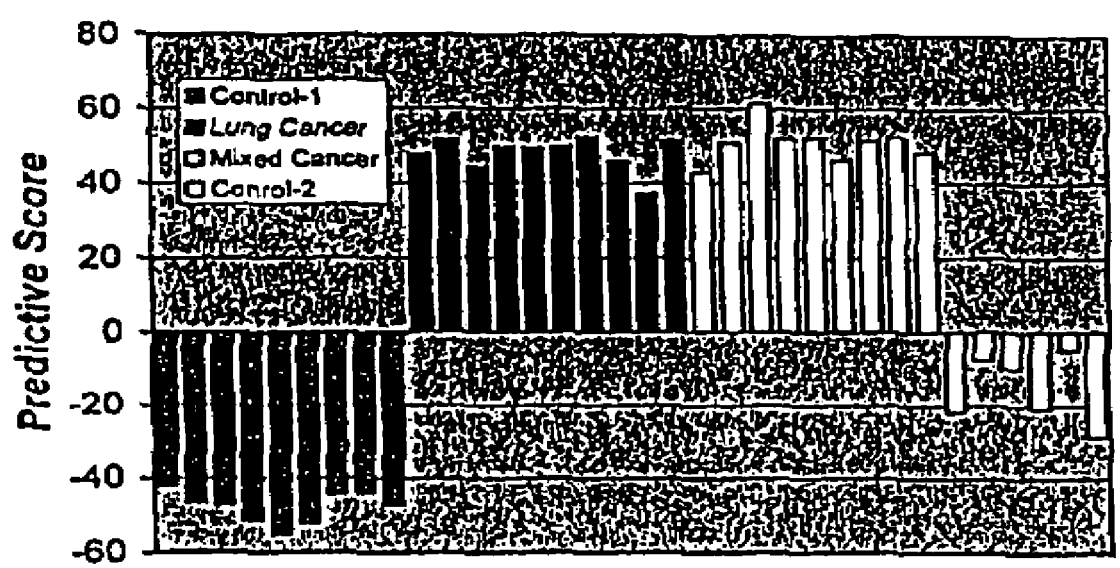
FIG. 12 is a bar graph showing predictive scores for four groups of samples: two groups of controls and two groups of cancers. Predictive scores were generated by Penalized Discriminant Analysis (PDA), which used Control-1 and Lung Cancer groups for training.

The results are summarized as follows: Using the expression profiles of 12,000 significantly expressed genes, the PDA program was trained to distinguish between the lung cancer patients and one group of healthy donors. When the profiles were tested by cross-validation, the lymphocytes were distinguished from every tumor patient from those of all of the 15 healthy controls (FIG. 12).

Relative down regulation of many genes associated with a pro-inflammatory or Th1 response and genes associated with cell growth and division (energy production, actin remodeling, mitosis) were found in the PBMC from the patient samples during a search for function of genes differentially expressed between cancer patients and controls. There appears to be a general suppression of the cells or genes required for an inflammatory response. See, e.g., Tables 14 through 16. Table 14 below lists inflammatory genes differentially expressed between all cancer patients and controls. The ranks are the position of each gene in the complete list of 12,000 genes, where 1 is the most highly overexpressed and 12,000 is the most highly under expressed in patients vs. controls. Table 15 below lists growth-related genes differentially expressed, i.e., down-regulated, between cancer patients and controls. Table 16 below lists growth-related genes differentially expressed, i.e., up-regulated, between cancer patients and controls.

TABLE 14

| Spot | Gene name | Symbol | t-test | Median Z |
|---|---|---|---|---|
| 9055 | Fc fragment of IgG, IIIa, receptor for (CD16) | FCGR3A | 6.59E−06 | −15.2611 |
| 2343 | Granulysin | GNLY | 4.83E−08 | −11.7988 |
| 6595 | Perforin, mRNA sequence | PRF1 | 2.06E−05 | −8.43536 |
| 4977 | CD8 antigen, alpha polypeptide (p32) | CD8A | 3.11E−09 | −6.84261 |
| 195 | CD2 antigen (p50) | CD2 | 3.44E−06 | −6.28723 |
| 6976 | interleukin 2 receptor, gamma | IL2RG | 1.22E−06 | −5.50725 |
| 4904 | granzyme K (serine protease, granzyme 3;) | GZMK | 0.000137 | −5.26209 |
| 7772 | integrin, alpha M (CD11b (p170) | ITGAM | 3.89E−07 | −5.25155 |
| 1333 | profilin 1 | PFN1 | 1.78E−09 | −3.64608 |
| 13269 | TIA1 cytotoxic granule RNA binding protein | TIA1 | 0.003585 | −3.31555 |
| 190 | granzyme B (granzyme 2) | GZMB | 1.93E−06 | −2.27722 |
| 8675 | interleukin 2 receptor, beta | IL2RB | 0.000158 | −2.09404 |

TABLE 15

| Spot | Gene Name | Symbol | t-test | Median Z |
|---|---|---|---|---|
| 13563 | heterogeneous nuclear ribonucleoprotein A1 | HNRPA1 | 2.78E−10 | −37.839 |
| 568 | ribosomal protein L41 | RPL41 | 1.91E−07 | −20.4659 |
| 3046 | serine proteinase inhibitor, B, member 6 | SERPINB6 | 1.1E−07 | −17.6533 |
| 14889 | lactate dehydrogenase A | LDHA | 5.38E−13 | −15.2629 |
| 5708 | actin related protein 2/3 complex, subunit 3, 21 kDa | ARPC3 | 8.56E−07 | −12.9633 |
| 2532 | cell division cycle 25B | CDC25B | 2.16E−06 | −12.824 |
| 2827 | chemokine (C—X3—C motif) receptor 1 | CX3CR1 | 2.23E−06 | −12.015 |
| 3968 | lactate dehydrogenase B | LDHB | 7.67E−10 | −11.4787 |
| 1302 | heterogeneous nuclear ribonucleoprotein A2/B1 | HNRPA2B1 | 1.34E−07 | −11.3855 |
| 15426 | cell division cycle 25A | CDC25A | 9.08E−08 | −11.2665 |
| 1946 | profilin 1 | PFN1 | 6.94E−10 | −11.0253 |
| 13627 | SOCS box-containing WD protein SWiP-1 | WSB1 | 1.9E−08 | −10.8725 |
| 6518 | ARP1 homolog A, centractin alpha | ACTR1A | 1.54E−06 | −10.7297 |
| 3724 | G protein-binding protein CRFG | CRFG | 7.56E−11 | −10.3535 |
| 9095 | caspase 1, | CASP1 | 1.07E−05 | −10.0506 |
| 446 | endothelial G-protein-coupled receptor, 1 | EDG1 | 4.35E−10 | −9.93481 |
| 6556 | heterogeneous nuclear ribonucleoprotein H1 (H) | HNRPH1 | 4.89E−07 | −9.90735 |
| 16602 | F-box and leucine-rich repeat protein 5 | FBXL5 | 2.07E−07 | −9.75567 |
| 14119 | transforming growth factor, beta receptor III | TGFBR3 | 4.89E−09 | −9.5726 |
| 8855 | SMT3 suppressor of mif two 3 homolog 2 (yeast) | SMT3H2 | 1.03E−08 | −9.46914 |
| 12173 | ATP synthase, H+ | ATP5G3 | 3.91E−08 | −9.36888 |
| 1567 | actin related protein 2/3 complex, subunit 4, 20 kDa | ARPC4 | 5.79E−11 | −9.15806 |
| 2676 | lamin B receptor | LBR | 1.38E−14 | −9.04762 |
| 4018 | heat shock 60 kDa protein 1 (chaperonin) | HSPD1 | 2.68E−07 | −9.04721 |
| 3637 | WAS protein family, member 2 | WASF2 | 1.05E−08 | −9.03856 |
| 9591 | ribosomal protein L23 | RPL23 | 1.42E−06 | −8.78879 |
| 14881 | utrophin (homologous to dystrophin) | UTRN | 5.18E−09 | −7.94632 |
| 19076 | CD53 antigen | CD53 | 5.84E−11 | −7.92603 |
| 4753 | ubiquitin-activating enzyme E1-like | UBE1L | 5.48E−07 | −7.83583 |
| 12810 | microtubule-associated protein 1 light chain 3 alpha | MAP1LC3A | 3.87E−06 | −7.7265 |
| 1496 | mitogen-activated protein kinase, kinase 1 | MAP2K1 | 5.68E−09 | −7.71345 |
| 1005 | ribosomal protein L10 | RPL10 | 1.42E−08 | −7.68992 |

TABLE 16

| Spot | Gene Name | Symbol | T-test | Median Z |
|---|---|---|---|---|
| 1986 | synovial sarcoma, X breakpoint 4 | SSX4 | 1.38E−07 | 7.125294 |
| 4926 | paired basic amino acid cleaving system 4 | PACE4 | 1.35E−10 | 5.983932 |
| 8805 | MAD1 mitotic arrest deficient-like 1 (yeast) | MAD1L1 | 5.47E−05 | 5.89851 |
| 2971 | mitogen-activated protein kinase 10 | MAPK10 | 5.18E−06 | 5.681738 |
| 4660 | cyclin K | CCNK | 1.09E−07 | 5.630986 |
| 2393 | DNA-binding transcriptional activator | NCYM | 4.28E−06 | 5.603383 |
| 872 | APEX nuclease (DNA repair enzyme) 1 | APEX1 | 1.7E−09 | 5.424017 |
| 487 | citron (rho-interacting, serine/threonine kinase 21) | CIT | 2.49E−06 | 5.231441 |
| 6061 | transducin-like enhancer of split 1 | TLE1 | 2.87E−08 | 4.780921 |
| 7764 | ret finger protein | REP | 8.91E−06 | 4.122543 |

Figure 14:
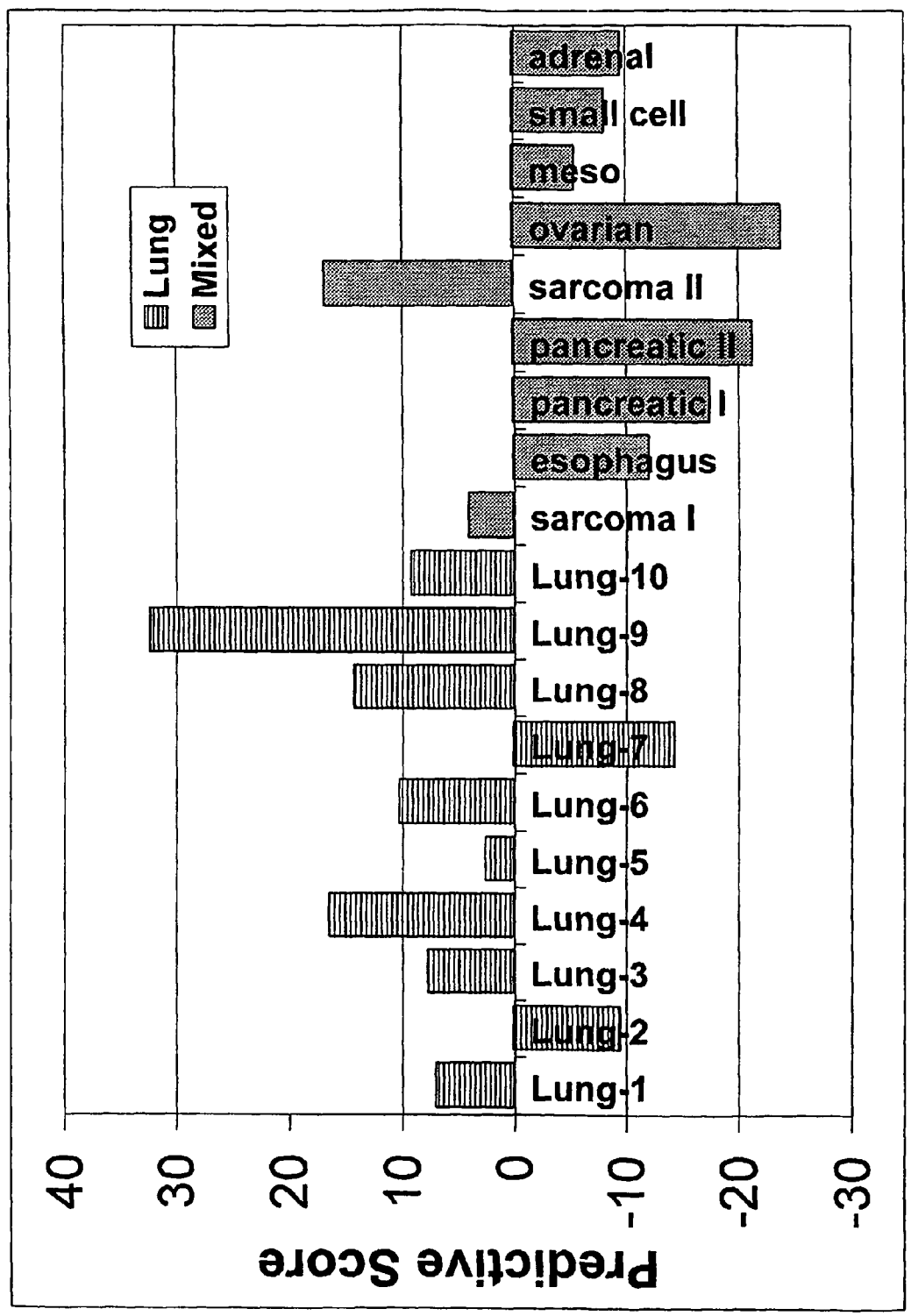
FIG. 14 is a bar graph depicting the results of cross-validation with PDA between Lung Cancer groups (first 10 bars from the Y-axis) and Mixed Cancer groups (last 9 bars from the Y-axis). The predictive score for each sample was obtained by setting this sample aside and using the rest of the samples for training.

Eleven genes known to be important for a cytotoxic immune response and shown by SAGE analysis to be highly expressed in NK cells and CD8 cytotoxic T-cells (Obata-Onai, A., et al, 2002 Int Immunol 14:1085-1098) were used alone to perform an unsupervised hierarchical clustering of the patient and control samples. With a single exception, the patient samples cluster apart from the controls. See the treeview cluster of FIG. 13. To test the ability of PDA to distinguish one type of cancer from other cancers, the lung cancer samples were trained against all the other cancers taken as a group. When tested, 80% of the lung cancers were properly classified by leave-one-out cross-validation, as were 7 out of 9 of the mixed cancers (FIG. 14). The results of cross-validation with PDA between Lung Cancer and Mixed Cancer groups are shown in the FIG. 15. The predictive score for each sample was obtained by setting this sample aside and using the rest of the samples for training.

Figure 15:
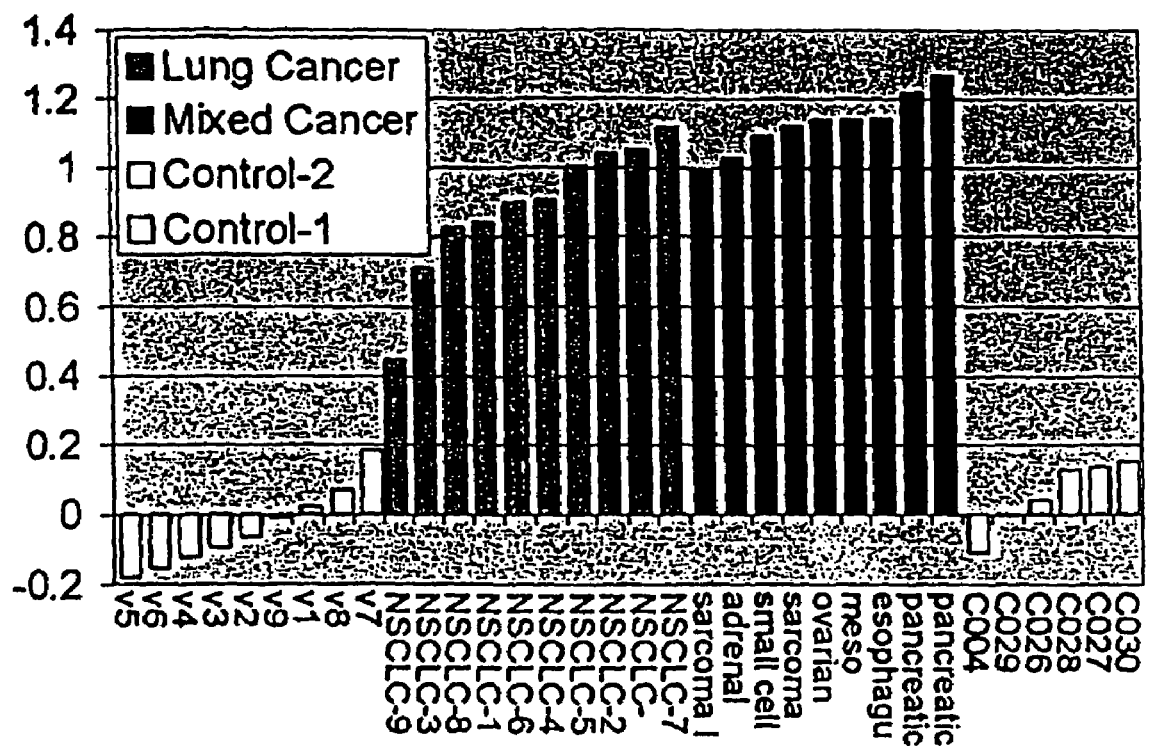
FIG. 15 is a bar graph showing that changes in immune gene expression of each sample are relative to the difference between the average patient and average control. Individual patients are represented along the X-axis as described in FIG. 10. The bars labeled v1 to v9 are one group of control patients. The bars labeled C004 and C026-C030 are a second control group. The bars labeled NSCLC to NSCLC-9 are a lung cancer group. The bars labeled with different cancers represent a Mixed Cancer group.
Figure 16:
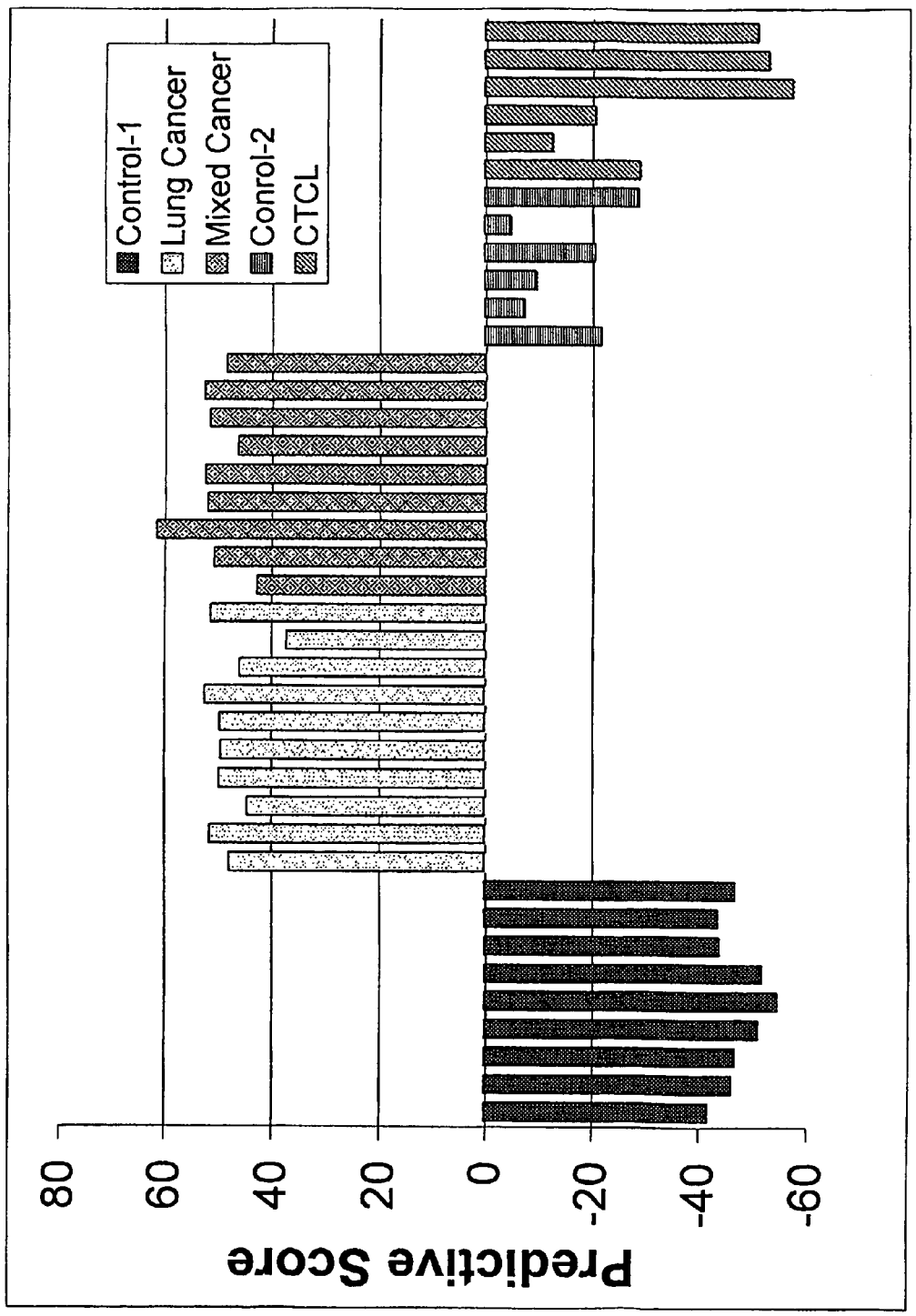
FIG. 16 is a bar graph showing predictive scores for five groups of samples: two control groups and three groups of cancers. Predictive scores were generated by PDA. PDA was trained to distinguish PBMC from lung cancers from PBMC from the tumor controls. The entire dataset was then classified. All of the training samples were properly classified; all of the mixed solid tumors were classified as cancers and the CTCL controls (control-2) samples were classified as controls. The CTCL patient PMBC were classified as controls. PDA clearly distinguishes solid tumor patients from controls, but does not recognize the CTCL samples, which were not part of the training set, as distinct from controls.

All of the cancer patients were ordered by the projections of their gene profile vectors on the average patient-control axis. The results are shown in FIG. 15. Changes in immune gene expression of each sample are relative to the differences between the average patient and average control.

The "mixed cancers" have higher scores (difference from the controls) than all but three of the NSCLC. Surprisingly, there is greater variance in the lung cancers than there is in the "mixed" tumors, which are more homogeneous. This suggests that the strongest component in distinguishing these two groups of cancers by PDA is degree of immune suppression, rather than tissue of origin. In fact, the genes that make up the "growth repression" signature account for most of the effect seen in FIG. 15.

The strong effect shown by all cancers on immune profiles provides evidence that the method of this invention is a sensitive measure of cancer progression.

Example 9

Methods to Compare Cancer Stage to Immune Suppression

Additional experiments compare cancer stage to degree of immune suppression. This comparison allows prediction of outcome. For example, a high degree of suppression by a small tumor is an indicator of an unfavorable prognosis. To extract information on cell-type or organ-specificity of the cancer, it is necessary to eliminate the stage-specific effects. With larger numbers of cancers of two types, the genes most highly correlated with growth suppression are removed, and then differential analysis with PDA is performed using the remaining genes, which are thereby enriched for those carrying tissue specificity, if such genes exist.

A. Samples.

Patient samples include archived viably frozen PBMC from the University of Pennsylvania, and archived viably frozen PBMC from the Fox Chase Institute for Cancer Research. Results obtained from these collections of PBMC are anticipated to be confirmed using whole blood to determine whether this simpler collection methodology yields similar results.

RNA is extracted using the Tri-Reagent™ system, as described by the manufacturer for either isolated PBMC. The RNA is amplified by a modification of the Eberwine procedure, labeled with 33-P dCTP, and each target is successively hybridized to two 9,600-gene filter arrays HA05 and HA06 (Wistar Genomics facility). Images from the hybridized and washed filters are obtained from phosphorimager screens after 4 days of exposure and quantitated using Imagene™ software (Biodiscovery).

B. Confirmation of Informative Genes.

Genes determined by statistical analysis (see below) to be the most informative for class distinctions are confirmed by 1) resequencing the clone from the inventors' collection, and 2) performing real time PCR on samples from the appropriate patient and control classes to confirm the difference in expression values estimated from the arrays.

C. Statistical Considerations and Array Analysis.

Expression values are filtered to exclude values less than twice local background on the array, and values on each array are normalized by the median spot value to correct for variations in target radioactivity. Overall correlation between arrays is determined and arrays not correlating with every other array by at least 80% are repeated. Genes with more than 20% missing values are excluded from analysis, otherwise missing values are interpolated using a published procedure (Troyanskaya, O., et al., 2001 *Bioinformatics* 17:520-52519).

Cancer patients and controls are compared using Penalized Discriminant Analysis (PDA) or PDA as previously described in the preceding examples. Shrunken centroids are used to determine whether any known classes (e.g. for breast cancer, BRCA1, BRCA2, sporadic, ER+, ER−, for lung cancer, adenocarcinoma, squamous cell carcinoma, large cell) have a distinct expression profile. This class is compared separately to controls and samples from patients with other types of cancer in subsequent analyses using PDA.

T-tests are performed between classes to identify individual genes that might serve as biomarkers for a highly specific effect of a tumor on the immune cells. In order to account for false positives derived from multiple testing among informative genes, t-tests are performed on the relevant datasets, and are compared to t-tests on datasets with patients and controls (or two classes of patients) randomly permuted to estimate the possibility that these genes might have been selected by chance. However, the principal means of confirming these classifications is to validate the discriminant functions on independent datasets of patients and controls comprised of new individuals from the various classes of patients.

D. Power Analysis.

Previous experience in determining survival of CTCL patients suggests that approximately 15 to 20 patients of a given immunological class is sufficient to distinguish LT or ST CTCL surviving patients from normal controls. Two power analyses were conducted to determine whether this number of samples is adequate when trying to distinguish classes of PBMC derived from different tumors or from healthy donors. Genes with differential expression between classes ranging from 2.5 to 14 fold were chosen. The number of samples required to distinguish the two classes with equal numbers of each class was analyzed based on published microarray determinations of gene expression levels on a training set of high tumor burden (>60% tumor cells) and a validation set of low tumor burden (5-55% tumor cells) patients. These calculations apply equally to expression levels based on Real time PCR in a clinical setting.

E. Direct Enumeration.

New datasets of increasing but equal numbers of randomly selected patients and controls were created from a dataset of 16 patients and 12 controls. The probability of differential expression between the groups for each number of patients was calculated. This was repeated 100 times. For each gene, the lowest number of patients and controls were found which gave differential expression at $p<0.05$ in at least 95 of the 100 permutations.

Example 10

Ligands to Plastin Tissue 3 (PLS3)

A. Peptide Synthesis

The PLS3 specific peptides Ser-Lys-Asp-Glu-Leu-Asp-Glu-Leu-Lys-Glu-Ala-Phe-Ala-Lys (amino acids 7-20 of SEQ ID NO: 1) and Arg-Glu-Ile-Ile-Gln-Lys-Leu-Met-Leu-Asp-Gly-Asp-Arg-Asn-Lys-Asp (amino acids 51-66 of SEQ ID NO: 1) were synthesized using Fmoc solid phase chemistry on an automated 72-column peptide synthesizer on a 20 mg scale. These PLS3 specific peptides were purified by high performance liquid chromatography (HPLC). The peptides were conjugated to keyhole limpet hemocyanin (KLH) carrier via the branched lysine side chain.

B. Immunization of Rabbits

The peptides were emulsified with Freund's complete adjuvant (CFA) (*Antibodies—A Laboratory Manual*, Eds. E. Harlow and P. Lane, Cold Spring Harbor Laboratory 1998). Four rabbits were injected subcutaneously on day 1 with 0.25 mg of peptide coupled to KLH (2 rabbits/peptide).

Rabbits were boosted via the same route with 0.10 mg conjugated peptide in CFA on days 14, 42, and 56 with KLH conjugate in CFA. Rabbits were bled on days 28, 56, and 70 after the respective booster injections and the serum isolated from each bleeding.

ELISAs were performed after all samples were collected and antibody titers to the injected peptides were determined. The animals were boosted one additional time and the rabbits bled again.

The sera from all bleedings for each peptide were polled and polyclonal antibodies were purified using peptide-conjugated affinity columns.

These PLS3 specific antibodies can be used to identify CTCL T-cells using FACS analysis and immunohistochemistry. For example, a useful assay includes using a fluorescently-labeled antibody to the CD4 T-cell marker, as CTCL cells are primarily of this type, or the CD3 marker which is common to all T-cells in conjunction with PLS3 antibody, which can be visualized with a different fluorescent tag. The inclusion of a marker for the T-cell helps to differentiate the tissue cells and the T-cells of interest. Identification of T-cells that express PLS3 which is normally never expressed in lymphoid cells indicates the presence of cancer cells.

Such a diagnostic assay is useful for both Sezary Syndrome the leukemic form of CTCL and the more common Mycosis Fungoides, which is associated with the skin. For example, in an assay for MF, T-cells are eluted from a skin biopsy for testing or the assay for T-cell may be done in situ in the biopsy using immunoflouescent microscopy. The latter approach may be more difficult as non-lymphoid cells will normally express PLS3.

Each and every patent, patent application, and publication, including websites cited herein is hereby incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

The invention claimed is:

1. A gene expression panel or array indicative of the presence or stage of a cancer, said panel or array consisting of primers or probes capable of detecting genes selected from the group consisting of:
   (i) the genes PLS3, STAT4, TRAIL, CD1D and GATA3;
   (ii) the genes of (i) and one or more additional genes selected from CD26, RhoB, TNFRSF5, SCYA2, PF4, CSPG2, S100A12, KLF4, ARHB, KAL1, JUNB, DUSP1, ITGB1, TOB1, GS3955, IL11RA, C1orf29, MNDA, CX3CR1, DTR, RPA3, MADH7, CD79A, PLAU, SEC61G, and SCYA4; and
   (iii) the genes of (i) and one or more additional genes selected from PTMA, HNRPA1, RPL41, SERPINB6, TACC1, CX3CR1, and HNRPA2B1, ACTR1A, ARPC3, WASF2, SMARCA5, ACTB ARPC4, MYO1E, LDHA, LDHB, ATP5G3, NIMA, CCNF, CDC25A, CDC25B, FCGR3A, GNLY, PRF1, CD8A, CD2, IS2RG, GZMK, ITGAM, PFN1, TIA1, GZMB, and IL2RB.

2. The gene expression panel or array according to claim 1, consisting of the primers or probes capable of detecting genes STAT4, GATA-3, PLS3, CD1D and TRAIL.

3. A diagnostic kit containing probes or primers for measuring the expression of genes consisting of STAT4, GATA-3, PLS3, CD1D and TRAIL.

4. A method of diagnosing or assessing the stage of a cancer, wherein said cancer is a cutaneous T cell lymphoma (CTCL), in a mammalian subject comprising:
   extracting RNA from a biological sample of said subject containing immune cells or cancer cells;
   generating cDNA from said RNA;
   amplifying said cDNA with probes or primers for genes or gene expression products, wherein said genes or gene expression products are selected from the group consisting of:
      (i) PLS3, STAT4, GATA-3, CD1D and TRAIL;
      (ii) the genes of (i) and at least one additional gene selected from the group consisting of CD26 and RhoB;
      (iii) the genes of (i) and at least one additional gene selected from the group consisting of TNFRSF5, SCYA2, PF4, CSPG2, S100A15, KLF4, ARHB, KAL1, JUNB, DUSP1, ITGB1, TOB1, GS3955, IL11RA, C1orf29, MNDA, CX3CR1, DTR, RPA3, MADH7, CD79A, PLAU, SEC61G, and SCYA4;
      (iv) the genes of (i) and at least one additional gene selected from the group consisting of PTMA, HNRPA1, RPL41, SERPINB6, TACC1, CX3CR1, and HNRPA2B1, ACTR1A, ARPC3, WASF2, SMARCA5, ACTB ARPC4, MYO1F, LDHA, LDHB, ATP5G3, NIMA, CCNF, CDC25A, CDC25B, FCGR3A, GNLY, PRF1, CD8A, CD2, IS2RG, GZMK, ITGAM, PFN1, TIA1, GZMB, and IL2RB; and
      (v) the genes of (i) and at least one gene selected from the group consisting of cathepsin C; TIA1 cytotoxic granule-associated RNA binding protein; interleukin 2 receptor β; Fc fragment of IgG, low affinity IIIa, receptor for CD16; granzyme B granzyme 2, cytotoxic T-lymphocyte-associated serine esterase 1; CD2 antigen p50, sheep red blood cell receptor; CD8 antigen, alpha polypeptide p32; integrin, alpha M complement component receptor 3α; perforin, mRNA sequence; granzyme K serine protease, granzyme 3; tryptase II; profilin 1; interleukin 2 receptor, gamma severe combined immunodeficiency; and granulysin;
   obtaining from said amplified cDNA a profile of the expression levels of the selected genes or gene expression products in said sample; and
   diagnosing said cancer based upon a variance in the obtained profile of expression levels of the said selected genes or gene expression products in said subject's sample from the same selected genes or gene expression products of a control gene expression profile from a similar biological sample of a healthy subject, or diagnosing said cancer based upon a similarity in the obtained profile of expression levels of said selected genes or gene expression products in said subject's sample to the same selected genes or gene expression products in a gene expression profile characteristic of said cancer or a stage or variant of said cancer.

5. The method according to claim 4, wherein said profile is provided in the form of a graph or tree view.

6. The method according to claim 4, wherein said sample is peripheral blood.

7. The method according to claim 4, wherein said immune cells are peripheral blood mononuclear cells.

8. The method according to claim 4, wherein said statistically significant number of genes consists of the genes STAT4, GATA-3, PLS3, CD1D and TRAIL.

9. The method according to claim 4, wherein a gene profile formed by a decreased level of STAT4 and increased levels of PLS3, TRAIL, GATA3 and CD1D as compared to said healthy profile is indicative of a CTCL.

10. A method for diagnosing a cutaneous T cell lymphoma (CTCL) in a mammalian subject comprising
   extracting RNA from a biological sample containing immune cells or cancer cells of the subject;
   generating cDNA from said RNA;
   amplifying said cDNA with probes or primers for a statistically significant number of genes or gene expression products;
   obtaining from said amplified cDNA the expression levels of said genes or gene expression products in said sample;
   diagnosing CTCL based upon a variance in the pattern of obtained expression levels of the said genes or gene expression products consisting of STAT4, GATA-3, PLS3, CD1D and TRAIL that form a gene expression profile characteristic of CTCL in said subject's sample.

11. A method of diagnosing or assessing the stage of a CTCL in a mammalian subject comprising:
   amplifying cDNA from a biological sample containing immune cells or cancer cells of the subject to obtain expression levels of a statistically significant number of genes or gene expression products obtained from said sample, wherein said genes or gene expression products are selected from the group consisting of:
   (i) PLS3, STAT4, GATA-3, CD1D and TRAIL;
   (ii) the genes of (i) and at least one additional gene selected from the group consisting of CD26 and RhoB;
   (iii) the genes of (i) and at least one additional gene selected from the group consisting of TNFRSF5, SCYA2, PF4, CSPG2, S100A15, KLF4, ARHB, KAL1, JUNB, DUSP1, ITGB1, TOB1, GS3955, IL11RA, C1orf29, MNDA, CX3CR1, DTR, RPA3, MADH7, CD79A, PLAU, SEC61G, and SCYA4;
   (iv) the genes of (i) and at least one additional gene selected from the group consisting of PTMA, HNRPA1, RPL41, SERPINB6, TACC1, CX3CR1, and HNRPA2B1, ACTR1A, ARPC3, WASF2, SMARCA5, ACTB ARPC4, MYO1F, LDHA, LDHB, ATP5G3, NIMA, CCNF, CDC25A, CDC25B, FCGR3A, GNLY, PRF1, CD8A, CD2, IS2RG, GZMK, ITGAM, PFN1, TIA1, GZMB, and IL2RB; and
   (v) the genes of (i) and at least one gene selected from the group consisting of cathepsin C; TIA1 cytotoxic granule-associated RNA binding protein; interleukin 2 receptor β; Fc fragment of IgG, low affinity IIIa, receptor for CD16; granzyme B granzyme 2, cytotoxic T-lymphocyte-associated serine esterase 1; CD2 antigen p50, sheep red blood cell receptor; CD8 antigen, alpha polypeptide p32; integrin, alpha M complement component receptor 3α; perform mRNA sequence; granzyme K serine protease, granzyme 3; tryptase II; profilin 1; interleukin 2 receptor, gamma severe combined immunodeficiency; and granulysin
   diagnosing CTCL or a stage thereof based on a change in a profile of expression levels between said selected genes or gene products of said sample from the same selected genes or gene products of a control healthy expression profile, wherein said change indicates a diagnosis or stage of a CTCL.

12. The method according to claim 11, wherein said change is an increase in expression level of a genes or gene product of said profile.

13. The method according to claim 11, wherein said change is a decrease in expression level of a gene or gene product of said profile.

14. The method according to claim 11, wherein said statistically significant number of genes are (i).

15. The method according to claim 11, wherein said statistically significant number of genes are (ii).

16. The method according to claim 11, wherein said statistically significant number of genes are (iii).

17. The method according to claim 11, wherein said statistically significant number of genes are (iv).

18. The method according to claim 11, wherein said statistically significant number of genes are (v).

19. The method according to claim 11, wherein said control expression profile is a gene expression profile from a similar biological sample of a healthy subject.

20. The method according to claim 11, wherein said control expression profile is a gene expression profile characteristic of said CTCL.

* * * * *

UNITED STATES PATENT AND TRADEMARK OFFICE
CERTIFICATE OF CORRECTION

PATENT NO. : 7,640,114 B2
APPLICATION NO. : 10/558252
DATED : December 29, 2009
INVENTOR(S) : Showe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 812 days.

Signed and Sealed this

Ninth Day of November, 2010

David J. Kappos
*Director of the United States Patent and Trademark Office*

SEQUENCE LISTING

```
<160> NUMBER OF SEQ ID NOS: 87

<210> SEQ ID NO 1
<211> LENGTH: 627
<212> TYPE: PRT
<213> ORGANISM: human plastin T protein

<400> SEQUENCE: 1

Met Ala Thr Thr Gln Ile Ser Lys Asp Glu Leu Asp Glu Leu Lys Glu
1               5                   10                  15

Ala Phe Ala Lys Val Asp Leu Asn Ser Asn Gly Phe Ile Cys Asp Tyr
            20                  25                  30

Glu Leu His Glu Leu Phe Lys Glu Ala Asn Met Pro Leu Pro Gly Tyr
        35                  40                  45

Lys Val Arg Glu Ile Ile Gln Lys Leu Met Leu Asp Gly Asp Arg Asn
    50                  55                  60

Lys Asp Gly Lys Ile Ser Phe Asp Glu Phe Val Tyr Ile Phe Gln Glu
65                  70                  75                  80

Val Lys Ser Ser Asp Ile Ala Lys Thr Phe Arg Lys Ala Ile Asn Arg
                85                  90                  95

Lys Glu Gly Ile Cys Ala Leu Gly Gly Thr Ser Glu Leu Ser Ser Glu
            100                 105                 110

Gly Thr Gln His Ser Tyr Ser Glu Glu Glu Lys Tyr Ala Phe Val Asn
        115                 120                 125

Trp Ile Asn Lys Ala Leu Glu Asn Asp Pro Asp Cys Arg His Val Ile
    130                 135                 140

Pro Met Asn Pro Asn Thr Asp Asp Leu Phe Lys Ala Val Gly Asp Gly
145                 150                 155                 160

Ile Val Leu Cys Lys Met Ile Asn Leu Ser Val Pro Asp Thr Ile Asp
                165                 170                 175

Glu Arg Ala Ile Asn Lys Lys Lys Leu Thr Pro Phe Ile Ile Gln Glu
            180                 185                 190

Asn Leu Asn Leu Ala Leu Asn Ser Ala Ser Ala Ile Gly Cys His Val
        195                 200                 205

Val Asn Ile Gly Ala Glu Asp Leu Arg Ala Gly Lys Pro His Leu Val
    210                 215                 220
```

-continued

```
Leu Gly Leu Leu Trp Gln Ile Ile Lys Ile Gly Leu Phe Ala Asp Ile
225                 230                 235                 240

Glu Leu Ser Arg Asn Glu Ala Leu Ala Ala Leu Leu Arg Asp Gly Glu
                245                 250                 255

Thr Leu Glu Glu Leu Met Lys Leu Ser Pro Glu Glu Leu Leu Leu Arg
            260                 265                 270

Trp Ala Asn Phe His Leu Glu Asn Ser Gly Trp Gln Lys Ile Asn Asn
        275                 280                 285

Phe Ser Ala Asp Ile Lys Asp Ser Lys Ala Tyr Phe His Leu Leu Asn
    290                 295                 300

Gln Ile Ala Pro Lys Gly Gln Lys Glu Gly Glu Pro Arg Ile Asp Ile
305                 310                 315                 320

Asn Met Ser Gly Phe Asn Glu Thr Asp Asp Leu Lys Arg Ala Glu Ser
                325                 330                 335

Met Leu Gln Gln Ala Asp Lys Leu Gly Cys Arg Gln Phe Val Thr Pro
            340                 345                 350

Ala Asp Val Val Ser Gly Asn Pro Lys Leu Asn Leu Ala Phe Val Ala
        355                 360                 365

Asn Leu Phe Asn Lys Tyr Pro Ala Leu Thr Lys Pro Glu Asn Gln Asp
    370                 375                 380

Ile Asp Trp Thr Leu Leu Glu Gly Glu Thr Arg Glu Glu Arg Thr Phe
385                 390                 395                 400

Arg Asn Trp Met Asn Ser Leu Gly Val Asn Pro His Val Asn His Leu
                405                 410                 415

Tyr Ala Asp Leu Gln Asp Ala Leu Val Ile Leu Gln Leu Tyr Glu Arg
            420                 425                 430

Ile Lys Val Pro Val Asp Trp Ser Lys Val Asn Lys Pro Pro Tyr Pro
        435                 440                 445

Lys Leu Gly Ala Asn Met Lys Lys Leu Glu Asn Cys Asn Tyr Ala Val
    450                 455                 460

Glu Leu Gly Lys His Pro Ala Lys Phe Ser Leu Val Gly Ile Gly Gly
465                 470                 475                 480

Gln Asp Leu Asn Asp Gly Asn Gln Thr Leu Thr Leu Ala Leu Val Trp
                485                 490                 495

Gln Leu Met Arg Arg Tyr Thr Leu Asn Val Leu Glu Asp Leu Gly Asp
            500                 505                 510

Gly Gln Lys Ala Asn Asp Asp Ile Ile Val Asn Trp Val Asn Arg Thr
        515                 520                 525

Leu Ser Glu Ala Gly Lys Ser Thr Ser Ile Gln Ser Phe Lys Asp Lys
    530                 535                 540

Thr Ile Ser Ser Ser Leu Ala Val Val Asp Leu Ile Asp Ala Ile Gln
545                 550                 555                 560

Pro Gly Cys Ile Asn Tyr Asp Leu Val Lys Ser Gly Asn Leu Thr Glu
                565                 570                 575

Asp Asp Lys His Asn Asn Ala Lys Tyr Ala Val Ser Met Ala Arg Arg
            580                 585                 590

Ile Gly Ala Arg Val Tyr Ala Leu Pro Glu Asp Leu Val Glu Val Lys
        595                 600                 605

Pro Lys Met Val Met Thr Val Phe Ala Cys Leu Met Gly Arg Gly Met
    610                 615                 620

Lys Arg Val
625
```

<210> SEQ ID NO 2
<211> LENGTH: 21
<212> TYPE: DNA
<213> ORGANISM: Artificial
<220> FEATURE:
<223> OTHER INFORMATION: SF3A1 primer

<400> SEQUENCE: 2
ggataagacg gaatggaaac t                                              21

<210> SEQ ID NO 3
<211> LENGTH: 18
<212> TYPE: DNA
<213> ORGANISM: Artificial
<220> FEATURE:
<223> OTHER INFORMATION: SF3A1 primer

<400> SEQUENCE: 3
aatggcaggg acttgaca                                                  18

<210> SEQ ID NO 4
<211> LENGTH: 24
<212> TYPE: DNA
<213> ORGANISM: Artificial
<220> FEATURE:
<223> OTHER INFORMATION: CCT3 primer

<400> SEQUENCE: 4
agctgggaca gaaagaaagg gact                                           24

<210> SEQ ID NO 5
<211> LENGTH: 20
<212> TYPE: DNA
<213> ORGANISM: Artificial
<220> FEATURE:
<223> OTHER INFORMATION: CCT3 primer

<400> SEQUENCE: 5
aacagtggaa gacggcagtt                                                20

<210> SEQ ID NO 6
<211> LENGTH: 18
<212> TYPE: DNA
<213> ORGANISM: Artificial
<220> FEATURE:
<223> OTHER INFORMATION: GATA3 primer

<400> SEQUENCE: 6
tatccatcgc gtttaggc                                                  18

<210> SEQ ID NO 7
<211> LENGTH: 19
<212> TYPE: DNA
<213> ORGANISM: Artificial
<220> FEATURE:
<223> OTHER INFORMATION: GATA3 primer

<400> SEQUENCE: 7
cccaagaaca gctcgttta                                                 19

<210> SEQ ID NO 8
<211> LENGTH: 18
<212> TYPE: DNA
<213> ORGANISM: Artificial
<220> FEATURE:
<223> OTHER INFORMATION: ARIO3 primer

```
<400> SEQUENCE: 8
ataggcccca atacttgt                                              18

<210> SEQ ID NO 9
<211> LENGTH: 19
<212> TYPE: DNA
<213> ORGANISM: Artificial
<220> FEATURE:
<223> OTHER INFORMATION: ARIO3 primer

<400> SEQUENCE: 9
acacttaatg cactcgtca                                             19

<210> SEQ ID NO 10
<211> LENGTH: 17
<212> TYPE: DNA
<213> ORGANISM: Artificial
<220> FEATURE:
<223> OTHER INFORMATION: DUSPI primer

<400> SEQUENCE: 10
tgaaggcaga cacctac                                               17

<210> SEQ ID NO 11
<211> LENGTH: 18
<212> TYPE: DNA
<213> ORGANISM: Artificial
<220> FEATURE:
<223> OTHER INFORMATION: DUSPI primer

<400> SEQUENCE: 11
gcacattcgg gaccaata                                              18

<210> SEQ ID NO 12
<211> LENGTH: 18
<212> TYPE: DNA
<213> ORGANISM: Artificial
<220> FEATURE:
<223> OTHER INFORMATION: PLS3 primer

<400> SEQUENCE: 12
gcttgacaaa gcaagagt                                              18

<210> SEQ ID NO 13
<211> LENGTH: 19
<212> TYPE: DNA
<213> ORGANISM: Artificial
<220> FEATURE:
<223> OTHER INFORMATION: PLS3 primer

<400> SEQUENCE: 13
gcatcttccc tctcatacc                                             19

<210> SEQ ID NO 14
<211> LENGTH: 20
<212> TYPE: DNA
<213> ORGANISM: Artificial
<220> FEATURE:
<223> OTHER INFORMATION: CDSIW primer

<400> SEQUENCE: 14
ccctgctata cataaaggtg                                            20

<210> SEQ ID NO 15
<211> LENGTH: 22
```

<212> TYPE: DNA
<213> ORGANISM: Artificial
<220> FEATURE:
<223> OTHER INFORMATION: CDSIW primer

<400> SEQUENCE: 15
gcttgtgaga ttgagaatga ac                                    22

<210> SEQ ID NO 16
<211> LENGTH: 18
<212> TYPE: DNA
<213> ORGANISM: Artificial
<220> FEATURE:
<223> OTHER INFORMATION: ISGI5 primer

<400> SEQUENCE: 16
gcttgaggcc gtactccc                                         18

<210> SEQ ID NO 17
<211> LENGTH: 20
<212> TYPE: DNA
<213> ORGANISM: Artificial
<220> FEATURE:
<223> OTHER INFORMATION: ISGI5 primer

<400> SEQUENCE: 17
caaatgcgac gaacctctga                                       20

<210> SEQ ID NO 18
<211> LENGTH: 20
<212> TYPE: DNA
<213> ORGANISM: Artificial
<220> FEATURE:
<223> OTHER INFORMATION: ITGB1 primer

<400> SEQUENCE: 18
gcttccatat cagcagtaat                                       20

<210> SEQ ID NO 19
<211> LENGTH: 19
<212> TYPE: DNA
<213> ORGANISM: Artificial
<220> FEATURE:
<223> OTHER INFORMATION: ITGB1 primer

<400> SEQUENCE: 19
gtagaaagtc gggacaaat                                        19

<210> SEQ ID NO 20
<211> LENGTH: 17
<212> TYPE: DNA
<213> ORGANISM: Artificial
<220> FEATURE:
<223> OTHER INFORMATION: CDKN2 primer

<400> SEQUENCE: 20
dctgctgaag caaggtg                                          17

<210> SEQ ID NO 21
<211> LENGTH: 18
<212> TYPE: DNA
<213> ORGANISM: Artificial
<220> FEATURE:
<223> OTHER INFORMATION: CDKN2 primer

<400> SEQUENCE: 21

```
cagtgtgacc ctcttgaa                                            18
```

<210> SEQ ID NO 22
<211> LENGTH: 21
<212> TYPE: DNA
<213> ORGANISM: Artificial
<220> FEATURE:
<223> OTHER INFORMATION: CCR1 primer

<400> SEQUENCE: 22

```
gggtaaatgg aaatgatgag t                                        21
```

<210> SEQ ID NO 23
<211> LENGTH: 21
<212> TYPE: DNA
<213> ORGANISM: Artificial
<220> FEATURE:
<223> OTHER INFORMATION: CCR1 primer

<400> SEQUENCE: 23

```
gagttgagac ctaacgagaa a                                        21
```

<210> SEQ ID NO 24
<211> LENGTH: 21
<212> TYPE: DNA
<213> ORGANISM: Artificial
<220> FEATURE:
<223> OTHER INFORMATION: JUNB primer

<400> SEQUENCE: 24

```
actctttaga gactaagtgc g                                        21
```

<210> SEQ ID NO 25
<211> LENGTH: 18
<212> TYPE: DNA
<213> ORGANISM: Artificial
<220> FEATURE:
<223> OTHER INFORMATION: JUNB primer

<400> SEQUENCE: 25

```
ccacctcgac gtttacaa                                            18
```

<210> SEQ ID NO 26
<211> LENGTH: 23
<212> TYPE: DNA
<213> ORGANISM: Artificial
<220> FEATURE:
<223> OTHER INFORMATION: CYPTB1 primer

<400> SEQUENCE: 26

```
ttggtatatc aaacagtaaa ggc                                      23
```

<210> SEQ ID NO 27
<211> LENGTH: 19
<212> TYPE: DNA
<213> ORGANISM: Artificial
<220> FEATURE:
<223> OTHER INFORMATION: CYPTB1 primer

<400> SEQUENCE: 27

```
tcatgtccca gaacttagc                                           19
```

<210> SEQ ID NO 28
<211> LENGTH: 25
<212> TYPE: DNA
<213> ORGANISM: Artificial

```
<220> FEATURE:
<223> OTHER INFORMATION: STAT2 primer

<400> SEQUENCE: 28
tcctagaacc tggatattta caaag                                          25

<210> SEQ ID NO 29
<211> LENGTH: 17
<212> TYPE: DNA
<213> ORGANISM: Artificial
<220> FEATURE:
<223> OTHER INFORMATION: STAT2 primer

<400> SEQUENCE: 29
gtgtatgccg gtgttga                                                   17

<210> SEQ ID NO 30
<211> LENGTH: 20
<212> TYPE: DNA
<213> ORGANISM: Artificial
<220> FEATURE:
<223> OTHER INFORMATION: ARIIGEF6 primer

<400> SEQUENCE: 30
tgctctcaga ttaacatggc                                                20

<210> SEQ ID NO 31
<211> LENGTH: 24
<212> TYPE: DNA
<213> ORGANISM: Artificial
<220> FEATURE:
<223> OTHER INFORMATION: ARIIGEF6 primer

<400> SEQUENCE: 31
ggaatacttt agttgattgc tgaa                                           24

<210> SEQ ID NO 32
<211> LENGTH: 20
<212> TYPE: DNA
<213> ORGANISM: Artificial
<220> FEATURE:
<223> OTHER INFORMATION: SELL primer

<400> SEQUENCE: 32
ctcatcatgg gttggattag                                                20

<210> SEQ ID NO 33
<211> LENGTH: 19
<212> TYPE: DNA
<213> ORGANISM: Artificial
<220> FEATURE:
<223> OTHER INFORMATION: SELL primer

<400> SEQUENCE: 33
ctgcaagtga catctctttt                                                19

<210> SEQ ID NO 34
<211> LENGTH: 21
<212> TYPE: DNA
<213> ORGANISM: Artificial
<220> FEATURE:
<223> OTHER INFORMATION: CDSA primer

<400> SEQUENCE: 34
ataacagcat agtacaaccc t                                              21
```

<210> SEQ ID NO 35
<211> LENGTH: 19
<212> TYPE: DNA
<213> ORGANISM: Artificial
<220> FEATURE:
<223> OTHER INFORMATION: CDSA primer

<400> SEQUENCE: 35
gtatggtaca agcaatgcc                                               19

<210> SEQ ID NO 36
<211> LENGTH: 18
<212> TYPE: DNA
<213> ORGANISM: Artificial
<220> FEATURE:
<223> OTHER INFORMATION: DPPS primer

<400> SEQUENCE: 36
ttgaattatc cggtcggg                                                18

<210> SEQ ID NO 37
<211> LENGTH: 18
<212> TYPE: DNA
<213> ORGANISM: Artificial
<220> FEATURE:
<223> OTHER INFORMATION: DPPS primer

<400> SEQUENCE: 37
cctggtcgtg ttggtatg                                                18

<210> SEQ ID NO 38
<211> LENGTH: 21
<212> TYPE: DNA
<213> ORGANISM: Artificial
<220> FEATURE:
<223> OTHER INFORMATION: PPIA primer

<400> SEQUENCE: 38
cgtaaaccct ggaataattc t                                            21

<210> SEQ ID NO 39
<211> LENGTH: 19
<212> TYPE: DNA
<213> ORGANISM: Artificial
<220> FEATURE:
<223> OTHER INFORMATION: PPIA primer

<400> SEQUENCE: 39
ctgtgtctcc ttcgaggta                                               19

<210> SEQ ID NO 40
<211> LENGTH: 22
<212> TYPE: DNA
<213> ORGANISM: Artificial
<220> FEATURE:
<223> OTHER INFORMATION: ZNF161  primer

<400> SEQUENCE: 40
caggtcacaa tccctattat ac                                           22

<210> SEQ ID NO 41
<211> LENGTH: 18
<212> TYPE: DNA
<213> ORGANISM: Artificial
<220> FEATURE:
<223> OTHER INFORMATION: ZNF161 primer

<400> SEQUENCE: 41
acactagcag gactcttc                                                      18

<210> SEQ ID NO 42
<211> LENGTH: 22
<212> TYPE: DNA
<213> ORGANISM: Artificial
<220> FEATURE:
<223> OTHER INFORMATION: SOD1 primer

<400> SEQUENCE: 42
ccacataata agtgccatac ag                                                 22

<210> SEQ ID NO 43
<211> LENGTH: 23
<212> TYPE: DNA
<213> ORGANISM: Artificial
<220> FEATURE:
<223> OTHER INFORMATION: SOD1 primer

<400> SEQUENCE: 43
ccttaaaagt gtaattgtgt gtc                                                23

<210> SEQ ID NO 44
<211> LENGTH: 20
<212> TYPE: DNA
<213> ORGANISM: Artificial
<220> FEATURE:
<223> OTHER INFORMATION: ICAM2 primer

<400> SEQUENCE: 44
agaaggtatt cgaggtacac                                                    20

<210> SEQ ID NO 45
<211> LENGTH: 16
<212> TYPE: DNA
<213> ORGANISM: Artificial
<220> FEATURE:
<223> OTHER INFORMATION: ICAM2 primer

<400> SEQUENCE: 45
gtacacgctg acgttg                                                        16

<210> SEQ ID NO 46
<211> LENGTH: 21
<212> TYPE: DNA
<213> ORGANISM: Artificial
<220> FEATURE:
<223> OTHER INFORMATION: TNFRST6 primer

<400> SEQUENCE: 46
acgtctgttg ctagattatc g                                                  21

<210> SEQ ID NO 47
<211> LENGTH: 16
<212> TYPE: DNA
<213> ORGANISM: Artificial
<220> FEATURE:
<223> OTHER INFORMATION: TNFRST6 primer

<400> SEQUENCE: 47
cacgcagtct ggttca                                                        16

<210> SEQ ID NO 48

```
<211> LENGTH: 19
<212> TYPE: DNA
<213> ORGANISM: Artificial
<220> FEATURE:
<223> OTHER INFORMATION: TNFST6 primer

<400> SEQUENCE: 48
aaggtctaca tgaggaact                                           19

<210> SEQ ID NO 49
<211> LENGTH: 17
<212> TYPE: DNA
<213> ORGANISM: Artificial
<220> FEATURE:
<223> OTHER INFORMATION: TNFST6 primer

<400> SEQUENCE: 49
agccgaaaaa cgtctga                                             17

<210> SEQ ID NO 50
<211> LENGTH: 16
<212> TYPE: DNA
<213> ORGANISM: Artificial
<220> FEATURE:
<223> OTHER INFORMATION: LCP1 primer

<400> SEQUENCE: 50
atagagggcg tcttgc                                              16

<210> SEQ ID NO 51
<211> LENGTH: 18
<212> TYPE: DNA
<213> ORGANISM: Artificial
<220> FEATURE:
<223> OTHER INFORMATION: LCP1 primer

<400> SEQUENCE: 51
ctcacataca cacacacc                                            18

<210> SEQ ID NO 52
<211> LENGTH: 19
<212> TYPE: DNA
<213> ORGANISM: Artificial
<220> FEATURE:
<223> OTHER INFORMATION: ILI8 primer

<400> SEQUENCE: 52
ggatgaattg ggggataga                                           19

<210> SEQ ID NO 53
<211> LENGTH: 21
<212> TYPE: DNA
<213> ORGANISM: Artificial
<220> FEATURE:
<223> OTHER INFORMATION: ILI8 primer

<400> SEQUENCE: 53
gtcactacac tcagctaatt t                                        21

<210> SEQ ID NO 54
<211> LENGTH: 20
<212> TYPE: DNA
<213> ORGANISM: Artificial
<220> FEATURE:
<223> OTHER INFORMATION: TNFRST5 primer

<400> SEQUENCE: 54
```
cactatcaca aacaatgctg                                      20

<210> SEQ ID NO 55
<211> LENGTH: 19
<212> TYPE: DNA
<213> ORGANISM: Artificial
<220> FEATURE:
<223> OTHER INFORMATION: TNFRST5 primer

<400> SEQUENCE: 55
accttgaaga acctctcac                                       19

<210> SEQ ID NO 56
<211> LENGTH: 21
<212> TYPE: DNA
<213> ORGANISM: Artificial
<220> FEATURE:
<223> OTHER INFORMATION: TNFST5 primer

<400> SEQUENCE: 56
tatacactcc aaggcatgta g                                    21

<210> SEQ ID NO 57
<211> LENGTH: 18
<212> TYPE: DNA
<213> ORGANISM: Artificial
<220> FEATURE:
<223> OTHER INFORMATION: TNFST5 primer

<400> SEQUENCE: 57
ctccccattt cccttctg                                        18

<210> SEQ ID NO 58
<211> LENGTH: 17
<212> TYPE: DNA
<213> ORGANISM: Artificial
<220> FEATURE:
<223> OTHER INFORMATION: MGAM primer

<400> SEQUENCE: 58
attattcctc ccaccgc                                         17

<210> SEQ ID NO 59
<211> LENGTH: 17
<212> TYPE: DNA
<213> ORGANISM: Artificial
<220> FEATURE:
<223> OTHER INFORMATION: MGAM primer

<400> SEQUENCE: 59
tgaactgggt ccatgat                                         17

<210> SEQ ID NO 60
<211> LENGTH: 19
<212> TYPE: DNA
<213> ORGANISM: Artificial
<220> FEATURE:
<223> OTHER INFORMATION: CD44 primer

<400> SEQUENCE: 60
atggttatgt ttccaacgg                                       19

<210> SEQ ID NO 61
<211> LENGTH: 18
<212> TYPE: DNA

```
<213> ORGANISM: Artificial
<220> FEATURE:
<223> OTHER INFORMATION: CD44 primer

<400> SEQUENCE: 61
gtggactcaa cggagagg                                              18

<210> SEQ ID NO 62
<211> LENGTH: 20
<212> TYPE: DNA
<213> ORGANISM: Artificial
<220> FEATURE:
<223> OTHER INFORMATION: NFKDIA primer

<400> SEQUENCE: 62
gtacagcatt tacaggaggg                                            20

<210> SEQ ID NO 63
<211> LENGTH: 17
<212> TYPE: DNA
<213> ORGANISM: Artificial
<220> FEATURE:
<223> OTHER INFORMATION: NFKDIA primer

<400> SEQUENCE: 63
ctcacctttg tggggtt                                               17

<210> SEQ ID NO 64
<211> LENGTH: 19
<212> TYPE: DNA
<213> ORGANISM: Artificial
<220> FEATURE:
<223> OTHER INFORMATION: NFKB1 primer

<400> SEQUENCE: 64
tacaggtcca gggtatagc                                             19

<210> SEQ ID NO 65
<211> LENGTH: 20
<212> TYPE: DNA
<213> ORGANISM: Artificial
<220> FEATURE:
<223> OTHER INFORMATION: NFKB1 primer

<400> SEQUENCE: 65
gctctgtggt ttcaataact                                            20

<210> SEQ ID NO 66
<211> LENGTH: 18
<212> TYPE: DNA
<213> ORGANISM: Artificial
<220> FEATURE:
<223> OTHER INFORMATION: MBO4 primer

<400> SEQUENCE: 66
cacatctctc cagtctgc                                              18

<210> SEQ ID NO 67
<211> LENGTH: 20
<212> TYPE: DNA
<213> ORGANISM: Artificial
<220> FEATURE:
<223> OTHER INFORMATION: MBO4 primer

<400> SEQUENCE: 67
cgacgtaaag cctttaagaa                                            20
```

<210> SEQ ID NO 68
<211> LENGTH: 17
<212> TYPE: DNA
<213> ORGANISM: Artificial
<220> FEATURE:
<223> OTHER INFORMATION: CDID primer

<400> SEQUENCE: 68
tgagacgcct ctgtttc                                                    17

<210> SEQ ID NO 69
<211> LENGTH: 22
<212> TYPE: DNA
<213> ORGANISM: Artificial
<220> FEATURE:
<223> OTHER INFORMATION: CDID primer

<400> SEQUENCE: 69
acacctcaaa tacataccta ct                                              22

<210> SEQ ID NO 70
<211> LENGTH: 21
<212> TYPE: DNA
<213> ORGANISM: Artificial
<220> FEATURE:
<223> OTHER INFORMATION: CX3CRI primer

<400> SEQUENCE: 70
agtaatggca agtaaattgg g                                               21

<210> SEQ ID NO 71
<211> LENGTH: 19
<212> TYPE: DNA
<213> ORGANISM: Artificial
<220> FEATURE:
<223> OTHER INFORMATION: CX3CRI primer

<400> SEQUENCE: 71
caaatagtgc tcgctttct                                                  19

<210> SEQ ID NO 72
<211> LENGTH: 18
<212> TYPE: DNA
<213> ORGANISM: Artificial
<220> FEATURE:
<223> OTHER INFORMATION: ILIR2 primer

<400> SEQUENCE: 72
aggacacagc ggtaatag                                                   18

<210> SEQ ID NO 73
<211> LENGTH: 17
<212> TYPE: DNA
<213> ORGANISM: Artificial
<220> FEATURE:
<223> OTHER INFORMATION: ILIR2 primer

<400> SEQUENCE: 73
ccattgagcc tcagagt                                                    17

<210> SEQ ID NO 74
<211> LENGTH: 19
<212> TYPE: DNA
<213> ORGANISM: Artificial
<220> FEATURE:

```
<223> OTHER INFORMATION: I%FSFIO primer

<400> SEQUENCE: 74
acgtgtactt taccaacga                                                    19

<210> SEQ ID NO 75
<211> LENGTH: 16
<212> TYPE: DNA
<213> ORGANISM: Artificial
<220> FEATURE:
<223> OTHER INFORMATION: I%FSFIO primer

<400> SEQUENCE: 75
atgcccactc cttgat                                                       16

<210> SEQ ID NO 76
<211> LENGTH: 22
<212> TYPE: DNA
<213> ORGANISM: Artificial
<220> FEATURE:
<223> OTHER INFORMATION: ILIRI primer

<400> SEQUENCE: 76
atggctcaat accttttatt gc                                                22

<210> SEQ ID NO 77
<211> LENGTH: 21
<212> TYPE: DNA
<213> ORGANISM: Artificial
<220> FEATURE:
<223> OTHER INFORMATION: ILIRI primer

<400> SEQUENCE: 77
aaaactttta atgccttcca c                                                 21

<210> SEQ ID NO 78
<211> LENGTH: 18
<212> TYPE: DNA
<213> ORGANISM: Artificial
<220> FEATURE:
<223> OTHER INFORMATION: GATA3 primer

<400> SEQUENCE: 78
tatccatcgc gtttaggc                                                     18

<210> SEQ ID NO 79
<211> LENGTH: 19
<212> TYPE: DNA
<213> ORGANISM: Artificial
<220> FEATURE:
<223> OTHER INFORMATION: GATA3 primer

<400> SEQUENCE: 79
cccaagaaca gctcgttta                                                    19

<210> SEQ ID NO 80
<211> LENGTH: 18
<212> TYPE: DNA
<213> ORGANISM: Artificial
<220> FEATURE:
<223> OTHER INFORMATION: PLS3 primer

<400> SEQUENCE: 80
gcttgacaaa gcaagagt                                                     18
```

```
<210> SEQ ID NO 81
<211> LENGTH: 19
<212> TYPE: DNA
<213> ORGANISM: Artificial
<220> FEATURE:
<223> OTHER INFORMATION: PLS3 primer

<400> SEQUENCE: 81
gcatcttccc tctcatacc                                                  19

<210> SEQ ID NO 82
<211> LENGTH: 25
<212> TYPE: DNA
<213> ORGANISM: Artificial
<220> FEATURE:
<223> OTHER INFORMATION: STAT4 primer
<220> FEATURE:
<221> NAME/KEY: misc_feature
<222> LOCATION: (14)..(14)
<223> OTHER INFORMATION: n is a, c, g, or t

<400> SEQUENCE: 82
tcctagaacc tggntattta caaag                                           25

<210> SEQ ID NO 83
<211> LENGTH: 17
<212> TYPE: DNA
<213> ORGANISM: Artificial
<220> FEATURE:
<223> OTHER INFORMATION: STAT4 primer

<400> SEQUENCE: 83
gtgtatgccg gtgttga                                                    17

<210> SEQ ID NO 84
<211> LENGTH: 17
<212> TYPE: DNA
<213> ORGANISM: Artificial
<220> FEATURE:
<223> OTHER INFORMATION: CD1D primer

<400> SEQUENCE: 84
tgagacgcct ctgtttc                                                    17

<210> SEQ ID NO 85
<211> LENGTH: 22
<212> TYPE: DNA
<213> ORGANISM: Artificial
<220> FEATURE:
<223> OTHER INFORMATION: CD1D primer

<400> SEQUENCE: 85
acacctcaaa tacataccta ct                                              22

<210> SEQ ID NO 86
<211> LENGTH: 19
<212> TYPE: DNA
<213> ORGANISM: Artificial
<220> FEATURE:
<223> OTHER INFORMATION: TRAIL primer

<400> SEQUENCE: 86
acgtgtactt taccaacga                                                  19

<210> SEQ ID NO 87
<211> LENGTH: 16
<212> TYPE: DNA
```

-continued

```
<213> ORGANISM: Artificial
<220> FEATURE:
<223> OTHER INFORMATION: TRAIL primer

<400> SEQUENCE: 87
atgcccactc cttgat                                                    16
```